(12) United States Patent
Bruce et al.

(10) Patent No.: US 12,258,375 B2
(45) Date of Patent: *Mar. 25, 2025

(54) MUTANT LYSENIN PORES

(71) Applicant: Oxford Nanopore Technologies PLC, Oxford (GB)

(72) Inventors: Mark John Bruce, Oxford (GB); James Anthony Clarke, Oxford (GB); Andrew John Heron, Oxford (GB); Lakmal Nishantha Jayasinghe, Oxford (GB); Elizabeth Jayne Wallace, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/504,590

(22) Filed: Nov. 8, 2023

(65) Prior Publication Data

US 2024/0199711 A1 Jun. 20, 2024

Related U.S. Application Data

(63) Continuation of application No. 17/108,536, filed on Dec. 1, 2020, now Pat. No. 11,845,780, which is a continuation of application No. 15/692,498, filed on Aug. 31, 2017, now Pat. No. 10,882,889, which is a continuation of application No. 14/391,660, filed as application No. PCT/GB2013/050667 on Mar. 15, 2013, now Pat. No. 9,777,049.

(60) Provisional application No. 61/622,174, filed on Apr. 10, 2012.

(51) Int. Cl.
| C07K 14/435 | (2006.01) |
| C12Q 1/68 | (2018.01) |
| C12Q 1/6869 | (2018.01) |
| G01N 27/447 | (2006.01) |

(52) U.S. Cl.
CPC ..... *C07K 14/43536* (2013.01); *G01N 27/447* (2013.01); *C07K 2319/55* (2013.01); *C12Q 1/6869* (2013.01)

(58) Field of Classification Search
None
See application file for complete search history.

(56) References Cited

U.S. PATENT DOCUMENTS

| 5,795,782 A | 8/1998 | Church et al. |
| 6,015,714 A | 1/2000 | Baldarelli et al. |
| 6,114,121 A | 9/2000 | Fujiwara et al. |
| 6,150,112 A | 11/2000 | Weissman et al. |
| 6,362,002 B1 | 3/2002 | Denison et al. |
| 6,426,231 B1 | 7/2002 | Bayley et al. |
| 6,627,067 B1 | 9/2003 | Branton et al. |
| 6,824,659 B2 | 11/2004 | Bayley et al. |
| 6,863,833 B1 | 3/2005 | Bloom et al. |
| 6,916,665 B2 | 7/2005 | Bayley et al. |
| 6,927,070 B1 | 8/2005 | Bayley et al. |
| 7,189,503 B2 | 3/2007 | Akeson et al. |
| 8,105,846 B2 | 1/2012 | Bayley et al. |
| 8,785,211 B2 | 7/2014 | Bayley et al. |
| 8,822,160 B2 | 9/2014 | Bayley et al. |
| 8,828,208 B2 | 9/2014 | Canas et al. |
| 9,073,990 B2 | 7/2015 | Paas et al. |
| 9,127,313 B2 | 9/2015 | Brown et al. |
| 9,222,082 B2 | 12/2015 | Jayasinghe et al. |
| 9,447,152 B2 | 9/2016 | Clarke et al. |
| 9,562,887 B2 | 2/2017 | Maglia et al. |
| 9,580,480 B2 | 2/2017 | Lu et al. |
| 9,588,079 B2 | 3/2017 | Gundlach et al. |
| 9,732,381 B2 | 8/2017 | Stoddart et al. |
| 9,751,915 B2 | 9/2017 | Clarke et al. |
| 9,777,049 B2 | 10/2017 | Bruce et al. |
| 10,006,905 B2 | 6/2018 | Maglia et al. |
| 10,167,503 B2 | 1/2019 | Clarke et al. |
| 10,266,885 B2 | 4/2019 | Jayasinghe et al. |
| 10,385,389 B2 | 8/2019 | Heron et al. |
| 10,400,014 B2 | 9/2019 | Howorka et al. |
| 10,443,097 B2 | 10/2019 | Jayasinghe et al. |
| 10,472,673 B2 | 11/2019 | Maglia et al. |
| 10,514,378 B2 | 12/2019 | Maglia et al. |
| 10,669,581 B2 | 6/2020 | Stoddart et al. |
| 10,802,015 B2 | 10/2020 | Maglia et al. |
| 10,844,432 B2 | 11/2020 | Jayasinghe et al. |
| 10,882,889 B2 | 1/2021 | Bruce et al. |
| 10,975,428 B2 | 4/2021 | Jayasinghe et al. |
| 10,976,300 B2 | 4/2021 | Maglia et al. |
| 10,976,311 B2 | 4/2021 | Maglia et al. |
| 10,995,372 B2 | 5/2021 | Jayasinghe et al. |
| 11,021,747 B2 | 6/2021 | Garalde et al. |
| 11,034,734 B2 | 6/2021 | Howorka et al. |
| 11,104,709 B2 | 8/2021 | Maglia et al. |
| 11,169,138 B2 | 11/2021 | Maglia et al. |
| 11,186,868 B2 | 11/2021 | Jayasinghe et al. |
| 11,307,192 B2 | 4/2022 | Jayasinghe et al. |
| 11,572,387 B2 | 2/2023 | Remaut et al. |
| 11,597,970 B2 | 3/2023 | Jayasinghe et al. |
| 11,685,949 B2 | 6/2023 | Jayasinghe et al. |
| 11,725,235 B2 | 8/2023 | Heron et al. |
| 11,739,377 B2 | 8/2023 | Jayasinghe et al. |
| 11,761,956 B2 | 9/2023 | Maglia et al. |
| 11,845,780 B2 | 12/2023 | Bruce et al. |

FOREIGN PATENT DOCUMENTS

| CA | 2381139 A1 | 3/2001 |
| CN | 102116783 A | 7/2011 |

(Continued)

OTHER PUBLICATIONS

International Search Report and Written Opinion for Application No. PCT/GB2013/050667, mailed Jun. 27, 2013.

(Continued)

*Primary Examiner* — Marsha Tsay
(74) *Attorney, Agent, or Firm* — Wolf, Greenfield & Sacks, P.C.

(57) ABSTRACT

The invention relates to mutant forms of lysenin. The invention also relates to analyte characterisation using lysenin.

20 Claims, 12 Drawing Sheets

Specification includes a Sequence Listing.

(56) References Cited

U.S. PATENT DOCUMENTS

| | | |
|---|---|---|
| 11,939,359 B2 | 3/2024 | Jayasinghe et al. |
| 11,945,840 B2 | 4/2024 | Remaut et al. |
| 12,018,326 B2 | 6/2024 | Jayasinghe et al. |
| 12,024,541 B2 | 7/2024 | Remaut et al. |
| 12,084,477 B2 | 9/2024 | Remaut et al. |
| 2001/0044137 A1 | 11/2001 | Heyman et al. |
| 2002/0028458 A1 | 3/2002 | Lexow |
| 2002/0094526 A1 | 7/2002 | Bayley et al. |
| 2002/0197614 A1 | 12/2002 | Mosaic |
| 2003/0044816 A1 | 3/2003 | Denison et al. |
| 2003/0099951 A1 | 5/2003 | Akeson et al. |
| 2003/0165936 A1 | 9/2003 | Rabbani et al. |
| 2003/0211502 A1 | 11/2003 | Sauer et al. |
| 2003/0215881 A1 | 11/2003 | Bayley et al. |
| 2004/0209299 A1 | 10/2004 | Pinter et al. |
| 2004/0214177 A1 | 10/2004 | Bension |
| 2005/0053961 A1 | 3/2005 | Akeson et al. |
| 2006/0063171 A1 | 3/2006 | Akeson et al. |
| 2006/0105461 A1 | 5/2006 | Tom-Moy et al. |
| 2007/0218471 A1 | 9/2007 | Kim et al. |
| 2008/0121534 A1 | 5/2008 | White et al. |
| 2008/0311582 A1 | 12/2008 | Bayley et al. |
| 2009/0111115 A1 | 4/2009 | Drmanac et al. |
| 2009/0256116 A1 | 10/2009 | Shumaker-Parry et al. |
| 2009/0283412 A1 | 11/2009 | Sansinena et al. |
| 2009/0298075 A1 | 12/2009 | Travers et al. |
| 2009/0298188 A1 | 12/2009 | Peti-Peterdi |
| 2010/0075328 A1 | 3/2010 | Bjornson et al. |
| 2010/0120098 A1 | 5/2010 | Grunenwald et al. |
| 2010/0196203 A1 | 8/2010 | Sanghera et al. |
| 2010/0297638 A1 | 11/2010 | Bayley et al. |
| 2011/0120871 A1 | 5/2011 | Reid et al. |
| 2011/0121840 A1 | 5/2011 | Sanghera et al. |
| 2011/0177498 A1 | 7/2011 | Clarke et al. |
| 2011/0229877 A1 | 9/2011 | Jayasinghe et al. |
| 2011/0311965 A1 | 12/2011 | Maglia et al. |
| 2012/0058468 A1 | 3/2012 | Mckeown |
| 2012/0064599 A1 | 3/2012 | Jayasinghe et al. |
| 2012/0100530 A1 | 4/2012 | Moysey et al. |
| 2012/0107802 A1 | 5/2012 | Stoddart et al. |
| 2012/0322679 A1 | 12/2012 | Brown et al. |
| 2014/0051069 A1 | 2/2014 | Jayasinghe et al. |
| 2014/0186823 A1 | 7/2014 | Clarke et al. |
| 2014/0194324 A1 | 7/2014 | Gormley et al. |
| 2014/0262784 A1 | 9/2014 | Clarke et al. |
| 2014/0296083 A1 | 10/2014 | Brown et al. |
| 2015/0008126 A1 | 1/2015 | Maglia et al. |
| 2015/0031020 A1 | 1/2015 | Jayasinghe et al. |
| 2015/0068904 A1 | 3/2015 | Bruce et al. |
| 2015/0152495 A1 | 6/2015 | Stava et al. |
| 2015/0175663 A1 | 6/2015 | Yokoi et al. |
| 2015/0177237 A1 | 6/2015 | Turner et al. |
| 2015/0191709 A1 | 7/2015 | Heron et al. |
| 2015/0218629 A1 | 8/2015 | Heron et al. |
| 2015/0346149 A1 | 12/2015 | Brown et al. |
| 2016/0010147 A1 | 1/2016 | Heron et al. |
| 2016/0053300 A1 | 2/2016 | Maglia et al. |
| 2016/0370358 A1 | 12/2016 | Maglia et al. |
| 2017/0058337 A1 | 3/2017 | Clarke et al. |
| 2017/0058338 A1 | 3/2017 | Jayasinghe et al. |
| 2017/0107569 A1 | 4/2017 | Heron et al. |
| 2017/0233803 A1 | 8/2017 | Stoddart et al. |
| 2017/0306398 A1 | 10/2017 | Jayasinghe et al. |
| 2018/0030526 A1 | 2/2018 | Brown et al. |
| 2018/0095066 A1 | 4/2018 | Jayasinghe et al. |
| 2018/0148481 A2 | 5/2018 | Howorka et al. |
| 2018/0208632 A1 | 7/2018 | Bruce et al. |
| 2018/0209952 A1 | 7/2018 | Maglia et al. |
| 2018/0334707 A1 | 11/2018 | Stoddart et al. |
| 2018/0335425 A1 | 11/2018 | Maglia et al. |
| 2018/0364214 A1 | 12/2018 | Maglia et al. |
| 2019/0071721 A1 | 3/2019 | Jayasinghe et al. |
| 2019/0202876 A1 | 7/2019 | Jayasinghe et al. |
| 2019/0300582 A1 | 10/2019 | Jayasinghe et al. |
| 2019/0330282 A1 | 10/2019 | Jayasinghe et al. |
| 2019/0346431 A1 | 11/2019 | Maglia et al. |
| 2020/0017556 A1 | 1/2020 | Howorka et al. |
| 2020/0072824 A1 | 3/2020 | Maglia et al. |
| 2020/0087724 A1 | 3/2020 | Heron et al. |
| 2020/0224262 A1 | 7/2020 | Jayasinghe et al. |
| 2020/0299336 A9 | 9/2020 | Jayasinghe et al. |
| 2020/0299337 A9 | 9/2020 | Jayasinghe et al. |
| 2020/0407785 A1 | 12/2020 | Stoddart et al. |
| 2021/0139972 A1 | 5/2021 | Jayasinghe et al. |
| 2021/0147486 A1 | 5/2021 | Remaut et al. |
| 2021/0147490 A1 | 5/2021 | Remaut et al. |
| 2021/0269872 A1 | 9/2021 | Jayasinghe et al. |
| 2021/0284696 A1 | 9/2021 | Remaut et al. |
| 2021/0292376 A1 | 9/2021 | Howorka et al. |
| 2021/0317520 A1 | 10/2021 | Jayasinghe et al. |
| 2021/0324020 A1 | 10/2021 | Bruce et al. |
| 2021/0395811 A1 | 12/2021 | Garalde et al. |
| 2021/0405039 A1 | 12/2021 | Maglia et al. |
| 2022/0024985 A9 | 1/2022 | Remaut et al. |
| 2022/0056517 A1 | 2/2022 | Remaut et al. |
| 2022/0064230 A1 | 3/2022 | Jayasinghe et al. |
| 2022/0091096 A1 | 3/2022 | Maglia et al. |
| 2022/0119879 A1 | 4/2022 | Jayasinghe et al. |
| 2022/0154269 A9 | 5/2022 | Jayasinghe et al. |
| 2022/0162264 A9 | 5/2022 | Remaut et al. |
| 2022/0283141 A1 | 9/2022 | Jayasinghe et al. |
| 2023/0079731 A1 | 3/2023 | Remaut et al. |
| 2023/0295715 A1 | 9/2023 | Jayasinghe et al. |
| 2024/0026441 A1 | 1/2024 | Heron et al. |
| 2024/0044881 A1 | 2/2024 | Maglia et al. |
| 2024/0060126 A1 | 2/2024 | Jayasinghe et al. |
| 2024/0117422 A1 | 4/2024 | Jayasinghe et al. |
| 2024/0254172 A1 | 8/2024 | Maglia et al. |

FOREIGN PATENT DOCUMENTS

| | | |
|---|---|---|
| CN | 102174554 A | 9/2011 |
| CN | 102216783 A | 10/2011 |
| CN | 102317310 A | 1/2012 |
| CN | 103460040 A | 12/2013 |
| CN | 102245760 A | 5/2014 |
| EP | 2194123 B1 | 8/2012 |
| EP | 2682460 | 1/2014 |
| GB | 2453377 | 4/2009 |
| GB | 1314695.6 | 8/2013 |
| JP | H10-146190 | 6/1998 |
| JP | 2005-253427 | 9/2005 |
| JP | 2015-514128 A | 5/2015 |
| WO | WO 1999/005167 | 2/1999 |
| WO | WO 2000/028312 A1 | 5/2000 |
| WO | WO 2001/042782 | 6/2001 |
| WO | WO 2001/059453 | 8/2001 |
| WO | WO 2002/042496 | 5/2002 |
| WO | WO 2003/095669 | 11/2003 |
| WO | WO 2005/013666 A2 | 2/2005 |
| WO | WO 2005/076010 A2 | 8/2005 |
| WO | WO 2006/028508 | 3/2006 |
| WO | WO 2006/100484 | 9/2006 |
| WO | WO 2007/057668 | 5/2007 |
| WO | WO 2007/075987 | 7/2007 |
| WO | WO 2007/084103 | 7/2007 |
| WO | WO 2007/119880 A1 | 10/2007 |
| WO | WO 2008/102120 | 8/2008 |
| WO | WO 2008/102121 | 8/2008 |
| WO | WO 2008/124107 | 10/2008 |
| WO | WO 2009/024775 A1 | 2/2009 |
| WO | WO 2009/035647 | 3/2009 |
| WO | WO 2009/044170 A1 | 4/2009 |
| WO | WO 2009/077734 A2 | 6/2009 |
| WO | WO 2009/143425 A1 | 11/2009 |
| WO | WO 2010/004265 A1 | 1/2010 |
| WO | WO 2010/004273 A1 | 1/2010 |
| WO | WO 2010/034018 | 3/2010 |
| WO | WO 2010/055307 A1 | 5/2010 |
| WO | WO 2010/086602 A1 | 8/2010 |
| WO | WO 2010/086603 A1 | 8/2010 |
| WO | WO 2010/086622 A1 | 8/2010 |
| WO | WO 2010/122293 A1 | 10/2010 |

(56) References Cited

FOREIGN PATENT DOCUMENTS

| | | |
|---|---|---|
| WO | WO 2011/067559 A1 | 6/2011 |
| WO | WO 2012/042226 A1 | 4/2012 |
| WO | WO 2012/107778 A2 | 8/2012 |
| WO | WO 2012/164270 A1 | 12/2012 |
| WO | WO 2013/014451 A1 | 1/2013 |
| WO | WO 2013/041878 A1 | 3/2013 |
| WO | WO 2013/057495 A1 | 4/2013 |
| WO | WO 2013/098561 A1 | 7/2013 |
| WO | WO 2013/098562 A1 | 7/2013 |
| WO | WO 2013/109970 A1 | 7/2013 |
| WO | WO 2013/153359 A1 | 10/2013 |
| WO | WO 2014/078489 A1 | 10/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/064443 A1 | 5/2014 |
| WO | WO 2014/064444 A1 | 5/2014 |
| WO | WO 2014/122654 A2 | 8/2014 |
| WO | WO 2014/135838 A1 | 9/2014 |
| WO | WO 2014/142850 A1 | 9/2014 |
| WO | WO 2014/153047 A1 | 9/2014 |
| WO | WO 2014/153625 A1 | 10/2014 |
| WO | WO 2014/187924 A1 | 11/2014 |
| WO | WO 2015/022544 A1 | 2/2015 |
| WO | WO 2015/051378 A1 | 4/2015 |
| WO | WO 2015/055981 A1 | 4/2015 |
| WO | WO 2015/097289 A1 | 7/2015 |
| WO | WO 2015/110777 A1 | 7/2015 |
| WO | WO 2015/124935 A1 | 8/2015 |
| WO | WO 2015/150786 A1 | 10/2015 |
| WO | WO 2015/150787 A1 | 10/2015 |
| WO | WO 2015/166275 A1 | 11/2015 |
| WO | WO 2015/166276 A1 | 11/2015 |
| WO | WO 2016/034591 A2 | 3/2016 |
| WO | WO 2016/055778 A1 | 4/2016 |
| WO | WO 2016/166232 A1 | 10/2016 |
| WO | WO 2017/149316 A1 | 9/2017 |
| WO | WO 2017/149317 A1 | 9/2017 |
| WO | WO 2017/149318 A1 | 9/2017 |
| WO | WO 2018/211241 A1 | 11/2018 |

OTHER PUBLICATIONS

International Preliminary Report on Patentability for Application No. PCT/GB2013/050667, mailed Oct. 14, 2014.
[No Author Listed] EBI Accession No. GSP:AXX09397. May 13, 2010.
[No Author Listed] EBI Accession No. A0A085GH19. Oct. 29, 2014.
[No Author Listed] EBI Accession No. A0A0D1LDB9. Apr. 29, 2015.
[No Author Listed] EBI Accession No. EMBLCDS:ABV05494. Sep. 11, 2007.
[No Author Listed] Enterobacteria phage vB_EcoM-ACG-C40, complete genome. Genbank Acc. No. NC 019399.1. 2 pages. [97 pages in 70046US02].
[No Author Listed] Helicos BioSciences Corporation, "Helicos Genetic Analysis System," Specification Sheet retrieved online at: www.helicosbio.com/Portals/O/Documents/Helicos_SalesSpec.pdf, 4 pages (2008).
[No Author Listed] NCBI Genbank Accession No. ABV05494. Jan. 31, 2014, 1 page.
[No Author Listed] Nextera™ DNA Sample Preparation Kits (Illumina) Oct. 2011. (2 pages).
[No Author Listed] Oxford Nanopore "Product" brochure (2020) https://nanoporetech.com/sites/default/files/s3/literature/product-brochure.Pdf (36 pages).
[No Author Listed] Protein Databank entries of AlphaFold structure prediction for POAE98 and POA202, 2 pages.
[No Author Listed] Uniprot Accession No. POAE98 and POA202 search results, last accessed Mar. 29, 2022. 4 pages.
[No Author Listed] Uniprot Accession No. Q8Z727. Oct. 24, 2003. 4 pages.
[No Author Listed] UniProt, "SubName: Full=Curli production assembly/transport component {ECO:0000313:EMBL:CTR43957.1};", XP002783536, retrieved from EBI accession No. UniProt:A0A0K3UZP3, Nov. 11, 2015.
[No Author Listed] UniprotKB Accession No. N2DXI0, Jun. 26, 2013, 1 page.
[No Author Listed], *Escherichia coli* HS curli production assembly/transport subunit. Accession No. ABV05494. Sep. 11, 2007. 2 pages.
Afonine et al., Real-space refinement in PHENIX for cryo-EM and crystallography. Acta Crystallogr D Struct Biol. 2018;74(Pt 6):531-544. doi:10.1107/S2059798318006551.
Ahern, Biochemical, reagents kits offer scientists good return on investment. The Scientist. Jul. 24, 1995;9(15):20.
Akeson et al., Microsecond time-scale discrimination among polycytidylic acid, polyadenylic acid, and polyuridylic acid as homopolymers or as segments within single RNA molecules. Biophys J. Dec. 1999;77(6):3227-33.
Altschul et al. Basic local alignment search tool. J Mol Biol. Oct. 5, 1990;215(3):403-10. doi: 10.1016/S0022-2836(05)80360-2.
Altschul, A protein alignment scoring system sensitive at all evolutionary distances. J Mol Evol. Mar. 1993;36(3):290-300. doi: 10.1007/BF00160485.
Aoki et al., Single channel properties of lysenin measured in artificial lipid bilayers and their applications to biomolecule detection. Proc Jpn Acad Ser B Phys Biol Sci. 2010;86(9):920-5.
Aravind et al., The DNA-Repair Protein AlkB, EGL-9, and Leprecan Define New Families of 2-oxoglutarate-andIron-Dependent Dioxygenases. Genome Biology. 2001;2:1-8.
Ashkenasy et al., Recognizing a single base in an individual DNA strand: a step toward DNA sequencing in nanopores. Angew Chem Int Ed Engl. Feb. 18, 2005;44(9):1401-4.
Ashkenasy et al., Single Nucleobase Sensitivity of a-Hemolysin (a-HL) Transmembrane Protein Pore: Toward Single DNA Sequencing. ACS National Meeting. 2005;45(13), Abstract No. 74.
Ashton et al., MinION Nanopore Sequencing Identifies the Position and Structure of a Bacterial antibiotic Resistance Island. Nat Biotechnol. Mar. 2015;33(3):296-302.
Astier et al., Stochastic detection of motor protein-RNA complexes by single-channel current recording. Chemphyschem. Oct. 22, 2007;8(15):2189-94.
Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.
Atkins et al., Structure-function relationships of a novel bacterial toxin, hemolysin E. The role of alpha G. J Biol Chem. Dec. 29, 2000;275(52):41150-5.
Avrameas, Coupling of enzymes to proteins with glutaraldehyde. Use of the conjugates for the detection of antigens and antibodies. Immunochemistry. Jan. 1969;6(1):43-52.
Ayub et al., Engineered transmembrane pores. Curr Opin Chem Biol. 2016;34:117-126. doi:10.1016/j.cbpa.2016.08.005. Author Manuscript, 16 pages.
Bayley et al., Stochastic sensors inspired by biology. Nature. Sep. 13, 2001;413(6852):226-30.
Bayley et al., Wrestling with native chemical ligation. ACS Chem Biol. Dec. 18, 2009;4(12):983-5. doi: 10.1021/cb900304p.
Bayley, Membrane-protein structure: Piercing insights. Nature. Jun. 4, 2009;459(7247):651-2. doi: 10.1038/459651a.
Bayley, Nanopore Sequencing: From Imagination to Reality. Clin Chem. 2015;61(1):25-31.
Bayley, Sequencing single molecules of DNA. Curr Opin Chem Biol. Dec. 2006;10(6):628-37. Epub Nov. 20, 2006.
Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.
Bezrukov et al., Counting Polymers Moving Through a Single Ion Channel. Nature. Jul. 28, 1994;370:279-81.

(56) References Cited

OTHER PUBLICATIONS

Bianco et al., Helicase unwinding: active or merely perfect? J Mol Biol. Jul. 13, 2012;420(3):139-40. doi: 10.1016/j.jmb.2012.04.030. Epub May 2, 2012.
Bleijlevens et al., Changes in Protein Dynamics of the DNA Repair Dioxygenase AlkB Upon Binding of FE2+ and 2-Oxoglutarate. Biochemistry. Mar. 26, 2012;51:3334-41.
Bleijlevens et al., Dynamic States of the DNA Repair Enzyme AlkB regulate Product Release. Eur Mol Biol Org. Jul. 11, 2008;9(9):872-77.
Boersma et al., Continuous stochastic detection of amino acid enantiomers with a protein nanopore. Angew Chem Int Ed Engl. Sep. 17, 2012;51(38):9606-9. doi: 10.1002/anie.201205687. Epub Aug. 29, 2012.
Bourdon et al., Molecular cloning and sequence analysis of a chondroitin sulfate proteoglycan cDNA. Proc Natl Acad Sci U S A. Mar. 1985;82(5):1321-5.
Braha et al., Carriers versus adapters in stochastic sensing. Chemphyschem. May 2005;6(5):889-92.
Braha et al., Designed protein pores as components for biosensors. Chem Biol. Jul. 1997;4(7):497-505.
Branton et al., The potential and challenges of nanopore sequencing. Nat Biotechnol. Oct. 2008;26(10):1146-53. doi:10.1038/nbt.1495.
Braslavsky et al., Sequence information can be obtained from single DNA molecules. Proc Natl Acad Sci U S A. Apr. 1, 2003;100(7):3960-4. Epub Mar. 21, 2003.
Brown et al., Tools for macromolecular model building and refinement into electron cryo-microscopy reconstructions. Acta Crystallogr D Biol Crystallogr. 2015;71(Pt 1):136-153. doi:10.1107/S1399004714021683.
Burton et al., ClpX-mediated remodeling of mu transpososomes: selective unfolding of subunits destabilizes the entire complex. Mol Cell. Aug. 2001;8(2):449-54. doi: 10.1016/s1097-2765(01)00307-0.
Butler et al., Determination of RNA orientation during translocation through a biological nanopore. Biophys J. Jan. 1, 2006;90(1):190-9. Epub Oct. 7, 2005.
Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.
Byrd et al., Dda helicase tightly couples translocation on single-stranded DNA to unwinding of duplex DNA: Dda is an optimally active helicase. J Mol Biol. Jul. 13, 2012;420(3):141-54. doi: 10.1016/j.jmb.2012.04.007. Epub Apr. 11, 2012.
Cao et al., Structure of the nonameric bacterial amyloid secretion channel. Proc Natl Acad Sci USA. Dec. 16, 2014;111(50):E5439-44. doi: 10.1073/pnas.1411942111. Epub Dec. 1, 2014.
Caruccio, Preparation of next-generation sequencing libraries using Nextera™ technology: simultaneous DNA fragmentation and adaptor tagging by in vitro transposition. Methods Mol Biol. 2011;733:241-55. doi: 10.1007/978-1-61779-089-8_17.
Chan, Advances in sequencing technology. Mutat Res. Jun. 3, 2005;573(1-2):13-40.
Chapman et al., Role of *Escherichia coli* curli operons in directing amyloid fiber formation. Science. 2002;295(5556):851-855. doi:10.1126/science.1067484. Author Manuscript, 9 pages.
Cheley et al., A functional protein pore with a "retro" transmembrane domain. Protein Sci. Jun. 1999;8(6):1257-67.
Cheley et al., A genetically encoded pore for the stochastic detection of a protein kinase. Chembiochem. Dec. 2006;7(12):1923-7.
Cheley et al., Spontaneous oligomerization of a staphylococcal alpha-hemolysin conformationally constrained by removal of residues that form the transmembrane beta-barrel. Protein Eng. Dec. 1997;10(12):1433-43.
Chen et al., Atomic Layer Deposition to Fine-Tune the Surface Properties and Diameters of Fabricated Nanopores. Nano Lett. Jun. 25, 2004;4(7):1333-1337.
Chen et al., Outer membrane protein G: Engineering a quiet pore for biosensing. Proc Natl Acad Sci U S A. Apr. 29, 2008;105(17):6272-7. doi: 10.1073/pnas.0711561105. Epub Apr. 28, 2008.
Cheng et al., Design and testing of aptamer-based electrochemical biosensors for proteins and small molecules. Bioelectrochemistry. Nov. 2009;77(1):1-12. doi: 10.1016/j.bioelechem.2009.04.007. Epub May 5, 2009.
Chin et al., Addition of a photocrosslinking amino acid to the genetic code of *Escherichia coli*. Proc Natl Acad Sci U S A. Aug. 20, 2002;99(17):11020-4. doi: 10.1073/pnas.172226299. Epub Aug. 1, 2002.
Chin et al., The Metabolite alpha-Ketoglutarate Extends Lifespan by Inhibiting ATP Synthase and TOR. Nature. Jul. 19, 2014;510:397-401.
Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.
Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.
Comai et al., Protein engineering modulates the transport properties and ion selectivity of the pores formed by staphylococcal gamma-haemolysins in lipid membranes. Mol Microbiol. Jun. 2002;44(5):1251-67.
Dani et al., MspA Porin-Gold Nanoparticle Assemblies: Enhanced Binding through a Controlled Cysteine Mutation. Nano Lett. Apr. 2008;8(4):1229-36. doi: 10.1021/nl072658h. Epub Mar. 5, 2008.
De Vlaminck et al., Mechanism of homology recognition in DNA recombination from dual-molecule experiments. Mol Cell. Jun. 8, 2012;46(5):616-24. doi: 10.1016/j.molcel.2012.03.029. Epub May 3, 2012.
Deamer et al., Characterization of nucleic acids by nanopore analysis. Acc Chem Res. Oct. 2002;35(10):817-25.
Deamer et al., Nanopores and nucleic acids: prospects for ultrarapid sequencing. Trends Biotechnol. Apr. 2000;18(4):147-51.
Derrington et al., A Novel DNA Sensing Technique Using Nanopore MSPA. 54th Annual Meeting of the Biophysical Society, Poster 2182-Plat, 2 pages (2010).
Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.
Devereux et al., A comprehensive set of sequence analysis programs for the VAX. Nucleic Acids Res. Jan. 11, 1984;12(1 Pt 1):387-95. doi: 10.1093/nar/12.1part1.387.
Dong et al., Oroxylin A inhibits hemolysis via hindering the self-assembly of α-hemolysin heptameric transmembrane pore. PLoS Comput Biol. 2013;9(1):e1002869. doi: 10.1371/journal.pcbi.1002869. Epub Jan. 17, 2013.
Dorre et al., Techniques for single molecule sequencing. Bioimaging, vol. 5:139-152 (1997).
Eid et al., Real-time DNA sequencing from single polymerase molecules. Science. Jan. 2, 2009;323(5910):133-8. doi:10.1126/science.1162986. Epub Nov. 20, 2008.
Eifler et al., Cytotoxin ClyA from *Escherichia coli* assembles to a 13-meric pore independent of its redox-state. EMBO J. Jun. 7, 2006;25(11):2652-61. doi: 10.1038/sj.emboj.7601130. Epub May 11, 2006.
Eliseev et al., Aminocyclodextrins as Selective Hosts with Several Binding Sites for Nucleotides. Angew. Chem. Int. Ed. Engl., vol. 32(9):1331-1333 (1993).
Eliseev et al., Molecular Recognition of Nucleotides, Nucleosides, and Sugars by Aminocyclodextrins. J. Am. Chem. Soc., vol. 116:6081-6088 (1994).
Engelhardt et al., A tetrameric porin limits the cell wall permeability of *Mycobacterium smegmatis*. J Biol Chem. Oct. 4, 2002;277(40):37567-72. Epub Jul. 18, 2002.
Epstein, Assembly, Spatial Distribution, and Secretion Activity of the Curlin Secretion Lipoprotein, CsgG. Dissertation. The University of Michigan. 2008. 167 pages.
Ergel et al., Protein Dynamics Control the Progression and Efficiency of the Catalytic Reaction Cycle of the *Escherichia coli* DNA-Repair Enzyme AlkB. J Biol Chem. Oct. 24, 2014;289(43):29584-601.

(56) References Cited

OTHER PUBLICATIONS

Fahie et al., Resolved Single-Molecule Detection of Individual Species Within a Mixture of Anti-Biotin Antibodies Using an Engineered Monometric Nanopore. Am Chem Soc. Jan. 9, 2015;9(2):1089-98.

Fiaschi et al., Auto-Assembling Detoxified *Staphylococcus aureus* Alpha-Hemolysin Mimicking the Wild-Type Cytolytic Toxin. Clin Vaccine Immunol. Jun. 6, 2016;23(6):442-50. doi: 10.1128/CVI.00091-16.

Fiume et al., Savant: genome browser for high-throughput sequencing data. Bioinformatics. Aug. 15, 2010;26(16):1938-44. doi: 10.1093/bioinformatics/btq332. Epub Jun. 20, 2010.

Fleckenstein et al., "UPI0002CA1AFE" Uniprot Accession No. https://www.uniprot.org/uniparc/UPI0002CA1AFE, Jun. 26, 2013 (Jun. 26, 2013).

Flomenbom et al., Single stranded DNA translocation through a nanopore: a master equation approach. Phys Rev E Stat Nonlin Soft Matter Phys. Oct. 2003;68(4 Pt 1):041910. Epub Oct. 14, 2003.

Flusberg et al., Direct detection of DNA methylation during single-molecule, real-time sequencing. Nat Methods. Jun. 2010;7(6):461-5. doi: 10.1038/nmeth.1459. Epub May 9, 2010.

Fologea et al., Potential analytical applications of lysenin channels for detection of multivalent ions. Anal Bioanal Chem. Oct. 2011;401(6):1871-9. doi:10.1007/s00216-011-5277-8. Epub Aug. 5, 2011.

Franceschini et al., A nanopore machine promotes the vectorial transport of DNA across membranes. Sep. 2013; Nat Commun. 2013;4:2415. doi: 10.1038/ncomms3415.

Franceschini et al., DNA Translocation through Nanopores at Physiological Ionic Strengths Requires Precise Nanoscale Engineering. ACS Nano. Sep. 27, 2016;10(9):8394-402. doi: 10.1021/acsnano.6b03159. Epub Aug. 15, 2016.

Freedman et al., Single Molecule Unfolding and Stretching of Protein Domains Inside a Solid-State Nanopore by Electric Field. Scientific Reports. Apr. 10, 2013;3(1638):1-8.

Galenkamp et al., Direct electrical quantification of glucose and asparagine from bodily fluids using nanopores. Nat Commun. 2018;9(1):4085. Published Oct. 5, 2018. doi:10.1038/s41467-018-06534-1.

Genschel et al., Interaction of *E. coli* single-stranded DNA binding protein (SSB) with exonuclease I. The carboxy-terminus of SSB is the recognition site for the nuclease. Biol Chem. Mar. 2000;381(3):183-92.

Gershow et al., Recapturing and trapping single molecules with a solid-state nanopore. Nat Nanotechnol. Dec. 2007;2(12):775-9. doi:10.1038/nnano.2007.381. Epub Dec. 2, 2007.

Ghanem et al., Chimeric mutants of staphylococcal hemolysin, which act as both one-component and two-component hemolysin, created by grafting the stem domain. Febs J. Jun. 2022;289(12):3505-3520. doi: 10.1111/febs.16354. Epub Feb. 16, 2022.

Ghosal, Electrokinetic-flow-induced viscous drag on a tethered DNA inside a nanopore. Phys Rev E Stat Nonlin Soft Matter Phys. Dec. 2007;76(6 Pt 1):061916. Epub Dec. 26, 2007.

Gibson et al., AgfC and AgfE facilitate extracellular thin aggregative fimbriae synthesis in *Salmonella enteritidis*. Microbiology. Apr. 2007;153(Pt 4):1131-1140. doi: 10.1099/mic.0.2006/000935-0.

Gilbert et al., Two Structural Transitions in Membrane Pore Formation by Pneumolysin, the Pore-Forming Toxin of *Streptococcus pneumoniae*. Cell. May 28, 1999;97:647-655.

Goedhart et al., Quantitative co-expression of proteins at the single cell level—application to a multimeric FRET sensor. PLoS One. 2011;6(11):e27321. doi: 10.1371/journal.pone.0027321. Epub Nov. 17, 2011.

Goryshin et al., Tn5 in vitro transposition. J Biol Chem. Mar. 27, 1998;273(13):7367-74. doi: 10.1074/jbc.273.13.7367.

Gouridis et al., Conformational Dynamics in Substrate-Binding Domains Influences Transport in the ABC Importer GinPQ. Nat Stuct Mol Biol. Dec. 8, 2014;22(1):57-66.

Goyal et al., Crystallization and preliminary X-ray crystallographic analysis of the curli transporter CsgG. Acta Crystallographica Section F: Structural Biology and Crystallization Communications. Dec. 1, 2013;69(12):1349-53.

Goyal et al., Structural and mechanistic insights into the bacterial amyloid secretion channel CsgG. Nature. Dec. 11, 2014;516(7530):250-3 with Supplemental Information. doi: 10.1038/nature13768. Epub Sep. 14, 2014.

Gu et al., Capture of a single molecule in a nanocavity. Science. Jan. 26, 2001;291(5504):636-40.

Gu et al., Electroosmotic enhancement of the binding of a neutral molecule to a transmembrane pore. Proc Natl Acad Sci U S A. Dec. 23, 2003;100(26):15498-503. Epub Dec. 15, 2003.

Gu et al., Interaction of the noncovalent molecular adapter, beta-cyclodextrin, with the staphylococcal alpha-hemolysin pore. Biophys J. Oct. 2000;79(4):1967-75.

Gu et al., Prolonged residence time of a noncovalent molecular adapter, beta-cyclodextrin, within the lumen of mutant alpha-hemolysin pores. J Gen Physiol. Nov. 2001;118(5):481-94.

Gu et al., Reversal of charge selectivity in transmembrane protein pores by using noncovalent molecular adapters. Proc Natl Acad Sci U S A. Apr. 11, 2000;97(8):3959-64.

Gu et al., Stochastic sensing of organic analytes by a pore-forming protein containing a molecular adapter. Nature. Apr. 22, 1999;398(6729):686-90.

Guan et al., Stochastic sensing of TNT with a genetically engineered pore. Chembiochem. Oct. 2005;6(10):1875-81.

Guasch et al., Detailed architecture of a DNA translocating machine: the high-resolution structure of the bacteriophage phi29 connector particle. J Mol Biol. Jan. 25, 2002;315(4):663-76.

Guo et al., Nanopore sensor for copper ion detection using a polyamine decorated β-cyclodextrin as the recognition element. RSC Adv. 2017;7:15315. doi: 10.1039/c7ra00454k. 6 pages.

Hall et al., Hybrid pore formation by directed insertion of α-haemolysin into solid-state nanopores. Nat Nanotechnol. Dec. 2010;5(12):874-7. doi: 10.1038/nnano.2010.237. Epub Nov. 28, 2010.

Hammar et al., Expression of two csg operons is required for production of fibronectin- and congo red-binding curli polymers in *Escherichia coli* K-12. Mol Microbiol. Nov. 1995;18(4):661-70. doi: 10.1111/j.1365-2958.1995.mmi_18040661.x.

Han et al., Characterization and optimization of an entropic trap for DNA separation. Anal Chem. Jan. 15, 2002;74(2):394-401.

Han et al., RecJ exonuclease: substrates, products and interaction with SSB. Nucleic Acids Res. Feb. 18, 2006;34(4):1084-91. Print 2006.

Haque et al., DNA-associated click chemistry. Science China Chemistry. Feb. 2014;57(2):215-231. doi:10.1007/s11426-013-5035-1.

Haque et al., Solid-State and Biological Nanopore for Real-Time Sensing of Single Chemical and Sequencing of DNA. Nano Today. Feb. 2013;8(1):56-74.

He et al. 2012; The T4 phage SF1 B helicase dda is structurally optimized to perform DNA strand separation. Structure. 20:1189-1200.

Heng et al., Sizing DNA using a nanometer-diameter pore. Biophys J. Oct. 2004;87(4):2905-11. doi: 10.1529/biophysj.104.041814. Epub Aug. 23, 2004.

Henrickson et al., Driven DNA transport into an asymmetric nanometer-scale pore. Phys Rev Lett. Oct. 2, 2000;85(14):3057-60.

Heron et al., Direct detection of membrane channels from gels using water-in-oil droplet bilayers. J Am Chem Soc. Dec. 26, 2007;129(51):16042-7. Epub Dec. 1, 2007.

Higgins et al., DNA-joining enzymes: a review. Methods Enzymol. 1979;68:50-71. doi: 10.1016/0076-6879(79)68006-0.

Holden et al., Direct introduction of single protein channels and pores into lipid bilayers. J Am Chem Soc. May 11, 2005;127(18):6502-3.

Holden et al., Functional bionetworks from nanoliter water droplets. J Am Chem Soc. Jul. 11, 2007;129(27):8650-5. Epub Jun. 16, 2007.

Hornblower et al., Single-molecule analysis of DNA-protein complexes using nanopores. Nat Methods. Apr. 2007;4(4):315-7. Epub Mar. 4, 2007.

(56) References Cited

OTHER PUBLICATIONS

Howorka et al., DNA Duplex Formation of Individual DNA Strands within a Single Protein Pore. Biophysical Journal, vol. 82{ 1, pt. 2):508a, No. 2482-Plat (2002).

Howorka et al., Kinetics of duplex formation for individual DNA strands within a single protein nanopore. Proc Natl Acad Sci U S A. Nov. 6, 2001;98(23):12996-3001. Epub Oct. 23, 2001.

Howorka et al., Nanopore Analytics: Sensing of Single Molecules. The Royal Society of Chemistry. Jun. 15, 2009;38:2360-84.

Howorka et al., Nanopores as protein sensors. Nat Biotechnol. Jun. 7, 2012;30(6):506-7. doi: 10.1038/nbt.2264.

Howorka et al., Probing distance and electrical potential within a protein pore with tethered DNA. Biophys J. Dec. 2002;83(6):3202-10.

Howorka et al., Sequence-specific detection of individual DNA strands using engineered nanopores. Nat Biotechnol. Jul. 2001;19(7):636-9.

Hu et al., Theory of DNA translocation through narrow ion channels and nanopores with charged walls. Phys Rev E Stat Nonlin Soft Matter Phys. Sep. 2008;78(3 Pt 1):032901. Epub Sep. 10, 2008.

Huff et al., Functions of the periplasmic loop of the porin MspA from *Mycobacterium smegmatis*. J Biol Chem. Apr. 10, 2009;284(15):10223-31. doi: 10.1074/jbc.M808599200. Epub Feb. 10, 2009.

Hwang et al., Electrical behavior of droplet interface bilayer networks: experimental analysis and modeling. J Am Chem Soc. Sep. 26, 2007;129(38):11854-64. Epub Sep. 1, 2007.

Iacovache et al., Structure and assembly of pore-forming proteins. Curr Opin Struct Biol. Apr. 2010;20(2):241-6. doi:10.1016/j.sbi.2010.01.013. Epub Feb. 19, 2010.

Ide et al., Lysenin forms a voltage-dependent channel in artificial lipid bilayer membranes. Biochem Biophys Res Commun. Jul. 21, 2006;346(1):288-92. Epub May 26, 2006.

Ivanov et al., DNA tunneling detector embedded in a nanopore. Nano Lett. Jan. 12, 2011;11(1):279-85. doi: 10.1021/nl103873a. Epub Dec. 6, 2010.

Jain et al., The Oxford Nanopore MinION: delivery of nanopore sequencing to the genomics community. Genome Biol. Nov. 25, 2016;17(1):239. doi: 10.1186/s13059-016-1103-0. Erratum in: Genome Biol. Dec. 13, 2016;17 (1):256.

Jayasinghe et al., The leukocidin pore: evidence for an octamer with four LukF subunits and four LukS subunits alternating around a central axis. Protein Sci. Oct. 2005;14(10):2550-61.

Johnston et al., Coexpression of proteins in bacteria using T7-based expression plasmids: expression of heteromeric cell-cycle and transcriptional regulatory complexes. Protein Expr Purif. Dec. 2000;20(3):435-43.

Juncker et al., Prediction of lipoprotein signal peptides in Gram-negative bacteria. Protein Sci. 2003;12(8):1652-1662. doi:10.1110/ps.0303703.

Jung et al., The internal cavity of the staphylococcal alpha-hemolysin pore accommodates approximately 175 exogenous amino acid residues. Biochemistry. Jun. 28, 2005;44(25):8919-29.

Kalli et al., Conformational changes in talin on binding to anionic phospholipid membranes facilitate signaling by integrin transmembrane helices. PLoS Comput Biol. Oct. 2013;9(10):e1003316. doi:10.1371/journal.pcbi.1003316.

Kanaan et al., UPF1-like helicase grip on nucleic acids dictates processivity. Nat Commun. Sep. 14, 2018;9(1):3752. doi: 10.1038/s41467-018-06313-y.

Kang et al., Single protein pores containing molecular adapters at high temperatures. Angew Chem Int Ed Engl. Feb. 25, 2005;44(10):1495-9.

Kasianowicz et al., Characterization of individual polynucleotide molecules using a membrane channel. Proc Natl Acad Sci U S A. Nov. 26, 1996;93(24):13770-3.

Khulbe et al., DNA translocation through a-hemolysin nanopores with potential application to macromolecular data storage. Journal Applied Physics, vol. 97(104317):1-7 (2005).

Kimanius et al., Accelerated cryo-EM structure determination with parallelisation using GPUs in RELION-2. Elife. 2016;5:e18722. Published Nov. 15, 2016. doi:10.7554/eLife.18722. 21 pages.

Klenchin et al., Phosphate coordination and movement of DNA in the Tn5 synaptic complex: role of the (R)YREK motif. Nucleic Acids Res. Oct. 2008;36(18):5855-62. doi: 10.1093/nar/gkn577. Epub Sep. 12, 2008.

Kobayashi et al., Comparative Physiology and Biochemistry, 2005, vol. 22, No. 3-4, pp. 139-148.

Kolinko et al., Single-cell genomics reveals potential for magnetite and greigite biomineralization in an uncultivated multicellular magnetotactic prokaryote. Environ Microbiol Rep. Oct. 2014;6(5):524-31. doi: 10.1111/1758-2229.12198. Epub Aug. 28, 2014. Abstract Only.

Krylova et al., DNA aptamers for as analytical tools for the quantitative analysis of DNA-dealkylating enzymes. Anal Biochem. 2011;414(2):261-265. doi:10.1016/j.ab.2011.03.010.

Kumar et al., PEG-labeled nucleotides and nanopore detection for single molecule DNA sequencing by synthesis. Sci Rep. 2012;2:684. Epub Sep. 21, 2012.

Langecker et al., Synthetic lipid membrane channels formed by designed DNA nanostructures. Science. Nov. 16, 2012;338(6109):932-6. doi: 10.1126/science.1225624.

Le et al., Thermostable DNA ligase-mediated PCR production of circular plasmid (PPCP) and its application in directed evolution via in situ error-prone PCR. DNA Res. Aug. 2013;20(4):375-82. doi: 10.1093/dnares/dst016. Epub Apr. 30, 2013.

Li et al., ChIA-PET tool for comprehensive chromatin interaction analysis with paired-end tag sequencing. Genome Biol. 2010;11(2):R22. doi: 10.1186/gb-2010-11-2-r22. Epub Feb. 25, 2010.

Li et al., Different Anomeric Sugar Bound States of Maltose Binding Protein Resolved by a Cytolysin A Nanopore Tweezer. ACS Nano. 2020;14(2):1727-1737. doi:10.1021/acsnano.9b07385.

Li et al., DNA molecules and configurations in a solid-state nanopore microscope. Nat Mater. Sep. 2003;2(9):611-5. Epub Aug. 24, 2003.

Li, Minimap2: pairwise alignment for nucleotide sequences. Bioinformatics. 2018;34(18):3094-3100. doi:10.1093/bioinformatics/bty191.

Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.

Loferer et al., Availability of the fibre subunit CsgA and the nucleator protein CsgB during assembly of fibronectin-binding curli is limited by the intracellular concentration of the novel lipoprotein CsgG. Mol Microbiol. 1997;26(1):11-23. doi:10.1046/j.1365-2958.1997.5231883.x.

Lovett, The DNA Exonucleases of *Escherichia coli*. EcoSal Plus. Dec. 2011;4(2):10.1128/ecosalplus.4.4.7. doi: 10.1128/ecosalplus.4.4.7. Author Manuscript, 45 pages.

Lu et al., Expression, purification and structural analysis of csgF gene of curli systems from *Escherichia coli* CFT073. Microbiol China. 2016, 43(9):2063-2071. doi:10.13344/j.microbiol.china.150752.

Lu et al., Protein Motion and Configurations in a Form-Fitting Nanopore: Avidin in ClyA. Biophys J. Sep. 4, 2018; 115(5): 801-808. Epub Aug. 4, 2018. doi: 10.1016/j.bpj.2018.07.024.

Luchian et al., Single-Molecule Covalent Chemistry with Spatially Separated Reactants. Angew. Chem. Int. Ed. 2003;42:3766-771.

Ludtke, Single-Particle Refinement and Variability Analysis in EMAN2.1. Methods Enzymol. 2016;579:159-89. doi: 10.1016/bs.mie.2016.05.001. Epub Jul. 1, 2016.

Ludwig et al., Analysis of the SlyA-Controlled Expression, Subcellular Localization and Pore-Forming Activity of a 34 kDa Haemolysin (ClyA) from *Escherichia coli* K-12. Mol Microbiol. 1999;31(2):557-67.

Luo et al., Influence of polymer-pore interactions on translocation. Phys Rev Lett. Oct. 5, 2007;99(14):148102. Epub Oct. 1, 2007.

Maglia et al., DNA strands from denatured duplexes are translocated through engineered protein nanopores at alkaline pH. Nano Lett. Nov. 2009;9(11):3831-6. doi: 10.1021/nl9020232.

(56) References Cited

OTHER PUBLICATIONS

Maglia et al., Engineering a Biomimetic Biological Nanopore to Selectively Capture Folded Target Proteins. Biophysical J. Feb. 5, 2013;104(2):518a.

Maglia et al., Enhanced translocation of single DNA molecules through alpha-hemolysin nanopores by manipulation of internal charge. Proc Natl Acad Sci U S A. Dec. 16, 2008;105(50):19720-5. doi: 10.1073/pnas.0808296105. Epub Dec. 5, 2008.

Makaram et al., Trends in Nanomaterial-Based Non-Invasive Diabetes Sensing Technologies. Diagnostics. Apr. 21, 2014;4:27-46.

Manrao et al., Nucleotide Discrimination with DNA Immobilized in the MspA Nanopore. PLoS One, vol. 6(10):e25723, 7 pages (2011).

Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.

Manrao et al., Single Nucleotide Discrimination in Single Stranded DNA Immobilized within Biological Nanopre MSPA. 54th Annual Meeting of the Biophysical Society, 3 pages (2010).

Martin et al., Nanoscale protein pores modified with PAMAM dendrimers. J Am Chem Soc. Aug. 8, 2007;129(31):9640-9. Epub Jul. 18, 2007.

Marziali et al., New DNA sequencing methods. Annu Rev Biomed Eng. 2001;3:195-223.

Mathé et al., Orientation discrimination of single-stranded DNA inside the alpha-hemolysin membrane channel. Proc Natl Acad Sci U S A. Aug. 30, 2005;102(35):12377-82. Epub Aug. 19, 2005.

Matsuura et al., Real-time observation of a single DNA digestion by lambda exonuclease under a fluorescence microscope field. Nucleic Acids Res. Aug. 15, 2001;29(16):E79.

Meller et al., Rapid nanopore discrimination between single polynucleotide molecules. Proc Natl Acad Sci U S A. Feb. 1, 2000;97(3):1079-84.

Meller et al., Single molecule measurements of DNA transport through a nanopore. Electrophoresis. Aug. 2002;23(16):2583-91.

Meller, Dynamics of polynucleotide transport through nanometre-scale pores. Journal Physics: Condensed Matter, vol. 15:R581-R607 (2003).

Merzlyak et al., Conductance and ion selectivity of a mesoscopic protein nanopore probed with cysteine scanning mutagenesis. Biophys J. Nov. 2005;89(5):3059-70. Epub Aug. 5, 2005.

Mikheyev et al., A First Look at the Oxford Nanopore MinION Sequencer. Mol Ecol Res. 2014;14:1097-1102.

Miles et al., The Staphylococcal Leukocidin Bicomponent Toxin Forms Large Ionic Channels. Biochemistry. Jun. 28, 2001;40:8514-522.

Mitchell et al., Chemical tags facilitate the sensing of individual DNA strands with nanopores. Angew Chem Int Ed Engl. 2008;47(30):5565-8. doi:10.1002/anie.200800183.

Miyazaki et al., Megawhop Cloning: A Method of Creating Random Mutagenesis Libraries via Megaprimer PCR of Whole Plasmids. Methods in Enzymology. 2011;498:399-406.

Mohammad et al., Controlling a single protein in a nanopore through electrostatic traps. J Am Chem Soc. Mar. 26, 2008;130(12):4081-8. doi: 10.1021/ja710787a. Epub Mar. 6, 2008.

Moreau et al., Coupling ion channels to receptors for biomolecule sensing. Nat Nanotechnol. Oct. 2008;3(10):620-5. doi: 10.1038/nnano.2008.242. Epub Sep. 7, 2008.

Movileanu et al., Detecting protein analytes that modulate transmembrane movement of a polymer chain within a single protein pore. Nat Biotechnol. Oct. 2000;18(10):1091-5.

Movileanu et al., Location of a constriction in the lumen of a transmembrane pore by targeted covalent attachment of polymer molecules. J Gen Physiol. Mar. 2001;117(3):239-52.

Moyer et al., Correlation Between Sweat Glucose and Blood Glucose in Subjects with Diabetes. Diabetes Technol Ther. 2012:14(5):398-402.

Mueller et al., RCSB Protein Data Bank No. 2WCD. Mar. 11, 2009. doi: 10.2210/pdb2WCD/pdb. 5 pages.

Mueller et al., The Structure of Cytolytic alpha-Helical Toxin Pore Reveals its Assembly Mechanism. Nature. Jun. 4, 2009;459:726-731.

Mueller et al., The Structure of Cytolytic alpha-Helical Toxin Pore Reveals its Assembly Mechanism. Nature. Jun. 4, 2009;459:Supplemental Information.

Muller et al., DNA-directed assembly of artificial multienzyme complexes. Biochem Biophys Res Commun. Dec. 5, 2008;377(1):62-7. doi:10.1016/j.bbrc.2008.09.078. Epub Sep. 25, 2008.

Mund et al., LEGO-NMR spectroscopy: a method to visualize individual subunits in large heteromeric complexes. Angew Chem Int Ed Engl. Oct. 18, 2013;52(43):11401-5. doi: 10.1002/anie.201304914. Epub Aug. 14, 2013.

Nakane et al., A nanosensor for transmembrane capture and identification of single nucleic Acid molecules. Biophys J. Jul. 2004;87(1):615-21. Erratum in: Biophys J. Nov. 2004;87(5):3618.

Nakane et al., Nanopore sensors for nucleic acid analysis. J. Phys.: Condens. Matter, vol. 15: R 1365- R1393 (2003).

Niedzwiecki et al., Inspection of the Engineered FhuA deltaC/delta4L Protein Nanopore by Polymer Exclusion. Biophys J. Nov. 2012;103:2115-124.

Nikolaidou et al., alpha-Ketoglutarate: Biological Effects of a Novel Biomarker of Heart Failure. Heart. Sep. 2010;96(17). 2 pages.

Nivala et al., Unfoldase-mediated protein translocation through an $\alpha$-hemolysin nanopore. Nat Biotechnol. Mar. 2013;31(3):247-50. doi: 10.1038/nbt.2503. Epub Feb. 3, 2013. Author Manuscript, 10 pages.

Ogasawara et al., Determination of Reduced Nicotinamide Adenine Dinucleotid Phosphate Concentration Using High-Performance Liquid Chromatography with Fluorescence Detection: Ratio of the Reduced Form as a Biomarker of Oxidative Stress. Biol Pharm Bull. Nov. 2009;32(11):1819-18223.

Oukhaled et al., Dynamics of Completely Unfolded and Native Proteins through Solid-State Nanopores as a Function of Electric Driving Force. Am Chem Soc. 2011 Arp 8;5(5):3628-38.

Pavlenok et al., Hetero-oligomeric MspA pores in *Mycobacterium smegmatis*. FEMS Microbiol Lett. Apr. 2016;363(7). pii: fnw046. doi:10.1093/femsle/fnw046. Epub Feb. 23, 2016.

Pavlenok et al., MspA nanopores from subunit dimers. PLoS One. 2012;7(6):e38726. doi: 10.1371/journal.pone.0038726. Epub Jun. 18, 2012.

Peabody et al., Type II protein secretion and its relationship to bacterial type IV pili and archaeal flagella. Microbiology. Nov. 2003;149(Pt 11):3051-3072. doi: 10.1099/mic.0.26364-0.

Pfeiffer et al., Bivalent cholesterol-based coupling of oligonucleotides to lipid membrane assemblies. J Am Chem Soc. Aug. 25, 2004;126(33):10224-5.

Plesa et al., Fast Translocation of Proteins through Solid State Nanopores. Nano Lett. Jan. 23, 2013:13:658-663.

Pud et al., Mechanical Trapping of DNA in a Double-Nanopore System. Nano Lett. 2016;16(12):8021-8028. doi:10.1021/acs.nanolett.6b04642. Author Manuscript, 17 pages.

Purnell et al., Nucleotide identification and orientation discrimination of DNA homopolymers immobilized in a protein nanopore. Nano Lett. Sep. 2008;8(9):3029-34. doi: 10.1021/nl802312f. Epub Aug. 13, 2008.

Quick et al., A reference Bacterial Genome Dataset Generated on the MinION Portable Single-Molecule Nanopore Sequencer. GigaScience. 2014;3(22):1-6.

Rajagopalan et al., Interaction of Dihydrofolate Reductase with Methotrexate: Ensemble and Single-Molecule Kinetics. PNAS. Oct. 15, 2002:99(21):13481-6.

Rasko et al., The pangenome structure of *Escherichia coli*: comparative genomic analysis of *E. coli* commensal and pathogenic isolates. J Bacteriol. Oct. 2008;190(20):6881-93. doi:10.1128/JB.00619-08. Epub Aug. 1, 2008.

Reznikoff, Tn5 as a model for understanding DNA transposition. Mol Microbiol. Mar. 2003;47(5):1199-206. doi: 10.1046/j.1365-2958.2003.03382.x.

Rhee et al., Comprehensive genome-wide protein-DNA interactions detected at single-nucleotide resolution. Cell. Dec. 9, 2011;147(6):1408-19. doi: 10.1016/j.cell.2011.11.013.

(56) References Cited

OTHER PUBLICATIONS

Rhee et al., Nanopore sequencing technology: research trends and applications. Trends Biotechnol. Dec. 2006;24(12):580-6. Epub Oct. 19, 2006.
Robinson et al., Secretion of curli fibre subunits is mediated by the outer membrane-localized CsgG protein. Mol Microbiol. Feb. 2006;59(3):870-81. doi: 10.1111/j.1365-2958.2005.04997.x.
Rodriguez-Gallego et al., Mapping of the Circulating Metabolome Reveals alpha-Ketoglutarate as a Predictor of Morbid Obesity-Associated Non-Alcoholic Fatty Liver Disease. Int J of Obesity. 2015;39:279-287.
Rohou et al., CTFFIND4: Fast and accurate defocus estimation from electron micrographs. J Struct Biol. Nov. 2015;192(2):216-21. doi: 10.1016/j.jsb.2015.08.008. Epub Aug. 13, 2015.
Rotem et al., Protein detection by nanopores equipped with aptamers. J Am Chem Soc. Feb. 8, 2012;134(5):2781-7. doi:10.1021/ja2105653. Epub Jan. 26, 2012.
Rucker et al., Recombinant ferritin: modulation of subunit stoichiometry in bacterial expression systems. Protein Eng. 1997;10(8):967-973. doi: 10.1093/protein/10.8.967.
Russo et al., Reversible permeabilization of plasma membranes with an engineered switchable pore. Nat Biotechnol. Mar. 1997;15(3):278-82.
Saariaho et al., Characteristics of MuA transposase-catalyzed processing of model transposon end DNA hairpin substrates. Nucleic Acids Res. Jun. 6, 2006;34(10):3139-49.
Sanchez-Quesada et al., Cyclic Peptides as Molecular Adapters for a Pore-Forming Protein. Journal American Chemical Society, vol. 122(48):11757-11766 (2000).
Sanchez-Quesada et al., Single DNA rotaxanes of a transmembrane pore protein. Angew Chem Int Ed Engl. Jun. 7, 2004;43(23):3063-7.
Sanderson, Personal genomes: Standard and pores. Nature. Nov. 6, 2008;456(7218):23-5. doi: 10.1038/456023a.
Sauer-Budge et al., Unzipping kinetics of double-stranded DNA in a nanopore. Phys Rev Lett. Jun. 13, 2003;90(23):238101. Epub Jun. 9, 2003.
Scheres, Relion: implementation of a Bayesian approach to cryo-EM structure determination. J Struct Biol. Dec. 2012;180(3):519-30. doi: 10.1016/j.jsb.2012.09.006. Epub Sep. 19, 2012.
Shelbourne et al., Fast copper-free click DNA ligation by the ring-strain promoted alkyne-azide cycloaddition reaction. Chem Commun (Camb). Jun. 14, 2011;47(22):6257-9. doi: 10.1039/c1cc10743g. Epub May 6, 2011.
Sivanathan et al., Generating extracellular amyloid aggregates using *E. coli* cells. Genes Dev. Dec. 1, 2012;26(23):2659-67. doi: 10.1101/gad.205310.112. Epub Nov. 19, 2012.
Skocaj et al., The sensing of membrane microdomains based on pore-forming toxins. Curr Med Chem. 2013;20(4):491-501.
Smeets et al., Salt dependence of ion transport and DNA translocation through solid-state nanopores. Nano Lett. Jan. 2006;6(1):89-95.
Soni et al., Synchronous optical and electrical detection of biomolecules traversing through solid-state nanopores. Rev Sci Instrum. Jan. 2010;81(1):014301. doi: 10.1063/1.3277116.
Soskine et al., An engineered ClyA nanopore detects folded target proteins by selective external association and pore entry. Nano Lett. Sep. 12, 2012;12(9):4895-900. doi:10.1021/nl3024438. Epub Aug. 6, 2012. Author Manuscript, 13 pages.
Soskine et al., Single-Molecule Analyte Recognition with ClyA Nanopores Equipped with Internal Protein Adaptors. J Am Chem Soc. 2015;137:5793-97.
Soskine et al., Tuning the size and properties of ClyA nanopores assisted by directed evolution. J Am Chem Soc. Sep. 11, 2013;135(36):13456-63. doi: 10.1021/ja4053398. Epub Aug. 27, 2013.
Sternberg et al., DNA interrogation by the CRISPR RNA-guided endonuclease Cas9. Nature. Mar. 6, 2014;507(7490):62-7. doi: 10.1038/nature13011. Epub Jan. 29, 2014. Author Manuscript, 16 pages.

Stoddart et al., Multiple base-recognition sites in a biological nanopore: two heads are better than one. Angew Chem Int Ed Engl. 2010;49(3):556-9. doi: 10.1002/anie.200905483.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Sutherland et al., An analysis of mismatched duplex DNA unzipping through a bacterial nanopore. Biochem Cell Biol. Jun. 2004;82(3):407-12.
Taylor et al., Atomic resolution insights into curli fiber biogenesis. Structure. Sep. 7, 2011;19(9):1307-16. doi: 10.1016/j.str.2011.05.015.
Taylor et al., New insight into the molecular control of bacterial functional amyloids. Front Cell Infect Microbiol. Apr. 8, 2015;5:33. doi: 10.3389/fcimb.2015.00033.
Trewick et al., Oxidative Demethylation by *Escherichia coli* AlkB Directly Reverts DNA Base Damage. Nature. Sep. 12, 2002:419:174-78.
Tuteja et al., Helicases as molecular motors: An insight. Physica A. Dec. 1, 2006;372(1):70-83. doi: 10.1016/j.physa.2006.05.014. Epub Jun. 5, 2006.
Van De Goor, Nanopore Detection: Threading DNA Through a Tiny Hole. PharmaGenomics, vol. 4 (3):28-30 (2004).
Van Der Verren et al., A dual-constriction biological nanopore resolves homonucleotide sequences with high fidelity. Nat Biotechnol. Dec. 2020;38(12):1415-1420. doi: 10.1038/s41587-020-0570-8. Epub Jul. 6, 2020. Author Manuscript, 25 pages.
Van Gerven et al., Bacterial amyloid formation: structural insights into curli biogenesis. Trends Microbiol. Nov. 2015; 23(11): 693-706. EPub Oct. 1, 2015. doi: 10.1016/j.tim.2015.07.010. Author Manuscript, 24 pages.
Van Gerven et al., Secretion and functional display of fusion proteins through the curlibiogenesis pathway. Mol Microbiol. Mar. 2014;91(5):1022-35. doi:10.1111/mmi.12515. Epub Feb. 12, 2014.
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f. Author Manuscript, 16 pages.
Van Meervelt et al., Detection of Two Isomeric Binding Configurations in a Protein-Aptamer Complex with a Biological Nanopore. Am Chem Soc. Dec. 10, 2014;8(12):12826-35.
Van Meervelt et al., Real-Time Conformational Changes and Controlled Orientation of Native Proteins Inside a Protein Nanoreactor. J Am Chem Soc. Dec. 27, 2017; 139(51): 18640-18646. EPub Dec. 5, 2017. doi: 10.1021/jacs.7b10106.
Walker et al., Assembly of the oligomeric membrane pore formed by Staphylococcal alpha-hemolysin examined by truncation mutagenesis. J Biol Chem. Oct. 25, 1992;267(30):21782-6.
Walker et al., Key residues for membrane binding, oligomerization, and pore forming activity of staphylococcal alpha-hemolysin identified by cysteine scanning mutagenesis and targeted chemical modification. J Biol Chem. Sep. 29, 1995;270(39):23065-71.
Wallace et al., *E. coli* hemolysin E (HlyE, ClyA, SheA): X-ray crystal structure of the toxin and observation of membrane pores by electron microscopy. Cell. Jan. 21, 2000;100(2):265-76.
Wang et al., Engineering of protein nanopores for sequencing, chemical or protein sensing and disease diagnosis. Curr Opin Biotechnol. Jun. 2018;51:80-89. doi: 10.1016/j.copbio.2017.11.006. Epub Dec. 10, 2017.
Wang et al., Measuring and modeling the kinetics of individual DNA-DNA polymerase complexes on a nanopore. ACS Nano. May 28, 2013;7(5):3876-86. doi: 10.1021/nn401180j. Epub Apr. 16, 2013.
Wang et al., Nanopores with a spark for single-molecule detection. Nat Biotechnol. Jul. 2001;19(7):622-3.
Wang et al., Protein engineering with non-natural amino acids. InTechOpen; Feb. 24, 2012. DOI: 10.5772/28719.
Wanunu et al., DNA translocation governed by interactions with solid-state nanopores. Biophys J. Nov. 15, 2008;95(10):4716-25. doi: 10.1529/biophysj.108.140475. Epub Aug. 15, 2008.

(56) References Cited

OTHER PUBLICATIONS

Wanunu, Nanopores: A journey towards DNA sequencing. Phys Life Rev. Jun. 2012;9(2):125-58. doi:10.1016/j.plrev.2012.05.010. Epub May 18, 2012.

Welford et al., The Selectivity and Inhibition of AlkB. J. Biol. Chem. Mar. 21, 2003;278(12):10157-161.

Wendell et al., Translocation of double-stranded DNA through membrane-adapted phi29 motor protein nanopores. Nat Nanotechnol. 2009;4(11):765-772. doi: 10.1038/nnano.2009.259.

White et al., Single Ion-Channel Recordings Using Glass Nanopore Membranes. J Am Chem Soc. 2007;129:11766-775.

Wiedmann et al., Ligase chain reaction (LCR)—overview and applications. PCR Methods Appl. Feb. 1994;3(4):S51-64. doi: 10.1101/gr.3.4.s51.

Wilkinson et al., Bacterial DNA ligases. Mol Microbiol. Jun. 2001;40(6):1241-8. doi: 10.1046/j.1365-2958.2001.02479.x.

Wolfe et al., Catalyzing the translocation of polypeptides through attractive interactions. J Am Chem Soc. Nov. 14, 2007;129(45):14034-41. Epub Oct. 19, 2007.

Wong et al., Polymer capture by electro-osmotic flow of oppositely charged nanopores. J Chem Phys. Apr. 28, 2007;126(16):164903.

Wu et al., Protein nanopores with covalently attached molecular adapters. J Am Chem Soc. Dec. 26, 2007;129(51):16142-8. Epub Nov. 30, 2007.

Wu et al., Sequence-specific capture of protein-DNA complexes for mass spectrometric protein identification. PLoS One. 2011;6(10):e26217. doi: 10.1371/journal.pone.0026217. Epub Oct. 20, 2011.

Wu et al., Single-molecule detection of nitrogen mustards by covalent reaction within a protein nanopore. J Am Chem Soc. May 28, 2008;130(21):6813-9. doi: 10.1021/ja8004607. Epub Apr. 30, 2008.

Yen et al., SWR-C and INO80 chromatin remodelers recognize nucleosome-free regions near +1 nucleosomes. Cell. Sep. 12, 2013;154(6):1246-56. doi: 10.1016/j.cell.2013.08.043.

Yoo et al., Glucose Biosensors: An Overview of Use in Clinical Practice. Sensors. May 4, 2010;10:4558-4576.

Zernia et al., Current Blockades of Proteins inside Nanopores for Real-Time Metabolome Analysis. ACS Nano. Feb. 25, 2020; 14(2): 2296-2307. EPub Jan. 31, 2020. doi: 10.1021/acsnano.9b09434.

Zernia et al., Current Blockades of Proteins inside Nanopores for Real-Time Metabolome Analysis. ACS Nano. Feb. 25, 2020; 14(Supplemental Information). EPub Jan. 31, 2020. doi: 10.1021/acsnano.9b09434. 19 pages.

Zheng et al., MotionCor2: anisotropic correction of beam-induced motion for improved cryo-electron microscopy. Nat Methods. Apr. 2017;14(4):331-332. doi: 10.1038/nmeth.4193. Epub Feb. 27, 2017.

Zhou et al., Ion Channel Probes for Scanning Ion Conductance Microscopy. Langmuir. Nov. 25, 2014;30:15351-355.

MUTANT LYSENIN PORES

RELATED APPLICATIONS

This application is a continuation of U.S. application Ser. No. 17/108,536, filed Dec. 1, 2020, which is a continuation of U.S. application Ser. No. 15/692,498, filed Aug. 31, 2017, which is a continuation of U.S. application Ser. No. 14/391,660, filed Oct. 9, 2014, which is a national stage filing under 35 U.S.C. § 371 of International Patent Application No. PCT/GB2013/050667, filed Mar. 15, 2013, which claims the benefit under 35 U.S.C. § 119 (e) to U.S. Provisional Application No. 61/622,174, filed Apr. 10, 2012; the entire contents of each of which are incorporated herein by reference in their entireties.

REFERENCE TO AN ELECTRONIC SEQUENCE LISTING

The contents of the electronic sequence listing (0036670026US04-SEQ-MSB.xml; Size: 31,091 bytes; and Date of Creation: Oct. 17, 2023) is herein incorporated by reference in its entirety.

FIELD OF THE INVENTION

The invention relates to mutant forms of lysenin. The invention also relates to analyte characterisation using the mutant forms of lysenin.

BACKGROUND OF THE INVENTION

Nanopore sensing is an approach to sensing that relies on the observation of individual binding or interaction events between analyte molecules and a receptor. Nanopore sensors can be created by placing a single pore of nanometer dimensions in an insulating membrane and measuring voltage-driven ionic transport through the pore in the presence of analyte molecules. The identity of an analyte is revealed through its distinctive current signature, notably the duration and extent of current block and the variance of current levels.

There is currently a need for rapid and cheap nucleic acid (e.g. DNA or RNA) sequencing technologies across a wide range of applications. Existing technologies are slow and expensive mainly because they rely on amplification techniques to produce large volumes of nucleic acid and require a high quantity of specialist fluorescent chemicals for signal detection. Nanopore sensing has the potential to provide rapid and cheap nucleic acid sequencing by reducing the quantity of nucleotide and reagents required.

Two of the essential components of sequencing nucleic acids using nanopore sensing are (1) the control of nucleic acid movement through the pore and (2) the discrimination of nucleotides as the nucleic acid polymer is moved through the pore. In the past, to achieve nucleotide discrimination the nucleic acid has been passed through a mutant of hemolysin. This has provided current signatures that have been shown to be sequence dependent. It has also been shown that a large number of nucleotides contribute to the observed current when a hemolysin pore is used, making a direct relationship between observed current and polynucleotide challenging.

While the current range for nucleotide discrimination has been improved through mutation of the hemolysin pore, a sequencing system would have higher performance if the current differences between nucleotides could be improved further. In addition, it has been observed that when the nucleic acids are moved through a pore, some current states show high variance. It has also been shown that some mutant hemolysin pores exhibit higher variance than others. While the variance of these states may contain sequence specific information, it is desirable to produce pores that have low variance to simplify the system. It is also desirable to reduce the number of nucleotides that contribute to the observed current.

Lysenin (also known as efL1) is a pore-forming toxin purified from the coelomic fluid of the earthworm *Eisenia fetida*. It specifically binds to sphingomyelin, which inhibits lysenin-induced hemolysis (Yamaji et al., J. Biol. Chem. 1998: 273(9): 5300-6). The crystal structure of lysenin is disclosed in De Colbis et al., Structure, 2012; 20: 1498-1507.

SUMMARY OF THE INVENTION

The inventors have surprisingly identified a region within the lysenin monomer which can be modified to alter the interaction between the monomer and a polynucleotide. This region corresponds to from about position 44 to about position 126 of SEQ ID NO: 2. The invention concerns mutant monomers in which one or more modifications have been made to the identified region to improve the ability of the monomer to interact with a polynucleotide. The inventors have also surprisingly demonstrated that pores comprising the novel mutant monomers have an enhanced ability to interact with polynucleotides and therefore display improved properties for estimating the characteristics of, such as the sequence of, polynucleotides. The mutant pores surprisingly display improved nucleotide discrimination. In particular, the mutant pores surprisingly display an increased current range, which makes it easier to discriminate between different nucleotides, and a reduced variance of states, which increases the signal-to-noise ratio. In addition, the number of nucleotides contributing to the current as the polynucleotide moves through the pore is decreased. This makes it easier to identify a direct relationship between the observed current as the polynucleotide moves through the pore and the polynucleotide.

Accordingly, the invention provides a mutant lysenin monomer comprising a variant of the sequence shown in SEQ ID NO: 2, wherein the monomer is capable of forming a pore and wherein the variant comprises one or more modifications within the region of from about position 44 to about position 126 of SEQ ID NO: 2 which alter the ability of the monomer to interact with a polynucleotide.

The invention also provides.

a construct comprising two or more covalently attached monomers derived from lysenin, wherein at least one of the monomers is a mutant lysenin monomer of the invention, a polynucleotide which encodes a mutant lysenin monomer of the invention or a genetically fused construct of the invention;

a homo-oligomeric pore derived from lysenin comprising a sufficient number of mutant lysenin monomers of the invention;

a hetero-oligomeric pore derived from lysenin comprising at least one mutant lysenin monomer of the invention;

a pore comprising at least one construct of the invention;

a method of characterising a target analyte, comprising:
 (a) contacting the target polynucleotide with a pore of the invention such that the target polynucleotide moves through the pore; and (b) taking one or more measurements as the analyte moves with respect to the pore wherein the measurements are indicative of one or more characteristics of the target analyte and thereby characterising the target analyte;

a method of forming a sensor for characterising a target polynucleotide, comprising forming a complex between a pore of the invention and a polynucleotide binding protein and thereby forming a sensor for characterising the target polynucleotide;

a sensor for characterising a target polynucleotide, comprising a complex between a pore of the invention and a polynucleotide binding protein;

use of a pore of the invention to characterise a target analyte;

a kit for characterising a target polynucleotide comprising (a) a pore of the invention and (b) a polynucleotide binding protein;

an apparatus for characterising target polynucleotides in a sample, comprising (a) a plurality of pores of the invention and (b) a plurality of polynucleotide binding proteins;

a method of improving the ability of a lysenin monomer comprising the sequence shown in SEQ ID NO: 2 to characterise a polynucleotide, comprising making one or more modifications within the region of from about position 44 to about position 126 of SEQ ID NO: 2 which alter the ability of the monomer to interact with a polynucleotide and do not affect the ability of the monomer to form a pore;

a method of producing a construct of the invention, comprising covalently attaching at least one mutant lysenin monomer of the invention to one or more monomers derived from lysenin; and a method of forming a pore of the invention, comprising allowing at least one mutant monomer of the invention or at least one construct of the invention to oligomerise with a sufficient number of monomers of the invention, constructs of the invention or monomers derived from lysenin to form a pore.

DESCRIPTION OF THE SEQUENCE LISTING

Figure 1:
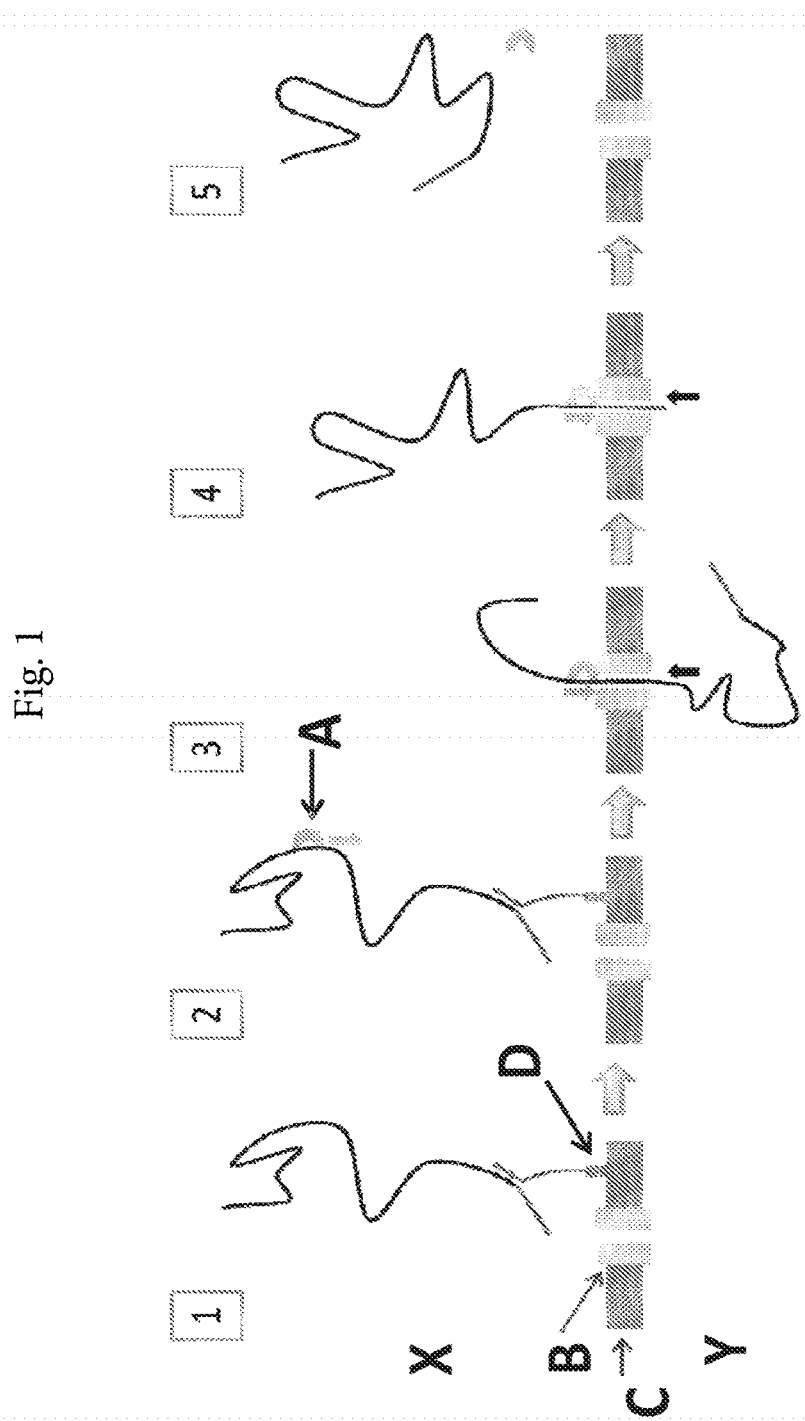
FIG. 1 shows an example schematic of the use of a helicase (labelled A) to control DNA movement through a lysenin nanopore (labelled B). 1) A ssDNA substrate with an annealed primer containing a cholesterol-tag (labelled D) is added to the cis side (labelled X) of the bilayer (labelled C). The cholesterol tag binds to the bilayer, enriching the substrate at the bilayer surface. 2) Helicase added to the cis compartment binds to the DNA. In the presence of divalent metal ions and NTP substrate, the helicase moves along the DNA (grey arrow). 3) Under an applied voltage, the DNA substrate is captured by the nanopore via the leader section on the DNA. The DNA is pulled through the pore under the force of the applied potential until a helicase, bound to the DNA, contacts the top of the pore, preventing further uncontrolled DNA translocation. During this process dsDNA sections (such as the primer) are removed. The helicase movement along the DNA in a 3' to 5' direction pulls the threaded DNA (direction of DNA movement shown with a black arrow) out of the pore against the applied field. 4) The helicase pulls the DNA out of the nanopore, feeding it back to the cis compartment. The last section of DNA to pass through the nanopore is the 5'-leader. 5) When the helicase moves the DNA out of the nanopore it is lost back to the cis compartment. Alternatively, if the DNA is captured by the 3' end, then the DNA will move through the pore from cis to trans (labelled Y) under control of the 3'-5' helicase, finally exiting on the trans side of the bilayer.

SEQ ID NO: 1 shows the polynucleotide sequence encoding the lysenin monomer.
SEQ ID NO: 2 shows the amino acid sequence of the lysenin monomer.
SEQ ID NO: 3 shows the polynucleotide sequence encoding the Phi29 DNA polymerase.
SEQ ID NO: 4 shows the amino acid sequence of the Phi29 DNA polymerase.
SEQ ID NO: 5 shows the codon optimised polynucleotide sequence derived from the sbcB gene from *E. coli*. It encodes the exonuclease I enzyme (EcoExo I) from *E. coli*.
SEQ ID NO: 6 shows the amino acid sequence of exonuclease I enzyme (EcoExo I) from *E. coli*.
SEQ ID NO: 7 shows the codon optimised polynucleotide sequence derived from the xthA gene from *E. coli*. It encodes the exonuclease III enzyme from *E. coli*.
SEQ ID NO: 8 shows the amino acid sequence of the exonuclease III enzyme from *E. coli*. This enzyme performs distributive digestion of 5' monophosphate nucleosides from one strand of double stranded DNA (dsDNA) in a 3'-5' direction. Enzyme initiation on a strand requires a 5' overhang of approximately 4 nucleotides.
SEQ ID NO: 9 shows the codon optimised polynucleotide sequence derived from the recJ gene from *T. thermophilus*. It encodes the RecJ enzyme from *T. thermophilus* (TthRecJ-cd).
SEQ ID NO: 10 shows the amino acid sequence of the RecJ enzyme from *T. thermophilus* (TthRecJ-cd). This enzyme performs processive digestion of 5' monophosphate nucleosides from ssDNA in a 5'-3' direction. Enzyme initiation on a strand requires at least 4 nucleotides.
SEQ ID NO: 11 shows the codon optimised polynucleotide sequence derived from the bacteriophage lambda exo (redX) gene. It encodes the bacteriophage lambda exonuclease.
SEQ ID NO: 12 shows the amino acid sequence of the bacteriophage lambda exonuclease. The sequence is one of three identical subunits that assemble into a trimer. The enzyme performs highly processive digestion of nucleotides from one strand of dsDNA, in a 5'-3' direction (http://www.neb.com/nebecomm/products/productM0262.asp). Enzyme initiation on a strand preferentially requires a 5' overhang of approximately 4 nucleotides with a 5' phosphate.
SEQ ID NO: 13 and 14 show the polynucleotide sequences of ssDNA used in Examples 1, 2, 3, 4, 5 and 6. SEQ ID NO: 14 has a 3'-cholesterol tag.
SEQ ID NO: 15 shows the amino acid sequence of Hel308 Mbu.
SEQ ID NO: 16 shows the amino acid sequence of lysenin related protein (LRP) 1.
SEQ ID NO: 17 shows the amino acid sequence of lysenin related protein (LRP) 1.
SEQ ID NO: 18 shows the amino acid sequence of lysenin related protein (LRP) 1.
SEQ ID NO: 19 shows the amino acid sequence of the activated version of parasporin-2.
The full length protein is cleaved at its amino and carboxy termini to form an activated version that is capable of forming pores.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a mutant monomer" includes "mutant monomers", reference to "a substitution" includes two or more such substitutions, reference to "a pore" includes two or more such pores, reference to "a polynucleotide" includes two or more such polynucleotides, and the like.

All publications, patents and patent applications cited herein, whether supra or infra, are hereby incorporated by reference in their entirety.

Mutant Lysenin Monomers

The present invention provides mutant lysenin monomers. The mutant lysenin monomers may be used to form the pores of the invention. A mutant lysenin monomer is a monomer whose sequence varies from that of a wild-type lysenin monomer (i.e. SEQ ID NO: 2) and which retains the ability to form a pore in the presence of other monomers of the invention or other monomers from lysenin or derived from lysenin. Methods for confirming the ability of mutant monomers to form pores are well-known in the art and are discussed in more detail below. For instance, the ability of a mutant monomer to form a pore can be determined as described in Example 1.

The mutant monomers have an altered ability to interact with a polynucleotide. Pores comprising one or more of the mutant monomers therefore have improved nucleotide reading properties e.g. display (1) improved polynucleotide capture and (2) improved polynucleotide recognition or discrimination. In particular, pores constructed from the mutant monomers capture nucleotides and polynucleotides more easily than the wild type. In addition, pores constructed from the mutant monomers display an increased current range, which makes it easier to discriminate between different nucleotides, and a reduced variance of states, which increases the signal-to-noise ratio. In addition, the number of nucleotides contributing to the current as the polynucleotide moves through pores constructed from the mutants is decreased. This makes it easier to identify a direct relationship between the observed current as the polynucleotide moves through the pore and the polynucleotide. The improved nucleotide reading properties of the mutants are achieved via five main mechanisms, namely by changes in the:
    sterics (increasing or decreasing the size of amino acid residues);
    charge (e.g. introducing or removing −ve charge and/or introducing or removing +ve charge);
    hydrogen bonding (e.g. introducing amino acids that can hydrogen bond to the base pairs);

pi stacking (e.g. introducing amino acids that interact through delocalised electron pi systems); and/or alteration of the structure of the pore (e.g. introducing amino acids that increase the size of the barrel or channel).

Any one or more of these five mechanisms may be responsible for the improved properties of the pores formed from the mutant monomers of the invention. For instance, a pore comprising a mutant monomer of the invention may display improved nucleotide reading properties as a result of altered sterics, altered hydrogen bonding and an altered structure.

A mutant monomer of the invention comprises a variant of the sequence shown in SEQ ID NO: 2. SEQ ID NO: 2 is the wild-type sequence of the lysenin monomer. A variant of SEQ ID NO: 2 is a polypeptide that has an amino acid sequence which varies from that of SEQ ID NO: 2 and which retains its ability to form a pore.

The inventors have surprisingly identified a region within the lysenin monomer which can be modified to alter the interaction between the monomer and a polynucleotide, such as when the polynucleotide is characterised using nanopore sensing with a pore comprising the monomer. The region is from about position 44 to about position 126 of SEQ ID NO: 2. At least a part of this region typically contributes to the membrane spanning region of lysenin. At least a part of this region typically contributes to the barrel or channel of lysenin. At least a part of this region typically contributes to the internal wall or lining of lysenin.

The transmembrane region of lysenin has been identified as positions 44 to 67 of SEQ ID NO: 2 (De Colbis et al., Structure, 2012; 20: 1498-1507).

In accordance with the invention, the variant comprises one or more modifications within the region of from about position 44 to about position 126 of SEQ ID NO: 2 which alter the ability of the monomer, or preferably the region, to interact with a polynucleotide. The interaction between the monomer and a polynucleotide may be increased or decreased An increased interaction between the monomer and a polynucleotide will, for example, facilitate capture of the polynucleotide by pores comprising the mutant monomer. A decreased interaction between the region and a polynucleotide will, for example, improve recognition or discrimination of the polynucleotide. Recognition or discrimination of the polynucleotide may be improved by decreasing the variance of states of pores comprising the mutant monomer (which increases the signal-to-noise ratio) and/or decreasing the number of nucleotides in the polynucleotide contributing to the current as the polynucleotide moves through pores comprising the mutant monomer.

The invention therefore provides a mutant lysenin monomer comprising a variant of the sequence shown in SEQ ID NO: 2, wherein the monomer is capable of forming a pore and wherein the variant comprises one or more modifications from about position 44 to about position 126 of SEQ ID NO: 2 which alter the ability of the monomer to interact with a polynucleotide.

The ability of the monomer to interact with a polynucleotide can be determined using methods that are well-known in the art. The monomer may interact with a polynucleotide in any way, e.g. by non-covalent interactions, such as hydrophobic interactions, hydrogen bonding, Van der Waal's forces, pi ($\pi$)-cation interactions or electrostatic forces. For instance, the ability of the region to bind to a polynucleotide can be measured using a conventional binding assay. Suitable assays include, but are not limited to, fluorescence-based binding assays, nuclear magnetic resonance (NMR), Isothermal Titration calorimetry (ITC) or Electron spin resonance (ESR) spectroscopy. Alternatively, the ability of a pore comprising one or more of the mutant monomers to interact with a polynucleotide can be determined using any of the methods discussed above or below. Preferred assays are described in the Examples.

The one or more modifications are within the region from about position 44 to about position 126 of SEQ ID NO: 2. The one or more modifications are preferably within any one of the following regions: from about position 40 to about position 125, from about position 50 to about position 120, from about position 60 to about position 110 and from about position 70 to about position 100. If the one or more modifications are being made to improve polynucleotide capture, they are more preferably made within any one of the following regions: from about position 44 to about position 103, from about position 68 to about position 103, from about position 84 to about position 103, from about position 44 to about position 97, from about position 68 to about position 97 or from about position 84 to about position 97. If the one or more modifications are being made to improve polynucleotide recognition or discrimination, they are more preferably made within any one of the following regions: from about position 44 to about position 109, from about position 44 to about position 97 or from about position 48 to about position 88. The region is preferably from about position 44 to about position 67 of SEQ ID NO: 2.

If the one or more modifications are intended improve polynucleotide recognition or discrimination, they are preferably made in addition to one or more modifications to improve polynucleotide capture. This allows pores formed from the mutant monomer to effectively capture a polynucleotide and then characterise the polynucleotide, such as estimate its sequence, as discussed below.

Modifications of protein nanopores that alter their ability to interact with a polynucleotide, in particular improve their ability to capture and/or recognise or discriminate polynucleotides, are well documented in the art. For instance, such modifications are disclosed in WO 2010/034018 and WO 2010/055307. Similar modifications can be made to the lysenin monomer in accordance with this invention.

Any number of modifications may be made, such as 1, 2, 5, 10, 15, 20, 30 or more modifications. Any modification(s) can be made as long as the ability of the monomer to interact with a polynucleotide is altered. Suitable modifications include, but are not limited to, amino acid substitutions, amino acid additions and amino acid deletions. The one or more modifications are preferably one or more substitutions. This is discussed in more detail below.

The one or more modifications preferably (a) alter the steric effect of the monomer, or preferably alter the steric effect of the region, (b) alter the net charge of the monomer, or preferably alter the net charge of the region, (c) alter the ability of the monomer, or preferably of the region, to hydrogen bond with the polynucleotide, (d) introduce or remove chemical groups that interact through delocalized electron pi systems and/or (e) alter the structure of the monomer, or preferably alter the structure of the region. The one or more modifications more preferably result in any combination of (a) to (e), such as (a) and (b); (a) and (c); (a) and (d); (a) and (c); (b) and (c); (b) and (d); (b) and (c); (c) and (d); (c) and (e); (d) and (e), (a), (b) and (c); (a), (b) and (d): (a). (b) and (e): (a), (c) and (d); (a), (c) and (e): (a), (d) and (e); (b), (c) and (d); (b), (c) and (e); (b), (d) and (e); (c), (d) and (e); (a), (b), (c) and d), (a), (b), (c) and (e); (a), (b), (d) and (e); (a), (c), (d) and (e); (b), (c), (d) and (e); and (a), (b), (c) and (d).

For (a), the steric effect of the monomer can be increased or decreased. Any method of altering the steric effects may be used in accordance with the invention. The introduction of bulky residues, such as phenylalanine (F), tryptophan (W), tyrosine (Y) or histidine (H), increases the sterics of the monomer. The one or more modifications are preferably the introduction of one or more of F, W, Y and H. Any combination of F, W, Y and H may be introduced. The one or more of F, W, Y and H may be introduced by addition. The one or more of F, W, Y and H are preferably introduced by substitution. Suitable positions for the introduction of such residues are discussed in more detail below.

The removal of bulky residues, such as phenylalanine (F), tryptophan (W), tyrosine (Y) or histidine (H), conversely decreases the sterics of the monomer. The one or more modifications are preferably the removal of one or more of F, W, Y and H. Any combination of F, W, Y and H may be removed. The one or more of F, W, Y and H may be removed by deletion. The one or more of F, W, Y and H are preferably removed by substitution with residues having smaller side groups, such as serine (S), threonine (T), alanine (A) and valine (V).

For (b), the net charge can be altered in any way. The net positive charge is preferably increased or decreased. The net positive charge can be increased in any manner. The net positive charge is preferably increased by introducing, preferably by substitution, one or more positively charged amino acids and/or neutralising, preferably by substitution, one or more negative charges.

The net positive charge is preferably increased by introducing one or more positively charged amino acids. The one or more positively charged amino acids may be introduced by addition. The one or more positively charged amino acids are preferably introduced by substitution. A positively charged amino acid is an amino acid with a net positive charge. The positively charged amino acid(s) can be naturally-occurring or non-naturally-occurring. The positively charged amino acids may be synthetic or modified. For instance, modified amino acids with a net positive charge may be specifically designed for use in the invention. A number of different types of modification to amino acids are well known in the art.

Preferred naturally-occurring positively charged amino acids include, but are not limited to, histidine (H), lysine (K) and arginine (R). The one or more modifications are preferably the introduction of one or more of H, K and R. Any number and combination of H, K and R may be introduced. The one or more of H, K and R may be introduced by addition. The one or more of H, K and R are preferably introduced by substitution. Suitable positions for the introduction of such residues are discussed in more detail below.

Methods for adding or substituting naturally-occurring amino acids are well known in the art. For instance, methionine (M) may be substituted with arginine (R) by replacing the codon for methionine (ATG) with a codon for arginine (AGA) at the relevant position in a polynucleotide encoding the monomer. The polynucleotide can then be expressed as discussed below.

Methods for adding or substituting non-naturally-occurring amino acids are also well known in the art. For instance, non-naturally-occurring amino acids may be introduced by including synthetic aminoacyl-tRNAs in the IVTT system used to express the pore. Alternatively, they may be introduced by expressing the monomer in $E.\ coli$ that are auxotrophic for specific amino acids in the presence of synthetic (i.e. non-naturally-occurring) analogues of those specific amino acids. They may also be produced by naked ligation if the pore is produced using partial peptide synthesis.

Any amino acid may be substituted with a positively charged amino acid. One or more uncharged amino acids, non-polar amino acids and/or aromatic amino acids may be substituted with one or more positively charged amino acids Uncharged amino acids have no net charge. Suitable uncharged amino acids include, but are not limited to, cysteine (C), serine (S), threonine (T), methionine (M), asparagine (N) and glutamine (Q). Non-polar amino acids have non-polar side chains. Suitable non-polar amino acids include, but are not limited to, glycine (G), alanine (A), proline (P), isoleucine (I), leucine (L) and valine (V). Aromatic amino acids have an aromatic side chain. Suitable aromatic amino acids include, but are not limited to, histidine (H), phenylalanine (F), tryptophan (W) and tyrosine (Y). Preferably, one or more negatively charged amino acids are substituted with one or more positively charged amino acids. Suitable negatively charged amino acids include, but are not limited to, aspartic acid (D) and glutamic acid (E).

Preferred introductions include, but are not limited to, substitution of substitution E with K, M with R, substitution of M with H, substitution of M with K, substitution of D with R, substitution of D with H, substitution of D with K, substitution of E with R, substitution of E with H, substitution of N with R, substitution of T with R and substitution of G with R. Most preferably E is substituted with K.

Any number of positively charged amino acids may be introduced or substituted. For instance, 1, 2, 5, 10, 15, 20, 25, 30 or more positively charged amino acids may be introduced or substituted.

The net positive charge is more preferably increased by neutralising one or more negative charges. The one or more negative charges may be neutralised by replacing by substitution one or more negatively charged amino acids with one or more uncharged amino acids, non-polar amino acids and/or aromatic amino acids. The removal of negative charge increases the net positive charge. The uncharged amino acids, non-polar amino acids and/or aromatic amino acids can be naturally-occurring or non-naturally-occurring. They may be synthetic or modified. Suitable uncharged amino acids, non-polar amino acids and aromatic amino acids are discussed above. Preferred substitutions include, but are not limited to, substitution of E with Q, substitution of E with S, substitution of E with A, substitution of D with Q, substitution of E with N, substitution of D with N, substitution of D with G and substitution of D with S.

Any number and combination of uncharged amino acids, non-polar amino acids and/or aromatic amino acids may be substituted. For instance, 1, 2, 5, 10, 15, 20, 25, or 30 or more uncharged amino acids, non-polar amino acids and/or aromatic amino acids may be substituted. Negatively charged amino acids may be substituted with (1) uncharged amino acids; (2) non-polar amino acids; (3) aromatic amino acids; (4) uncharged amino acids and non-polar amino acids; (5) uncharged amino acids and aromatic amino acids; and (5) non-polar amino acids and aromatic amino acids, or (6) uncharged amino acids, non-polar amino acids and aromatic amino acids.

The one or more negative charges may be neutralised by introducing one or more positively charged amino acids near to, such as within 1, 2, 3 or 4 amino acids, or adjacent to one or more negatively charged amino acids. Examples of positively and negatively charged amino acids are discussed above. The positively charged amino acids may be introduced in any manner discussed above, for instance by substitution.

The net positive charge is preferably decreased by introducing one or more negatively charged amino acids and/or neutralising one or more positive charges. Ways in which this might be done will be clear from the discussion above with reference to increasing the net positive charge. All of the embodiments discussed above with reference to increasing the net positive charge equally apply to decreasing the net positive charge except the charge is altered in the opposite way. In particular, the one or more positive charges are preferably neutralised by substituting one or more positively charged amino acids with one or more uncharged amino acids, non-polar amino acids and/or aromatic amino acids or by introducing one or more negatively charged amino acids near to, such as within 1, 2, 3 or 4 amino acids of, or adjacent to one or more negatively charged amino acids.

The net negative charge is preferably increased or decreased. All of the above embodiments discussed above with reference to increasing or decreasing the net positive charge equally apply to decreasing or increasing the net negative charge respectively.

For (c), the ability of the monomer to hydrogen bond may be altered in any manner. The introduction of serine (S), threonine (T), asparagine (N), glutamine (Q), tyrosine (Y) or histidine (H) increases the hydrogen bonding ability of the monomer. The one or more modifications are preferably the introduction of one or more of S, T, N, Q, Y and H. Any combination of S, T, N, Q, Y and H may be introduced. The one or more of S, T, N, Q, Y and H may be introduced by addition. The one or more of S, T, N, Q, Y and H are preferably introduced by substitution. Suitable positions for the introduction of such residues are discussed in more detail below.

The removal of serine (S), threonine (T), asparagine (N), glutamine (Q), tyrosine (Y) or histidine (H) decreases the hydrogen bonding ability of the monomer. The one or more modifications are preferably the removal of one or more of S, T, N, Q, Y and H. Any combination of S, T, N, Q, Y and H may be removed. The one or more of S, T, N, Q, Y and H may be removed by deletion. The one or more of S, T, N, Q, Y and H are preferably removed by substitution with other amino acids which hydrogen bond less well, such as alanine (A), valine (V), isoleucine (I) and leucine (L).

For (d), the introduction of aromatic residues, such as phenylalanine (F), tryptophan (W), tyrosine (Y) or histidine (H), also increases the pi stacking in the monomer. The removal of aromatic residues, such as phenylalanine (F), tryptophan (W), tyrosine (Y) or histidine (H), also increases the pi stacking in the monomer. Such amino acids can be introduced or removed as discussed above with reference to (a).

For (e), one or more modifications made in accordance with the invention which alter the structure of the monomer. For example, one or more loop regions can be removed, shortened or extended. This typically facilitates the entry or exit of a polynucleotide into or out of the pore. The one or more loop regions may be the cis side of the pore, the trans side of the pore or on both sides of the pore. Alternatively, one or more regions of the amino terminus and/or the carboxy terminus of the pore can be extended or deleted. This typically alters the size and/or charge of the pore.

It will be clear from the discussion above that the introduction of certain amino acids will enhance the ability of the monomer to interact with a polynucleotide via more than one mechanism. For instance, the substitution of E with H will not only increase the net positive charge (by neutralising negative charge) in accordance with (b), but will also increase the ability of the monomer to hydrogen bond in accordance with (c).

The variant preferably comprises a substitution at one or more of the following positions of SEQ ID NO. 2: M44, N46, N48, E50, R52, H58, D68, F70, E71, S74, E76, S78, Y79, S80, H81, S82, E84, E85, S86, Q87, S89, M90, E92, E94, E97, E102, H103, T104, T106, R115, Q117, N119, D121 and D126. The variant preferably comprises a substitution at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33 or 34 of those positions. The variant preferably comprises a substitution at one or more of the following positions of SEQ ID NO: 2: D68, E71, S74, E76, S78, S80, S82, E84, E85, S86, Q87, S89, E92, E102, T104, T106, R115, Q117, N119 and D121. The variant preferably comprises a substitution at 1, 2, 3, 4, 5, 6, 7, 8, 9, 10, 11, 12, 13, 14, 15, 16, 17, 18, 19 or 20 of those positions. The amino acids substituted into the variant may be naturally-occurring or non-naturally occurring derivatives thereof. The amino acids substituted into the variant may be D-amino acids. Each position listed above may be substituted with asparagine (N), serine (S), glutamine (Q), arginine (R), glycine (G), tyrosine (Y), aspartic acid (D), leucine (L), lysine (K) or alanine (A).

The variant preferably comprises at least one of the following mutations of SEQ ID NO: 2:
(a) serine (S) at position 44;
(b) serine (S) at position 46;
(c) serine (S) at position 48:
(d) serine (S) at position 52;
(e) serine (S) at position 58;
(f) serine (S) at position 68;
(g) serine (S) at position 70;
(h) serine (S) at position 71;
(i) serine (S) at position 76;
(j) serine (S) at position 79;
(k) serine (S) at position 81;
(l) serine (S), aspartic acid (D) or glutamine (Q) at position 84:
(m) serine (S) or lysine (K) at position 85;
(n) serine (S) at position 87;
(o) serine (S) at position 90;
(p) asparagine (N) or glutamine (Q) at position 92;
(q) serine (S) or asparagine (N) at position 94;
(r) serine (S) or asparagine (N) at position 97;
(s) serine (S) at position 102;
(t) serine (S) at position 103;
(u) asparagine (N) or serine (S) at position 121;
(v) serine (S) at position 50;
(w) asparagine (N) or serine (S) at position 94;
(x) asparagine (N) or serine (S) at position 97;
(y) serine (S) or asparagine (N) at position 121;
(z) asparagine (N) or glutamine (Q) or glycine (G) at position 126; and
(aa) serine (S) or asparagine (N) at position 128.

The variant may include any number of mutations (a) to (aa), such as 1, 2, 3, 4, 5, 6, 7, 8, 9, 10, 11, 12, 13, 14, 15, 16, 17, 18, 19, 20, 21, 22, 23, 24, 25, 26 or 27 of the mutations. Preferred combinations of mutations are discussed below. The amino acids introduced into the variant may be naturally-occurring or non-naturally occurring derivatives thereof. The amino acids introduced into the variant may be D-amino acids.

The variant preferably comprises at least one of the following mutations of SEQ ID NO: 2:
(a) serine (S) at position 68;
(b) serine (S) at position 71;
(c) serine (S) at position 76;
(d) aspartic acid (D) or glutamine (Q) at position 84;
(e) lysine (K) at position 85;
(f) asparagine (N) or glutamine (Q) at position 92:
(g) serine (S) at position 102;
(h) asparagine (N) or serine (S) at position 121;
(i) serine (S) at position 50;
(j) asparagine (N) or serine (S) at position 94,
(k) asparagine (N) or serine (S) at position 97, and
(l) asparagine (N) or glutamine (Q) or glycine (G) at position 126.

The variant may include any number of mutations (a) to (1), such as 1, 2, 3, 4, 5, 6, 7, 8, 9, 10, 11 or 12 of the mutations. Preferred combinations of mutations are discussed below. The amino acids introduced into the variant may be naturally-occurring or non-naturally occurring derivatives thereof. The amino acids introduced into the variant may be D-amino acids.

The variant may include one or more additional modifications outside of the region of from about position 44 to about position 126 of SEQ ID NO: 2 which in combination with the modifications in the region discussed above improve polynucleotide capture and/or improve polynucleotide recognition or discrimination. Suitable modifications include, but are not limited to, substitution at one or more of D35, E128, E135, E134 and E167. In particular, removal of the negative charge by substituting E at one or more of positions 128, 135, 134 and 167 improves polynucleotide capture. E at one or more of these positions may be substituted in any of the ways discussed above. Preferably all of E128, E135, E134 and E167 are substituted as discussed above. E is preferably substituted with A. In other words, the variant preferably comprises one or more of, or all of, E128A, E135A, E134A and E167A. Another preferred substitution is D35Q.

In a preferred embodiment, the variant comprises the following substitutions in SEQ ID NO: 2:
i. one or more of, such as both of, E84D and E85K;
ii. one or more of, such as 2, 3, 4, 5 or 6 of, E84Q, E85K, E92Q, E97S, D126G and E167A;
iii. one or more of, such as 2, 3, 4 or 5 of, E92N, E94N, E97N, D121N and D126N;
iv. one or more of, such as 2, 3, 4, 5 or 6 of, E92N, E94N, E97N, D121N, D126N and E128N;
v. one or more of, such as 2, 3, 4, 5, 6 or 7 of, E76S, E84Q, E85K, E92Q, E97S, D126G and E167A;
vi. one or more of, such as 2, 3, 4, 5, 6 or 7 of, E84Q, E85K, E92Q, E97S, D126G, E167A and E50S;
vii. one or more of, such as 2, 3, 4, 5, 6 or 7 of, E84Q, E85K, E92Q, E97S, D126G, E167A and E71S;
viii. one or more of, such as 2, 3, 4, 5, 6 or 7 of, E84Q, E85K, E92Q, E97S, D126G, E167A and E94S;
ix. one or more of, such as 2, 3, 4, 5, 6 or 7 of, E84Q, E85K, E92Q, E97S, D126G, E167A and E102S,
x. one or more of, such as 2, 3, 4, 5, 6 or 7 of, E84Q, E85K, E92Q, E97S, D126G, E167A and E128S;
xi. one or more of, such as 2, 3, 4, 5, 6 or 7 of, E84Q, E85K, E92Q, E97S, D126G, E167A and E135S;
xii. one or more of, such as 2, 3, 4, 5, 6 or 7 of, E84Q, E85K, E92Q, E97S, D126G, E167A and D68S;
xiii. one or more of, such as 2, 3, 4, 5, 6 or 7 of, E84Q, E85K, E92Q, E97S, D126G, E167A and D121S;
xiv. one or more of, such as 2, 3, 4, 5, 6 or 7 of, E84Q, E85K, E92Q, E97S, D126G, E167A and D134S;
xv. one or more of, such as 2 or 3 of, E84D, E85K and E92Q;
xvi. one or more of, such as 1, 2, 3, 4, 5 or 6 of, E84Q, E85K, E92Q, E97S, D126G and E135S;
xvii. one or more of, such as 1, 2, 3, 4 or 5 of, E85K, E92Q, E94S, E97S and D126G;
xviii. one or more of, such as 1, 2, 3, 4 or 5 of, E76S, E85K, E92Q, E97S and D126G;
xix. one or more of, such as 1, 2, 3, 4 or 5 of, E71S, E85K, E92Q, E97S and D126G;
xx. one or more of, such as 1, 2, 3, 4 or 5 of, D68S, E85K, E92Q, E97S and D126G;
xxi. one or more of, such as 1, 2, 3 or 4 of, E85K, E92Q, E97S and D126G;
xxii. one or more of, such as 1, 2, 3, 4, 5 or 6 of, E84Q, E85K, E92Q, E97S, H103S and D126G;
xxiii. one or more of, such as 1, 2, 3, 4, 5 or 6 of, E84Q, E85K, M90S, E92Q, E97S and D126G;
xxiv. one or more of, such as 1, 2, 3, 4, 5 or 6 of, E84Q, Q87S, E85K, E92Q, E97S and D126G;
xxv. one or more of, such as 1, 2, 3, 4 or 5 of, E84Q, E85S, E92Q, E97S and D126G;
xxvi. one or more of, such as 1, 2, 3, 4 or 5 of, E84S, E85K, E92Q, E97S and D126G;
xxvii. one or more of, such as 1, 2, 3, 4, 5 or 6 of, H81S, E84Q, E85K, E92Q, E97S and D126G;
xxviii. one or more of, such as 1, 2, 3, 4, 5 or 6 of, Y79S, E84Q, E85K, E92Q, E97S and D126G;
xxix. one or more of, such as 1, 2, 3, 4, 5 or 6 of, F70S, E84Q, E85K, E92Q, E97S and D126G;
xxx. one or more of, such as 1, 2, 3, 4, 5 or 6 of, H58S, E84Q, E85K, E92Q, E97S and D126G,
xxxi. one or more of, such as 1, 2, 3, 4, 5 or 6 of, R52S, E84Q, E85K, E92Q, E97S and D126G;
xxxii. one or more of, such as 1, 2, 3, 4, 5 or 6 of, N48S, E84Q, E85K, E92Q, E97S and D126G;
xxxiii. one or more of, such as 1, 2, 3, 4, 5 or 6 of, N46S, E84Q, E85K, E92Q, E97S and D126G;
xxxiv. one or more of, such as 1, 2, 3, 4, 5 or 6 of, M44S, E84Q, E85K, E92Q, E97S and D126G;
xxxv. one or more of, such as both of, E92Q and E97S,
xxxvi. one or more of, such as 1, 2, 3 or 4 of, E84Q, E85K, E92Q and E97S;
xxxvii. one or more of, such as both of, E84Q and E85K;
xxxviii. one or more of, such as 1, 2 or 3 of, E84Q, E85K and D126G;
xxxix. one or more of, such as 1, 2, 3 or 4 of, E84Q, E85K, D126G and E167A;
xl. one or more of, such as 1, 2 or 3 of, E92Q, E97S and D126G;
xli. one or more of, such as 1, 2, 3, 4 or 5 of, E84Q, E85K, E92Q, E97S and D126G;
xlii. one or more of, such as 1, 2, 3, 4 or 5 of, E84Q, E85K, E92Q, E97S and E167A;
xliii. one or more of, such as 1, 2, 3, 4 or 5 of, E84Q, E85K, E92Q, D126G and E167A;
xliv. one or more of, such as 1, 2, 3, 4 or 5 of, E84Q, E85K, E97S, D126G and E167A;
xlv. one or more of, such as 1, 2, 3, 4 or 5 of, E84Q, E92Q, E97S, D126G and E167A;
xlvi. one or more of, such as 1, 2, 3, 4 or 5 of, E85K, E92Q, E97S, D126G and E167A;
xlvii. one or more of, such as 1, 2 or 3 of, E84D, E85K and E92Q;

xlviii. one or more of, such as 1, 2, 3, 4, 5, 6 or 7 of, E84Q, E85K, E92Q, E97S, D126G, E167A and D121S;

xlix. one or more of, such as 1, 2, 3, 4, 5, 6 or 7 of, E84Q, E85K, E92Q, E97S, D126G, E167A and D68S;

l. one or more of, such as 1, 2, 3, 4, 5, 6 or 7 of, E84Q, E85K, E92Q, E97S, D126G, E167A and E135S;

li. one or more of, such as 1, 2, 3, 4, 5, 6 or 7 of, E84Q, E85K, E92Q, E97S, D126G, E167A and E128S;

lii. one or more of, such as 1, 2, 3, 4, 5, 6 or 7 of, E84Q, E85K, E92Q, E97S, D126G, E167A and E102S;

liii. one or more of, such as 1, 2, 3, 4, 5, 6 or 7 of, E84Q, E85K, E92Q, E97S, D126G, E167A and E94S;

liv. one or more of, such as 1, 2, 3, 4, 5, 6 or 7 of, E84Q, E85K, E92Q, E97S, D126G, E167A and E71S;

lv. one or more of, such as 1, 2, 3, 4, 5, 6 or 7 of, E84Q, E85K, E92Q, E97S, D126G, E167A and E50S;

lvi. one or more of, such as 1, 2, 3, 4, 5, 6 or 7 of, E76S, E84Q, E85K, E92Q, E97S, D126G and E167A;

lvii. one or more of, such as 1, 2, 3, 4, 5 or 6 of, E92N, E94N, E97N, D121N, D126N and E128N;

lviii. one or more of, such as 1, 2, 3, 4 or 5 of, E92N, E94N, E97N, D121N and D126N; or lix. one or more of, such as 1, 2, 3, 4, 5 or 6 of, E84Q, E85K, E92Q, E97S, D126G and E167A In the above, the first letter refers to the amino acid in SEQ ID NO: 2 being replaced, the number is the position in SEQ ID NO: 2 and the second letter refers to the amino acid with which the first is be substituted. Hence, E84D refers to substitution of glutamic acid (E) at position 84 with aspartic acid (D).

The variant may include any number of the substitutions in any one of i to lix, such as 1, 2, 3, 4, 5, 6 or 7. The variant preferably includes all of the substitutions shown in any one of i to lix above.

In a preferred embodiment, the variant comprises the substitutions in any one of i to xv above. The variant may include any number of the substitutions in any one of i to xv, such as 1, 2, 3, 4, 5, 6 or 7. The variant preferably includes all of the substitutions shown in any one of i to xv above.

If the one or more modifications are intended to improve the ability of the monomer to recognise or discriminate a polynucleotide, they are preferably made in addition to the modifications discussed above that improve polynucleotide capture, such as E84Q, E85K, E92Q, E97S, D126G and E167A.

The one or more modifications made to the identified region may concern the substitution of one or more amino acids in the region with amino acids present at the corresponding position(s) in homologues or paralogues of lysenin. Four examples of homologues of lysenin are shown in SEQ ID NOs: 16 to 19. The advantage of such substitutions is that they are likely to result in mutant monomers that form pores since the homologue monomers also form pores.

In addition to the specific mutations discussed above, the variant may include other mutations. These mutations do not necessarily enhance the ability of the monomer to interact with a polynucleotide. The mutations may facilitate, for example, expression and/or purification. Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO. 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence T is referred to as the neighbourhood word score threshold (Altschul et al, supra). These initial neighbourhood word hits act as seeds for initiating searches to find HSP's containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 1 below. Where amino acids have similar polarity, this can also be determined by reference to the hydropathy scale for amino acid side chains in Table 2.

TABLE 1

Chemical properties of amino acids

| | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

TABLE 2

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

The variant may comprise one or more substitutions outside of the region specified above in which amino acids are replaced with those at the corresponding position(s) in homologues and paralogues of lysenin. Four examples of homologues of lysenin are shown in SEQ ID NOs: 16 to 19.

One or more amino acid residues of the amino acid sequence of SEQ ID NO: 2 may additionally be deleted from the variants described above. Up to 1, 2, 3, 4, 5, 10, 20 or 30 residues may be deleted, or more.

Variants may include fragments of SEQ ID NO: 2. Such fragments retain pore forming activity. This may be assayed as described above. Fragments may be at least 50, 100, 150, 200 or 250 amino acids in length. Such fragments may be used to produce the pores of the invention. Since the region of from about position 44 to about position 126 of SEQ ID NO: 2 can be modified by one or more deletions in accordance with the invention, a fragment does not have to contain the entire region. Hence, fragments shorter than the length of the unmodified region are envisaged by the invention. A fragment preferably comprises the pore forming domain of SEQ ID NO: 2. A fragment more preferably comprises the region from about position 44 to about position 126 of SEQ ID NO: 2 which is modified in accordance with the invention.

One or more amino acids may be alternatively or additionally added to the variants described above. An extension may be provided at the amino terminal or carboxy terminal of the amino acid sequence of the variant of SEQ ID NO: 2, including a fragment thereof. The extension may be quite short, for example from 1 to 10 amino acids in length.

Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the region of SEQ ID NO: 2 that is responsible for pore formation, namely from about position 44 to about position 126 and this region is modified in accordance with the invention as discussed above. It may contain a fragment of this region as discussed above. In addition to the modifications of the invention, a variant of SEQ ID NO: 2 may include one or more additional modifications, such as substitutions, additions or deletions. These modifications are preferably located in the stretches in the variant that correspond to from about position 1 to about position 43 and from about position 127 to about position 297 of SEQ ID NO: 2 (i.e. outside of the region modified in accordance with the invention).

The mutant monomers may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore This has been demonstrated as a method for separating hemolysin hetero-oligomers (Chem Biol. 1997 July; 4(7):497-505).

The mutant monomer may be labelled with a revealing label. The revealing label may be any suitable label which allows the pore to be detected. Suitable labels include, but are not limited to, fluorescent molecules, radioisotopes, e.g. $^{125}I$, $^{55}S$, enzymes, antibodies, antigens, polynucleotides, polyethylene glycols (PEGs), peptides and ligands such as biotin.

The mutant monomer may also be produced using D-amino acids. For instance, the mutant monomer may comprise a mixture of L-amino acids and D-amino acids. This is conventional in the art for producing such proteins or peptides.

The mutant monomer contains one or more specific modifications to facilitate interaction with a polynucleotide. The mutant monomer may also contain other non-specific modifications as long as they do not interfere with pore formation. A number of non-specific side chain modifications are known in the art and may be made to the side chains of the mutant monomer. Such modifications include, for example, reductive alkylation of amino acids by reaction with an aldehyde followed by reduction with NaBH$_4$, amidination with methylacetimidate or acylation with acetic anhydride.

The mutant monomer can be produced using standard methods known in the art. The monomer may be made synthetically or by recombinant means. For example, the monomer may be synthesized by in vitro translation and transcription (IVTT). Suitable methods for producing pore monomers are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed below.

Polynucleotide sequences encoding a mutant monomer may be derived and replicated using standard methods in the art. Such sequences are discussed in more detail below. Polynucleotide sequences encoding a mutant monomer may be expressed in a bacterial host cell using standard techniques in the art. The mutant monomer may be produced in a cell by in situ expression of the polypeptide from a recombinant expression vector. The expression vector optionally carries an inducible promoter to control the expression of the polypeptide.

A mutant monomer may be produced in large scale following purification by any protein liquid chromatography system from pore producing organisms or after recombinant expression as described below. Typical protein liquid chromatography systems include FPLC, AKTA systems, the Bio-Cad system, the Bio-Rad BioLogic system and the Gilson HPLC system. The mutant monomer may then be inserted into a naturally occurring or artificial membrane for use in accordance with the invention. Methods for inserting pore into membranes are discussed below.

In some embodiments, the mutant monomer is chemically modified. The mutant monomer can be chemically modified in any way and at any site. The mutant monomer is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. Suitable non-natural amino acids include, but are not limited to, 4-azido-L-phenylalanine (Faz) and any one of the amino acids numbered 1-71 in FIG. 1 of Liu C. C. and Schultz P. G., Annu. Rev. Biochem., 2010, 79, 413-444. The mutant monomer may be chemically modified by the attachment of any molecule. For instance, the mutant monomer may be chemically modified by attachment of a polyethylene glycol (PEG), a nucleic acid, such as DNA, a dye, a fluorophore or a chromophore.

In some embodiments, the mutant monomer is chemically modified with a molecular adaptor that facilitates the interaction between a pore comprising the monomer and a target analyte, a target nucleotide or target polynucleotide. The presence of the adaptor improves the host-guest chemistry of the pore and the nucleotide or polynucleotide and thereby improves the sequencing ability of pores formed from the mutant monomer. The principles of host-guest chemistry are well-known in the art. The adaptor has an effect on the physical or chemical properties of the pore that improves its interaction with the nucleotide or polynucleotide. The adaptor may alter the charge of the barrel or channel of the pore or specifically interact with or bind to the nucleotide or polynucleotide thereby facilitating its interaction with the pore.

The molecular adaptor is preferably a cyclic molecule, for example a cyclodextrin, a species that is capable of hybridization, a DNA binder or intercalator, a peptide or peptide analogue, a synthetic polymer, an aromatic planar molecule, a small positively-charged molecule or a small molecule capable of hydrogen-bonding.

The adaptor may be cyclic. A cyclic adaptor preferably has the same symmetry as the pore.

The adaptor typically interacts with the analyte, nucleotide or polynucleotide via host-guest chemistry. The adaptor is typically capable of interacting with the nucleotide or polynucleotide. The adaptor comprises one or more chemical groups that are capable of interacting with the nucleotide or polynucleotide. The one or more chemical groups preferably interact with the nucleotide or polynucleotide by non-covalent interactions, such as hydrophobic interactions, hydrogen bonding, Van der Waal's forces, x-cation interactions and/or electrostatic forces. The one or more chemical groups that are capable of interacting with the nucleotide or polynucleotide are preferably positively charged. The one or more chemical groups that are capable of interacting with the nucleotide or polynucleotide more preferably comprise amino groups. The amino groups can be attached to primary, secondary or tertiary carbon atoms. The adaptor even more preferably comprises a ring of amino groups, such as a ring of 6, 7, 8 or 9 amino groups. The adaptor most preferably comprises a ring of 6 or 9 amino groups A ring of protonated amino groups may interact with negatively charged phosphate groups in the nucleotide or polynucleotide.

The correct positioning of the adaptor within the pore can be facilitated by host-guest chemistry between the adaptor and the pore comprising the mutant monomer. The adaptor preferably comprises one or more chemical groups that are capable of interacting with one or more amino acids in the pore. The adaptor more preferably comprises one or more chemical groups that are capable of interacting with one or more amino acids in the pore via non-covalent interactions, such as hydrophobic interactions, hydrogen bonding, Van der Waal's forces, x-cation interactions and/or electrostatic forces. The chemical groups that are capable of interacting with one or more amino acids in the pore are typically hydroxyls or amines. The hydroxyl groups can be attached to primary, secondary or tertiary carbon atoms. The hydroxyl groups may form hydrogen bonds with uncharged amino acids in the pore. Any adaptor that facilitates the interaction between the pore and the nucleotide or polynucleotide can be used.

Suitable adaptors include, but are not limited to, cyclodextrins, cyclic peptides and cucurbiturils. The adaptor is preferably a cyclodextrin or a derivative thereof. The cyclodextrin or derivative thereof may be any of those disclosed in Eliseev, A. V., and Schneider, H-J. (1994) *J. Am. Chem. Soc.* 116, 6081-6088. The adaptor is more preferably heptakis-6-amino-β-cyclodextrin (am$_7$-βCD), 6-monodeoxy-6-monoamino-β-cyclodextrin (am$_1$-βCD) or heptakis-(6-deoxy-6-guanidino)-cyclodextrin (gu$_7$-βCD). The guanidino group in gu$_7$-βCD has a much higher pKa than the primary amines in am$_7$-βCD and so it more positively charged. This gu$_7$-βCD adaptor may be used to increase the dwell time of the nucleotide in the pore, to increase the accuracy of the residual current measured, as well as to increase the base detection rate at high temperatures or low data acquisition rates.

If a succinimidyl 3-(2-pyridyldithio)propionate (SPDP) crosslinker is used as discussed in more detail below, the adaptor is preferably heptakis(6-deoxy-6-amino)-6-N-mono (2-pyridyl)dithiopropanoyl-β-cyclodextrin (am$_6$amPDP$_1$-βCD).

More suitable adaptors include γ-cyclodextrins, which comprise 8 sugar units (and therefore have eight-fold symmetry). The γ-cyclodextrin may contain a linker molecule or may be modified to comprise all or more of the modified sugar units used in the β-cyclodextrin examples discussed above.

The molecular adaptor is preferably covalently attached to the mutant monomer. The adaptor can be covalently attached to the pore using any method known in the art. The adaptor is typically attached via chemical linkage. If the molecular adaptor is attached via cysteine linkage, the one or more cysteines have preferably been introduced to the mutant by substitution. The mutant monomers of the invention can of course comprise a cysteine residue at one or both of positions 272 and 283. The mutant monomer may be chemically modified by attachment of a molecular adaptor to one or both of these cysteines. Alternatively, the mutant monomer may be chemically modified by attachment of a molecule to one or more cysteines or non-natural amino acids, such as FAz, introduced at other positions.

The reactivity of cysteine residues may be enhanced by modification of the adjacent residues. For instance, the basic groups of flanking arginine, histidine or lysine residues will change the pKa of the cysteines thiol group to that of the more reactive S$^-$ group. The reactivity of cysteine residues may be protected by thiol protective groups such as dTNB. These may be reacted with one or more cysteine residues of the mutant monomer before a linker is attached. The molecule may be attached directly to the mutant monomer. The molecule is preferably attached to the mutant monomer using a linker, such as a chemical crosslinker or a peptide linker.

Suitable chemical crosslinkers are well-known in the art. Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate and 2,5-dioxopyrrolidin-1-yl 8-(pyridin-2-yldisulfanyl)octananoate. The most preferred crosslinker is succinimidyl 3-(2-pyridyldithio)propionate (SPDP). Typically, the molecule is covalently attached to the bifunctional crosslinker before the molecule/crosslinker complex is covalently attached to the mutant monomer but it is also possible to covalently attach the bifunctional crosslinker to the monomer before the bifunctional crosslinker/monomer complex is attached to the molecule.

The linker is preferably resistant to dithiothreitol (DTT). Suitable linkers include, but are not limited to, iodoacetamide-based and Maleimide-based linkers.

In other embodiment, the monomer may be attached to a polynucleotide binding protein This forms a modular sequencing system that may be used in the methods of the invention. Polynucleotide binding proteins are discussed below.

The polynucleotide binding protein may be covalently attached to the mutant monomer. The protein can be covalently attached to the pore using any method known in the art. The monomer and protein may be chemically fused or genetically fused. The monomer and protein are genetically fused if the whole construct is expressed from a single polynucleotide sequence. Genetic fusion of a pore to a polynucleotide binding protein is discussed in International Application No. PCT/GB09/001679 (published as WO 2010/004265).

If the polynucleotide binding protein is attached via cysteine linkage, the one or more cysteines have preferably been introduced to the mutant by substitution. Such substitutions are typically made in loop regions which have low conservation amongst homologues indicating that mutations or insertions may be tolerated. They are therefore suitable for attaching a polynucleotide binding protein. Such substitutions are typically made in residues 1 to 43 and 127 to 297 of SEQ ID NO: 2. The reactivity of cysteine residues may be enhanced by modification as described above.

The polynucleotide binding protein may be attached directly to the mutant monomer or via one or more linkers. The polynucleotide binding protein may be attached to the mutant monomer using the hybridization linkers described in International Application No. PCT/GB10/000132 (published as WO 2010/086602). Alternatively, peptide linkers may be used. Peptide linkers are amino acid sequences. The length, flexibility and hydrophilicity of the peptide linker are typically designed such that it does not to disturb the functions of the monomer and molecule. Preferred flexible peptide linkers are stretches of 2 to 20, such as 4, 6, 8, 10 or 16, serine and/or glycine amino acids. More preferred flexible linkers include (SG)$_1$, (SG)$_2$, (SG)$_3$, (SG)$_4$, (SG)$_5$ and (SG)$_8$ wherein S is serine and G is glycine. Preferred rigid linkers are stretches of 2 to 30, such as 4, 6, 8, 16 or 24, proline amino acids. More preferred rigid linkers include (P)$_{12}$ wherein P is proline.

The mutant monomer may be chemically modified with a molecular adaptor and a polynucleotide binding protein.

Making Mutant Lysenin Monomers

The invention also provides a method of improving the ability of a lysenin monomer comprising the sequence shown in SEQ ID NO: 2 to characterise a polynucleotide. The method comprises making one or more modifications within the region of from about position 44 to about position 126 of SEQ ID NO: 2 which alter the ability of the monomer to interact with a polynucleotide and do not affect the ability of the monomer to form a pore. Any of the embodiments discussed above with reference to the mutant lysenin monomers and below with reference to characterising polynucleotides equally apply to this method of the invention.

Constructs

The invention also provides a construct comprising two or more covalently attached monomers derived from lysenin wherein at least one of the monomers is a mutant lysenin monomer of the invention. The construct of the invention retains its ability to form a pore. One or more constructs of the invention may be used to form pores for characterising a target analyte. One or more constructs of the invention may be used to form pores for characterising a target polynucleotide, such as sequencing a target polynucleotides. The construct may comprise 2, 3, 4, 5, 6, 7, 8, 9 or 10 or more monomers. The two or more monomers may be the same or different.

At least monomer in the construct is a mutant monomer of the invention. The other monomers in the construct do not have to be mutant monomers of the invention. For instance, at least one monomer may comprise the sequence shown in SEQ ID NO. 2. At least one monomer in the construct may be a paralogue or homologue of SEQ ID NO. 2. Suitable homologues are shown in SEQ ID NOs: 16 to 19.

Alternatively, at least one monomer may comprise a variant of SEQ ID NO 2 which is at least 50% homologous to SEQ ID NO: 2 over its entire sequence based on amino acid identity, but does not include any of the specific mutations required by the mutant monomers of the invention. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. The variant may be a fragment or any other variant discussed above. Constructs of the invention may also comprise a variant of SEQ ID NO: 16, 17, 18 or 19 which is at least 50% homologous or at least any of the other level of homology mentioned above to SEQ ID NO: 16, 17, 18 or 19 over its entire sequence based on amino acid identity.

All of the monomers in the construct may be a mutant monomer of the invention. The mutant monomers may be the same or different. In a more preferred embodiment, the construct comprises two monomers and at least one of the monomers is a mutant monomer of the invention.

The monomers may be genetically fused. Monomers are genetically fused if the whole construct is expressed from a single polynucleotide sequence. The coding sequences of the monomers may be combined in any way to form a single polynucleotide sequence encoding the construct. Genetic fusion is discussed in International Application No. PCT/GB09/001679 (published as WO 2010/004265).

The monomers may be genetically fused in any configuration. The monomers may be fused via their terminal amino acids. For instance, the amino terminus of the one monomer may be fused to the carboxy terminus of another monomer.

The two or more monomers may be genetically fused directly together. The monomers are preferably genetically fused using a linker. The linker may be designed to constrain the mobility of the monomers. Preferred linkers are amino acid sequences (i.e. peptide linkers). Any of the peptide linkers discussed above may be used.

In another preferred embodiment, the monomers are chemically fused. Monomers are chemically fused if they are chemically attached, for instance via a chemical crosslinker. Any of the chemical crosslinkers discussed above may be used. The linker may be attached to one or more cysteine residues or non-natural amino acids, such as Faz, introduced into a mutant monomer. Alternatively, the linker may be attached to a terminus of one of the monomers in the construct. Monomers are typically linked via one or more of residues 1 to 43 and 127 to 297 of SEQ ID NO: 2.

If a construct contains different monomers, crosslinkage of monomers to themselves may be prevented by keeping the concentration of linker in a vast excess of the monomers. Alternatively, a "lock and key" arrangement may be used in which two linkers are used. Only one end of each linker may react together to form a longer linker and the other ends of the linker each react with a different monomers. Such linkers are described in International Application No. PCT/GB10/000132 (published as WO 2010/086602).

The invention also provides a method of producing a construct of the invention. The method comprises covalently attaching at least one mutant lysenin monomer of the invention to one or more monomers derived from lysenin. Any of the embodiments discussed above with reference to the construct of the invention equally apply to the methods of producing the constructs.

Polynucleotides

The present invention also provides polynucleotide sequences which encode a mutant monomer of the invention. The mutant monomer may be any of those discussed above. The polynucleotide sequence preferably comprises a sequence at least 50%, 60%, 70%, 80%, 90% or 95% homologous based on nucleotide identity to the sequence of SEQ ID NO. 1 over the entire sequence. There may be at least 80%, for example at least 85%, 90% or 95% nucleotide identity over a stretch of 300 or more, for example 375, 450, 525 or 600 or more, contiguous nucleotides ("hard homology"). Homology may be calculated as described above. The polynucleotide sequence may comprise a sequence that differs from SEQ ID NO: 1 on the basis of the degeneracy of the genetic code.

The present invention also provides polynucleotide sequences which encode any of the genetically fused constructs of the invention. The polynucleotide preferably comprises two or more sequences as shown in SEQ ID NO: 1 or a variant thereof as described above.

Polynucleotide sequences may be derived and replicated using standard methods in the art. Chromosomal DNA encoding wild-type Lysenin may be extracted from a pore producing organism, such as *Eisenia fetida*. The gene encoding the pore monomer may be amplified using PCR involving specific primers. The amplified sequence may then undergo site-directed mutagenesis. Suitable methods of site-directed mutagenesis are known in the art and include, for example, combine chain reaction. Polynucleotides encoding a construct of the invention can be made using well-known techniques, such as those described in Sambrook, J. and Russell, D. (2001). Molecular Cloning: A Laboratory Manual, 3rd Edition. Cold Spring Harbor Laboratory Press, Cold Spring Harbor, NY.

The resulting polynucleotide sequence may then be incorporated into a recombinant replicable vector such as a cloning vector. The vector may be used to replicate the polynucleotide in a compatible host cell. Thus polynucleotide sequences may be made by introducing a polynucleotide into a replicable vector, introducing the vector into a compatible host cell, and growing the host cell under conditions which bring about replication of the vector. The vector may be recovered from the host cell. Suitable host cells for cloning of polynucleotides are known in the art and described in more detail below.

The polynucleotide sequence may be cloned into suitable expression vector. In an expression vector, the polynucleotide sequence is typically operably linked to a control sequence which is capable of providing for the expression of the coding sequence by the host cell. Such expression vectors can be used to express a pore subunit.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different polynucleotide sequences may be introduced into the vector.

The expression vector may then be introduced into a suitable host cell. Thus, a mutant monomer or construct of the invention can be produced by inserting a polynucleotide sequence into an expression vector, introducing the vector into a compatible bacterial host cell, and growing the host cell under conditions which bring about expression of the polynucleotide sequence. The recombinantly-expressed monomer or construct may self-assemble into a pore in the host cell membrane. Alternatively, the recombinant pore produced in this manner may be removed from the host cell and inserted into another membrane. When producing pores comprising at least two different subunits, the different subunits may be expressed separately in different host cells as described above, removed from the host cells and assembled into a pore in a separate membrane, such as a sheep erythrocyte membrane or liposomes containing sphingomyelin.

The vectors may be for example, plasmid, virus or phage vectors provided with an origin of replication, optionally a promoter for the expression of the said polynucleotide sequence and optionally a regulator of the promoter. The vectors may contain one or more selectable marker genes, for example a tetracycline resistance gene Promoters and other expression regulation signals may be selected to be compatible with the host cell for which the expression vector is designed. A T7, trc, lac, ara or $\lambda_L$ promoter is typically used.

The host cell typically expresses the pore subunit at a high level. Host cells transformed with a polynucleotide sequence will be chosen to be compatible with the expression vector used to transform the cell. The host cell is typically bacterial and preferably *Escherichia coli*. Any cell with a λ DE3 lysogen, for example C41 (DE3), BL21 (DE3), JM109 (DE3), B834 (DE3), TUNER, Origami and Origami B, can express a vector comprising the T7 promoter. In addition to the conditions listed above any of the methods cited in Proc Natl Acad Sci U.S.A. 2008 December 30; 105(52): 20647-52 may be used to express the lysenin proteins.

Pores

The invention also provides various pores. The pores of the invention are ideal for characterising analytes. The pores of the invention are especially ideal for characterising, such as sequencing, polynucleotides because they can discriminate between different nucleotides with a high degree of sensitivity. The pores can be used to characterise nucleic acids, such as DNA and RNA, including sequencing the nucleic acid and identifying single base changes. The pores of the invention can even distinguish between methylated and unmethylated nucleotides. The base resolution of pores of the invention is surprisingly high. The pores show almost complete separation of all four DNA nucleotides. The pores can be further used to discriminate between deoxycytidine monophosphate (dCMP) and methyl-dCMP based on the dwell time in the pore and the current flowing through the pore.

The pores of the invention can also discriminate between different nucleotides under a range of conditions. In particular, the pores will discriminate between nucleotides under conditions that are favourable to the characterising, such as sequencing, of polynucleotides. The extent to which the pores of the invention can discriminate between different nucleotides can be controlled by altering the applied potential, the salt concentration, the buffer, the temperature and the presence of additives, such as urea, betaine and DTT. This allows the function of the pores to be fine-tuned, particularly when sequencing. This is discussed in more detail below. The pores of the invention may also be used to identify polynucleotide polymers from the interaction with one or more monomers rather than on a nucleotide by nucleotide basis.

A pore of the invention may be isolated, substantially isolated, purified or substantially purified. A pore of the invention is isolated or purified if it is completely free of any other components, such as lipids or other pores. A pore is substantially isolated if it is mixed with carriers or diluents which will not interfere with its intended use. For instance, a pore is substantially isolated or substantially purified if it is present in a form that comprises less than 10%, less than 5%, less than 2% or less than 1% of other components, such as lipids or other pores. Alternatively, a pore of the invention may be present in a lipid bilayer.

A pore of the invention may be present as an individual or single pore. Alternatively, a pore of the invention may be present in a homologous or heterologous population or plurality of two or more pores.

Homo-Oligomeric Pores

The invention also provides a homo-oligomeric pore derived from lysenin comprising identical mutant monomers of the invention. The monomers are identical in terms of their amino acid sequence. The homo-oligomeric pore of the invention is ideal for characterising, such as sequencing, polynucleotides. The homo-oligomeric pore of the invention may have any of the advantages discussed above. The advantages of specific homo-oligomeric pores of the invention are indicated in the Examples.

The homo-oligomeric pore may contain any number of mutant monomers. The pore typically comprises two or more mutant monomers. One or more of the mutant monomers is preferably chemically modified as discussed above. In other words, one or more of the monomers being chemically modified (and the others not being chemically modified) does not prevent the pore from being homo-oligomeric as long as the amino acid sequence of each of the monomers is identical.

Methods for making lysenin pores are described in the Examples and in Yamaji et al., J. Biol. Chem. 1998: 273(9): 5300-6.

Hetero-Oligomeric Pores

The invention also provides a hetero-oligomeric pore derived from lysenin comprising at least one mutant monomer of the invention, wherein at least one of the monomers differs from the others. The monomer differs from the others in terms of its amino acid sequence. The hetero-oligomeric pore of the invention is ideal for characterising, such as sequencing, polynucleotides. Hetero-oligomeric pores can be made using methods known in the art (e.g. Protein Sci. 2002 July; 11(7): 1813-24).

The hetero-oligomeric pore contains sufficient monomers to form the pore. The monomers may be of any type. The pore typically comprises two or more monomers.

The pore may comprise at least one monomer comprising the sequence shown in SEQ ID NO: 2, a paralogue thereof, a homologue thereof or a variant thereof which does not have a mutation required by the mutant monomers of the invention. Suitable variants are any of those discussed above with reference to the constructs of the invention, including SEQ ID NOs: 2, 16, 17, 18 and 19 and variants thereof. In this embodiment, the remaining monomers are preferably mutant monomers of the invention.

In a preferred embodiment, the pore comprises (a) one mutant monomer of the invention and (b) a sufficient number of identical monomers to form the pore, wherein the mutant monomer in (a) is different from the identical monomers in (b). The identical monomers in (b) preferably comprise the sequence shown in SEQ ID NO: 2, a paralogue thereof, a homologue thereof or a variant thereof which does not have a mutation required by the mutant monomers of the invention.

A hetero-oligomeric pore of the invention preferably comprises only one mutant lysenin monomer of the invention.

In another preferred embodiment, all of the monomers in the hetero-oligomeric pore are mutant monomers of the invention and at least one of them differs from the others.

In all the embodiments discussed above, one or more of the mutant monomers is preferably chemically modified as discussed above. The presence of a chemical modification on one monomer does not result in the pore being hetero-oligomeric. The amino acid sequence of at least one monomer must differ from the sequence(s) of the other monomers. Methods for making pores are discussed in more detail below.

Construct-Containing Pores

The invention also provides a pore comprising at least one construct of the invention. A construct of the invention comprises two or more covalently attached monomers derived from lysenin, wherein at least one of the monomers is a mutant lysenin monomer of the invention. In other words, a construct must contain more than one monomer. At least two of the monomers in the pore are in the form of a construct of the invention. The monomers may be of any type.

A pore typically contains (a) one construct comprising two monomers and (b) a sufficient number of monomers to form the pore. The construct may be any of those discussed above. The monomers may be any of those discussed above, including mutant monomers of the invention.

Another typical pore comprises more than one construct of the invention, such as two, three or four constructs of the invention. Such pores further comprise a sufficient number of monomers to form the pore. The monomer may be any of those discussed above. A further pore of the invention comprises only constructs comprising 2 monomers. A specific pore according to the invention comprises several constructs each comprising two monomers. The constructs may oligomerise into a pore with a structure such that only one monomer from each construct contributes to the pore. Typically, the other monomers of the construct (i.e. the ones not forming the pore) will be on the outside of the pore.

Mutations can be introduced into the construct as described above. The mutations may be alternating, i.e. the mutations are different for each monomer within a two monomer construct and the constructs are assembled as a homo-oligomer resulting in alternating modifications. In other words, monomers comprising MutA and MutB are fused and assembled to form an A-B:A-B:A-B:A-B pore. Alternatively, the mutations may be neighbouring, i.e. identical mutations are introduced into two monomers in a construct and this is then oligomerised with different mutant monomers. In other words, monomers comprising MutA are fused follow by oligomerisation with MutB-containing monomers to form A-A:B:B:B:B:B.

One or more of the monomers of the invention in a construct-containing pore may be chemically-modified as discussed above.

Producing Pores of the Invention

The invention also provides a method of producing a pore of the invention. The method comprises allowing at least one mutant monomer of the invention or at least one construct of the invention to oligomerise with a sufficient number of mutant lysenin monomers of the invention, constructs of the invention or monomers derived from lysenin to form a pore. If the method concerns making a homo-oligomeric pore of the invention, all of the monomers used in the method are mutant lysenin monomers of the invention having the same amino acid sequence. If the method concerns making a hetero-oligomeric pore of the invention, at least one of the monomers is different from the others. Any of the embodiments discussed above with reference to the pores of the invention equally apply to the methods of producing the pores.

A preferred way of making a pore of the invention is disclosed in Example 1.

Methods of Characterising Analytes

The invention provides a method of characterising a target analyte. The method comprises contacting the target analyte with a pore of the invention such that the target analyte moves through the pore. One or more characteristics of the target analyte are then measured as the analyte moves with respect to the pore using standard methods known in the art. One or more characteristics of the target analyte are preferably measured as the analyte moves through the pore. Steps (a) and (b) are preferably carried out with a potential applied across the pore. As discussed in more detail below, the applied potential typically results in the formation of a complex between the pore and a polynucleotide binding protein. The applied potential may be a voltage potential. Alternatively, the applied potential may be a chemical potential. An example of this is using a salt gradient across an amphiphilic layer. A salt gradient is disclosed in Holden et al., J Am Chem Soc. 2007 Jul. 11; 129(27): 8650-5.

The method of the invention is for characterising a target analyte. The method is for characterising at least one analyte. The method may concern characterising two or more analytes. The method may comprise characterising any number of analytes, such as 2, 5, 10, 15, 20, 30, 40, 50, 100 or more analytes.

The target analyte is preferably a metal ion, an inorganic salt, a polymer, an amino acid, a peptide, a polypeptide, a protein, a nucleotide, an oligonucleotide, a polynucleotide, a dye, a bleach, a pharmaceutical, a diagnostic agent, a recreational drug, an explosive or an environmental pollutant. The method may concern characterising two or more analytes of the same type, such as two or more proteins, two or more nucleotides or two or more pharmaceuticals. Alternatively, the method may concern characterising two or more analytes of different types, such as one or more proteins, one or more nucleotides and one or more pharmaceuticals.

The target analyte can be secreted from cells. Alternatively, the target analyte can be an analyte that is present inside cells such that the analyte must be extracted from the cells before the invention can be carried out.

The analyte is preferably an amino acid, a peptide, a polypeptides and/or a protein. The amino acid, peptide, polypeptide or protein can be naturally-occurring or non-naturally-occurring. The polypeptide or protein can include within them synthetic or modified amino acids. A number of different types of modification to amino acids are known in the art. Suitable amino acids and modifications thereof are above. For the purposes of the invention, it is to be understood that the target analyte can be modified by any method available in the art.

The protein can be an enzyme, an antibody, a hormone, a growth factor or a growth regulatory protein, such as a cytokine. The cytokine may be selected from interleukins, preferably IFN-1, IL-1, IL-2, IL-4, IL-5, IL-6, IL-10, IL-12 and IL-13, interferons, preferably IL-$\gamma$, and other cytokines such as TNF-$\alpha$. The protein may be a bacterial protein, a fungal protein, a virus protein or a parasite-derived protein.

The target analyte is preferably a nucleotide, an oligonucleotide or a polynucleotide. A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate, cyclic adenosine monophosphate (CAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP), 5-methyl-2'-deoxycytidine monophosphate, 5-methyl-2'-deoxycytidine diphosphate, 5-methyl-2'-deoxycytidine triphosphate, 5-hydroxymethyl-2'-deoxycytidine monophosphate, 5-hydroxymethyl-2'-deoxycytidine diphosphate and 5-hydroxymethyl-2'-deoxycytidine triphosphate. The nucleotides are preferably selected from AMP, TMP, GMP, UMP, dAMP, dTMP, dGMP or dCMP. The nucleotides may be abasic (i.e. lack a nucleobase). The nucleotides may contain additional modifications. In particular, suitable modified nucleotides include, but are not limited to, 2' amino pyrimidines (such as 2'-amino cytidine and 2'-amino uridine), 2'-hyrdroxyl purines (such as, 2'-fluoro pyrimidines (such as 2'-fluorocytidine and 2' fluoro uridine), hydroxyl pyrimidines (such as 5'-α-P-borano uridine), 2'-O-methyl nucleotides (such as 2'-O-methyl adenosine, 2'-O-methyl guanosine, 2'-O-methyl cytidine and 2'-O-methyl uridine), 4'-thio pyrimidines (such as 4'-thio uridine and 4'-thio cytidine) and nucleotides have modifications of the nucleobase (such as 5-pentynyl-2'-deoxy uridine, 5-(3-aminopropyl)-uridine and 1,6-diaminohexyl-N-5-carbamoylmethyl uridine).

Oligonucleotides are short nucleotide polymers which typically have 50 or fewer nucleotides, such 40 or fewer, 30 or fewer, 20 or fewer, 10 or fewer or 5 or fewer nucleotides. The oligonucleotides may comprise any of the nucleotides discussed above, including the abasic and modified nucleotides. The method of the invention is preferably for characterising a target polynucleotide. A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the target polynucleotide can be oxidized or methylated. One or more nucleotides in the target polynucleotide may be damaged. For instance, the polynucleotide may comprise a pyrimidine dimer. Such dimers are typically associated with damage by ultraviolet light and are the primary cause of skin melanomas. One or more nucleotides in the target polynucleotide may be modified, for instance with a label or a tag. Suitable labels are described above. The target polynucleotide may comprise one or more spacers.

Nucleotides are defined above. Nucleotides present in the polynucleotide typically include, but are not limited to, adenosine monophosphate (AMP), guanosine monophosphate (GMP), thymidine monophosphate (TMP), uridine monophosphate (UMP), cytidine monophosphate (CMP), cyclic adenosine monophosphate (cAMP), cyclic guanosine monophosphate (COMP), deoxyadenosine monophosphate (dAMP), deoxyguanosine monophosphate (dGMP), deoxythymidine monophosphate (dTMP), deoxyuridine monophosphate (dUMP) and deoxycytidine monophosphate (dCMP). The nucleotides are preferably selected from AMP, TMP, GMP, CMP, UMP, dAMP, dTMP, dGMP, dCMP and dUMP.

A nucleotide may be abasic (i.e. lack a nucleobase).

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide may be single stranded or double stranded. At least a portion of the polynucleotide is preferably double stranded. A single stranded polynucleotide may have one or more primers hybridised thereto and hence comprise one or more short regions of double stranded polynucleotide. The primers may be the same type of polynucleotide as the target polynucleotide or may be a different type of polynucleotide.

The polynucleotide can be a nucleic acid, such as deoxyribonucleic acid (DNA) or ribonucleic acid (RNA). The target polynucleotide can comprise one strand of RNA hybridized to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains.

The whole or only part of the target polynucleotide may be characterised using this method. The target polynucleotide can be any length. For example, the polynucleotide can be at least 10, at least 50, at least 100, at least 150, at least 200, at least 250, at least 300, at least 400 or at least 500 nucleotide pairs in length. The polynucleotide can be 1000 or more nucleotide pairs, 5000 or more nucleotide pairs in length or 100000 or more nucleotide pairs in length.

The target analyte, such as a target polynucleotide, is present in any suitable sample. The invention is typically carried out on a sample that is known to contain or suspected to contain the target analyte, such as the target polynucleotide. Alternatively, the invention may be carried out on a sample to confirm the identity of one or more target analytes, such as one or more target polynucleotides, whose presence in the sample is known or expected.

The sample may be a biological sample. The invention may be carried out in vitro on a sample obtained from or extracted from any organism or microorganism. The organism or microorganism is typically archaean, prokaryotic or eukaryotic and typically belongs to one the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

The pore is typically present in a membrane. Any membrane may be used in accordance with the invention. Suitable membranes are well-known in the art. The membrane preferably comprises sphingomyelin. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic molecules may be synthetic or naturally occurring. Non-naturally occurring amphiphiles and amphiphiles which form a monolayer are known in the art and include, for example, blockcopolymers (Gonzalez-Perez et al., Langmuir, 2009, 25, 10447-10450). Block copolymers are polymeric materials in which two or more monomer sub-units that are polymerized together to create a single polymer chain Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer.

The amphiphilic layer may be a monolayer or a bilayer. The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Example. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004127 (published as WO 2009/077734). In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick Suitable graphene layers are disclosed in International Application No. PCT/US2008/010637 (published as WO 2009/035647).

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial lipid bilayer. The layer may comprise other trans-membrane and/or intramembrane proteins as well as other molecules in addition to the pore. Suitable apparatus and conditions are discussed below. The method of the invention is typically carried out in vitro. The analyte, such as a target polynucleotide, may be coupled to the membrane. This may be done using any known method. If the membrane is an amphiphilic layer, such as a lipid bilayer (as discussed in detail above), the analyte, such as a target polynucleotide, is preferably coupled to the membrane via a polypeptide present in the membrane or a hydrophobic anchor present in the membrane. The hydrophobic anchor is preferably a lipid, fatty acid, sterol, carbon nanotube or amino acid.

The analyte, such as a target polynucleotide, may be coupled directly to the membrane. The analyte, such as a target polynucleotide, is preferably coupled to the membrane via a linker. Preferred linkers include, but are not limited to, polymers, such as polynucleotides, polyethylene glycols (PEGs) and polypeptides. If a polynucleotide is coupled directly to the membrane, then some data will be lost as the characterising run cannot continue to the end of the polynucleotide due to the distance between the membrane and the interior of the pore. If a linker is used, then the polynucleotide can be processed to completion. If a linker is used, the linker may be attached to the polynucleotide at any position. The linker is preferably attached to the polynucleotide at the tail polymer.

The coupling may be stable or transient. For certain applications, the transient nature of the coupling is preferred. If a stable coupling molecule were attached directly to either the 5' or 3' end of a polynucleotide, then some data will be lost as the characterising run cannot continue to the end of the polynucleotide due to the distance between the bilayer and the interior of the pore. If the coupling is transient, then when the coupled end randomly becomes free of the bilayer, then the polynucleotide can be processed to completion. Chemical groups that form stable or transient links with the membrane are discussed in more detail below. The analyte, such as a target polynucleotide, may be transiently coupled to an amphiphilic layer, such as a lipid bilayer using cholesterol or a fatty acyl chain. Any fatty acyl chain having a length of from 6 to 30 carbon atoms, such as hexadecanoic acid, may be used.

In preferred embodiments, the analyte, such as a target polynucleotide, is coupled to an amphiphilic layer. Coupling of analytes, such as a target polynucleotide, to synthetic lipid bilayers has been carried out previously with various different tethering strategies. These are summarised in Table 3 below.

TABLE 3

| Attachment group | Type of coupling | Reference |
| --- | --- | --- |
| Thiol | Stable | Yoshina-Ishii, C. and S. G. Boxer (2003). "Arrays of mobile tethered vesicles on supported lipid bilayers." J Am Chem Soc 125(13): 3696-7. |
| Biotin | Stable | Nikolov, V., R. Lipowsky, et al. (2007). "Behavior of giant vesicles with anchored DNA molecules." Biophys J 92(12): 4356-68 |
| Cholesterol | Transient | Pfeiffer, I. and F. Hook (2004). "Bivalent cholesterol-based coupling of oligonucletides to lipid membrane assemblies." J Am Chem Soc 126(33): 10224-5 |
| Lipid | Stable | van Lengerich, B., R. J. Rawle, et al. "Covalent attachment of lipid vesicles to a fluid-supported bilayer allows observation of DNA-mediated vesicle interactions." Langmuir 26(11): 8666-72 |

Polynucleotides may be functionalized using a modified phosphoramidite in the synthesis reaction, which is easily compatible for the addition of reactive groups, such as thiol, cholesterol, lipid and biotin groups. These different attachment chemistries give a suite of attachment options for polynucleotides. Each different modification group tethers the polynucleotide in a slightly different way and coupling is not always permanent so giving different dwell times for the polynucleotide to the bilayer. The advantages of transient coupling are discussed above.

Coupling of polynucleotides can also be achieved by a number of other means provided that a reactive group can be added to the polynucleotide. The addition of reactive groups to either end of DNA has been reported previously. A thiol group can be added to the 5' of ssDNA using polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." *Anal Biochem* 169(2): 376-82).

Alternatively, the reactive group could be considered to be the addition of a short piece of DNA complementary to one already coupled to the bilayer, so that attachment can be achieved via hybridisation. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." *Proc Natl Acad Sci USA* 89(20): 9823-5). Alternatively either ssDNA or dsDNA could be ligated to native dsDNA and then the two strands separated by thermal or chemical denaturation. To native dsDNA, it is possible to add either a piece of ssDNA to one or both of the ends of the duplex, or dsDNA to one or both ends. Then, when the duplex is melted, each single strand will have either a 5' or 3' modification if ssDNA was used for ligation or a modification at the 5' end, the 3' end or both if dsDNA was used for ligation. If the polynucleotide is a synthetic strand, the coupling chemistry can be incorporated during the chemical synthesis of the polynucleotide. For instance, the polynucleotide can be synthesized using a primer a reactive group attached to it.

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. By using an antisense primer that has a reactive group, such as a cholesterol, thiol, biotin or lipid, each copy of the target DNA amplified will contain a reactive group for coupling.

The pore used in the method of the invention is a pore of the invention (i.e. a pore comprising at least one mutant monomer of the invention or at least one construct of the invention). The pore may be chemically modified in any of the ways discussed above. The pore is preferably modified with a covalent adaptor that is capable of interacting with the target analyte as discussed above.

The method is preferably for characterising a target polynucleotide and step (a) comprises contacting the target polynucleotide with the pore and a polynucleotide binding protein and the protein controls the movement of the target polynucleotide through the pore. The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

The polynucleotide binding protein is preferably a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the target sequence and controlling its movement through the pore. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases and topoisomerases, such as gyrases. Suitable enzymes include, but are not limited to, exonuclease I from *E. coli* (SEQ ID NO: 6), exonuclease III enzyme from *E. coli* (SEQ ID NO: 8). RecJ from *T. thermophilus* (SEQ ID NO: 10) and bacteriophage lambda exonuclease (SEQ ID NO: 12) and variants thereof. Three subunits comprising the sequence shown in SEQ ID NO. 10 or a variant thereof interact to form a trimer exonuclease. The enzyme may be Phi29 DNA polymerase (SEQ ID NO: 4) or a variant thereof. The enzyme may be a helicase or derived from a helicase. Typical helicases are Hel308, RecD or XPD, for example Hel308 Mbu (SEQ ID NO: 15) or a variant thereof.

A variant of SEQ ID NOs: 4, 6, 8, 10, 12 or 15 is an enzyme that has an amino acid sequence which varies from that of SEQ ID NO: 4, 6, 8, 10, 12 or 15 and which retains polynucleotide binding ability. The variant may include modifications that facilitate binding of the polynucleotide and/or facilitate its activity at high salt concentrations and/or room temperature.

Over the entire length of the amino acid sequence of SEQ ID NO: 4, 6, 8, 10, 12 or 15, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4, 6, 8, 10, 12 or 15 over the entire sequence. There may be at least 80%, for example at least 85%, 90% or 95%, amino acid identity over a stretch of 200 or more, for example 230, 250, 270 or 280 or more, contiguous amino acids ("hard homology"). Homology is determined as described above. The variant may differ from the wild-type sequence in any of the ways discussed above with reference to SEQ ID NO: 2. The enzyme may be covalently attached to the pore as discussed above.

There are two main strategies for sequencing polynucleotides using nanopores, namely strand sequencing and exonuclease sequencing. The method of the invention may concern either strand sequencing or exonuclease sequencing.

In strand sequencing, the DNA is translocated through the nanopore either with or against an applied potential. Exonucleases that act progressively or processively on double stranded DNA can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

In one embodiment, the method of characterising a target polynucleotide involves contacting the target sequence with a pore and a helicase enzyme. Any helicase may be used in the method. Helicases may work in two modes with respect to the pore. First, the method is preferably carried out using a helicase such that it controls movement of the target sequence through the pore with the field resulting from the applied voltage. In this mode the 5' end of the DNA is first captured in the pore, and the enzyme controls movement of the DNA into the pore such that the target sequence is passed through the pore with the field until it finally translocates through to the trans side of the bilayer. Alternatively, the method is preferably carried out such that a helicase enzyme controls movement of the target sequence through the pore against the field resulting from the applied voltage. In this mode the 3' end of the DNA is first captured in the pore, and the enzyme controls movement of the DNA through the pore such that the target sequence is pulled out of the pore against the applied field until finally ejected back to the cis side of the bilayer.

In exonuclease sequencing, an exonuclease releases individual nucleotides from one end of the target polynucleotide and these individual nucleotides are identified as discussed below. In another embodiment, the method of characterising a target polynucleotide involves contacting the target sequence with a pore and an exonuclease enzyme. Any of the exonuclease enzymes discussed above may be used in the method. The enzyme may be covalently attached to the pore as discussed above.

Exonucleases are enzymes that typically latch onto one end of a polynucleotide and digest the sequence one nucleotide at a time from that end. The exonuclease can digest the polynucleotide in the 5' to 3' direction or 3' to 5' direction. The end of the polynucleotide to which the exonuclease binds is typically determined through the choice of enzyme used and/or using methods known in the art. Hydroxyl groups or cap structures at either end of the polynucleotide may typically be used to prevent or facilitate the binding of the exonuclease to a particular end of the polynucleotide.

The method involves contacting the polynucleotide with the exonuclease so that the nucleotides are digested from the end of the polynucleotide at a rate that allows characterisation or identification of a proportion of nucleotides as discussed above. Methods for doing this are well known in the art. For example, Edman degradation is used to successively digest single amino acids from the end of polypeptide such that they may be identified using High Performance Liquid Chromatography (HPLC). A homologous method may be used in the present invention.

The rate at which the exonuclease functions is typically slower than the optimal rate of a wild-type exonuclease. A suitable rate of activity of the exonuclease in the method of the invention involves digestion of from 0.5 to 1000 nucleotides per second, from 0.6 to 500 nucleotides per second, 0.7 to 200 nucleotides per second, from 0.8 to 100 nucleotides per second, from 0.9 to 50 nucleotides per second or 1 to 20 or 10 nucleotides per second. The rate is preferably 1, 10, 100, 500 or 1000 nucleotides per second. A suitable rate of exonuclease activity can be achieved in various ways. For example, variant exonucleases with a reduced optimal rate of activity may be used in accordance with the invention.

The method of the invention involves measuring one or more characteristics of the target analyte, such as a target polynucleotide. The method may involve measuring two, three, four or five or more characteristics of the target analyte, such as a target polynucleotide. For target polynucleotides, the one or more characteristics are preferably selected from (i) the length of the target polynucleotide, (ii) the identity of the target polynucleotide, (iii) the sequence of the target polynucleotide, (iv) the secondary structure of the target polynucleotide and (v) whether or not the target polynucleotide is modified. Any combination of (i) to (v) may be measured in accordance with the invention.

For (i), the length of the polynucleotide may be measured using the number of interactions between the target polynucleotide and the pore.

For (ii), the identity of the polynucleotide may be measured in a number of ways. The identity of the polynucleotide may be measured in conjunction with measurement of the sequence of the target polynucleotide or without measurement of the sequence of the target polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the target polynucleotide as coming from a particular source.

For (iii), the sequence of the polynucleotide can be determined as described previously Suitable sequencing methods, particularly those using electrical measurements, are described in Stoddart D et al., Proc Natl Acad Sci, 12; 106(19):7702-7, Lieberman K R et al. J Am Chem Soc. 2010; 132(50): 17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the target polynucleotide is modified by methylation, by oxidation, by damage, with one or more proteins or with one or more labels, tags or spacers. Specific modifications will result in specific interactions with the pore which can be measured using the methods described below. For instance, methylcyotsine may be distinguished from cytosine on the basis of the current flowing through the pore during its interaction with each nucleotide.

The invention also provides a method of estimating the sequence of a target polynucleotide. The invention further provides a method of sequencing a target polynucleotide.

A variety of different types of measurements may be made. This includes without limitation: electrical measurements and optical measurements. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined 10 with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12:106(19): 7702-7, Lieberman K R et al, J Am Chem Soc. 2010; 132(50):17961-72, and International Application WO-2000/28312. Alternatively, electrical measurements may be made using a multi-channel system, for example as described in International Application WO-2009/077734 and International Application WO-2011/067559.

In a preferred embodiment, the method comprises:
(a) contacting the target polynucleotide with a pore of the invention and a polynucleotide binding protein such that the target polynucleotide moves through the pore and the binding protein controls the movement of the target polynucleotide through the pore; and
(b) measuring the current passing through the pore as the polynucleotide moves with respect to the pore wherein the current is indicative of one or more characteristics of the target polynucleotide and thereby characterising the target polynucleotide.

The methods may be carried out using any apparatus that is suitable for investigating a membrane/pore system in which a pore is inserted into a membrane. The method may be carried out using any apparatus that is suitable for transmembrane pore sensing. For example, the apparatus comprises a chamber comprising an aqueous solution and a barrier that separates the chamber into two sections. The barrier has an aperture in which the membrane containing the pore is formed.

The methods may be carried out using the apparatus described in International Application No. PCT/GB08/000562 (WO 2008/102120).

The methods may involve measuring the current passing through the pore as the analyte, such as a target polynucleotide, moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the analyte, such as a target polynucleotide, moves with respect to the pore. Suitable conditions for measuring ionic currents through transmembrane protein pores are known in the art and disclosed in the Example. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl) or caesium chloride (CsCl) is typically used. KCl is preferred. The salt concentration may be at saturation. The salt concentration may be 3M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is HEPES. Another suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

The method is typically carried out in the presence of free nucleotides or free nucleotide analogues and an enzyme cofactor that facilitate the action of the polynucleotide binding protein, such as a helicase or an exonuclease. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the helicase to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

The target polynucleotide may be contacted with the pore and the polynucleotide binding protein in any order. In is preferred that, when the target polynucleotide is contacted with the protein and the pore, the target polynucleotide firstly forms a complex with the protein. When the voltage is applied across the pore, the target polynucleotide/protein complex then forms a complex with the pore and controls the movement of the polynucleotide through the pore.

Methods of Identifying an Individual Nucleotide

The present invention also provides a method of characterising an individual nucleotide. In other words, the target analyte is a individual nucleotide. The method comprises contacting the nucleotide with a pore of the invention such that the nucleotide interacts with the pore and measuring the current passing through the pore during the interaction and thereby characterising the nucleotide. The invention therefore involves nanopore sensing of an individual nucleotide. The invention also provides a method of identifying an individual nucleotide comprising measuring the current passing through the pore during the interaction and thereby determining the identity of the nucleotide. Any of the pores of the invention discussed above may be used. The pore is preferably chemically modified with a molecular adaptor as discussed above.

The nucleotide is present if the current flows through the pore in a manner specific for the nucleotide (i.e. if a distinctive current associated with the nucleotide is detected flowing through the pore). The nucleotide is absent if the current does not flow through the pore in a manner specific for the nucleotide.

The invention can be used to differentiate nucleotides of similar structure on the basis of the different effects they have on the current passing through a pore. Individual nucleotides can be identified at the single molecule level from their current amplitude when they interact with the pore. The invention can also be used to determine whether or not a particular nucleotide is present in a sample. The invention can also be used to measure the concentration of a particular nucleotide in a sample.

The pore is typically present in a membrane. The methods may be carried out using any suitable membrane/pore system described above.

An individual nucleotide is a single nucleotide. An individual nucleotide is one which is not bound to another nucleotide or polynucleotide by a nucleotide bond. A nucleotide bond involves one of the phosphate groups of a nucleotide being bound to the sugar group of another nucleotide. An individual nucleotide is typically one which is not bound by a nucleotide bond to another polynucleotide of at least 5, at least 10, at least 20, at least 50, at least 100, at least 200, at least 500, at least 1000 or at least 5000 nucleotides. For example, the individual nucleotide has been digested from a target polynucleotide sequence, such as a DNA or RNA strand. The methods of the invention may be used to identify any nucleotide. The nucleotide can be any of those discussed above.

The nucleotide may be derived from the digestion of a nucleic acid sequence such as ribonucleic acid (RNA) or deoxyribonucleic acid. Nucleic acid sequences can be digested using any method known in the art. Suitable methods include, but are not limited to, those using enzymes or catalysts. Catalytic digestion of nucleic acids is disclosed in Deck et al., Inorg. Chem., 2002; 41: 669-677.

Individual nucleotides from a single polynucleotide may be contacted with the pore in a sequential manner in order to sequence the whole or part of the polynucleotide. Sequencing polynucleotides is discussed in more detail above.

The nucleotide may be contacted with the pore on either side of the membrane. The nucleotide may be introduced to the pore on either side of the membrane. The nucleotide may be contacted with the side of the membrane that allows the nucleotide to pass through the pore to the other side of the membrane. For example, the nucleotide is contacted with an end of the pore, which in its native environment allows the entry of ions or small molecules, such as nucleotides, into the barrel or channel of the pore such that the nucleotide may pass through the pore. In such cases, the nucleotide interacts with the pore and/or adaptor as it passes across the membrane through the barrel or channel of the pore. Alternatively, the nucleotide may be contacted with the side of the membrane that allows the nucleotide to interact with the pore via or in conjunction with the adaptor, dissociate from the pore and remain on the same side of the membrane. The present invention provides pores in which the position of the adaptor is fixed. As a result, the nucleotide is preferably contacted with the end of the pore which allows the adaptor to interact with the nucleotide.

The nucleotide may interact with the pore in any manner and at any site. As discussed above, the nucleotide preferably reversibly binds to the pore via or in conjunction with the adaptor. The nucleotide most preferably reversibly binds to the pore via or in conjunction with the adaptor as it passes through the pore across the membrane. The nucleotide can also reversibly bind to the barrel or channel of the pore via or in conjunction with the adaptor as it passes through the pore across the membrane.

During the interaction between the nucleotide and the pore, the nucleotide affects the current flowing through the pore in a manner specific for that nucleotide. For example, a particular nucleotide will reduce the current flowing through the pore for a particular mean time period and to a particular extent. In other words, the current flowing through the pore is distinctive for a particular nucleotide. Control experiments may be carried out to determine the effect a particular nucleotide has on the current flowing through the pore. Results from carrying out the method of the invention on a test sample can then be compared with those derived from such a control experiment in order to identify a particular nucleotide in the sample or determine whether a particular nucleotide is present in the sample. The frequency at which the current flowing through the pore is affected in a manner indicative of a particular nucleotide can be used to determine the concentration of that nucleotide in the sample. The ratio of different nucleotides within a sample can also be calculated. For instance, the ratio of dCMP to methyl-dCMP can be calculated.

The method may involve the use of the any apparatus, sample or condition discussed above.

Methods of Forming Sensors

The invention also provides a method of forming a sensor for characterising a target polynucleotide. The method comprises forming a complex between a pore of the invention and a polynucleotide binding protein, such as a helicase or an exonuclease. The complex may be formed by contacting the pore and the protein in the presence of the target polynucleotide and then applying a potential across the pore. The applied potential may be a chemical potential or a voltage potential as described above. Alternatively, the complex may be formed by covalently attaching the pore to the protein Methods for covalent attachment are known in the art and disclosed, for example, in International Application Nos. PCT/GB09/001679 (published as WO 2010/004265) and PCT/GB 10/000133 (published as WO 2010/086603). The complex is a sensor for characterising the target polynucleotide. The method preferably comprises forming a complex between a pore of the invention and a helicase. Any of the embodiments discussed above equally apply to this method.

The invention also provides a sensor for characterising a target polynucleotide. The sensor comprises a complex between a pore of the invention and a polynucleotide binding protein. Any of the embodiments discussed above equally apply to the sensor of the invention.

Kits

The present invention also provides a kit for characterising, such as sequencing, a target polynucleotide. The kit comprises (a) a pore of the invention and (b) a polynucleotide binding protein, such as a helicase or an exonuclease. Any of the embodiments discussed above equally applicable to the kits of the invention.

The kits of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotide sequences, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

Apparatus

The invention also provides an apparatus for characterising, such as sequencing, target polynucleotides in a sample. The apparatus may comprise (a) a plurality of pores of the invention and (b) a plurality of polynucleotide binding proteins, such as helicases or exonucleases. The apparatus may be any conventional apparatus for analyte analysis, such as an array or a chip.

The apparatus preferably comprises:

a sensor device that is capable of supporting the plurality of pores and being operable to perform polynucleotide characterising or sequencing using the pores and proteins;

at least one reservoir for holding material for performing the characterising or sequencing;

a fluidics system configured to controllably supply material from the at least one reservoir to the sensor device; and a plurality of containers for receiving respective samples, the fluidics system being configured to supply the samples selectively from the containers to the sensor device.

The apparatus may be any of those described in International Application No. PCT/GB10/000789 (published as WO 2010/122293), International Application No. PCT/GB10/002206 (not yet published) or International Application No. PCT/US99/25679 (published as WO 00/28312).

The following Examples illustrate the invention:

EXAMPLE 1

Pore Production

DNA Synthesis

The polypeptide for lysenin was synthesised at GenScript USA Inc. and cloned into a pT7 vector using NdeI and HindIII restriction sites. Codon for Met (ATG) was placed at the beginning of the DNA for expression purposes and two stop codons (TAA TGA) were placed at the end of the DNA to terminate translation.

Protein Expression and Oligomerisation

Protein was generated by coupled in vitro transcription and translation (IVTT) using an *E. coli* T7-S30 extract system for circular DNA. Protein was expressed in the presence of sphingomyelin (SM) containing lipid vesicles to facilitate oligomerisation upon expression of monomers units. To prepare SM vesicles, 0.5 mL of 25 mg/mL stock solution of SM (Avanti Polar Lipids, Cat No. 860062C) in chloroform was left at 37° C. to evaporate off chloroform. Once chloroform has evaporated, 5 mL of TE buffer (10 mM Tris, 1 mM EDTA, pH 8.0) was added to the vial to solubilise lipids. Mixture was then vortexed for about 1 minute and flash frozen with nitrogen. Lipid mixture was then thawed at 37° C., vortexed and flash frozen again. This was repeated 5-6 times. To generate 100 uL of IVTT protein in the presence of lipid vesicles, 25 μL of prepared SM lipid vesicles were pelleted by spinning at 20,000 g for 10 minutes. Once the supernatant was removed, components of the IVTT kit (Invitrogen Expressway Maxi Expression Module, Cat No. 45-4001), Methionine L-[35S] (Perkin Elmer, product number NEG009A005MC, specific activity: >1000Ci (37.0TBq)/mMole) and DNA template were added to the pellet according to manufacturer's instructions. Briefly. 20 uL of *E. coli* slyD-extract, 20 uL of 2.5×IVPS reaction buffer without amino acids, 1.25 uL of 50 mM amino acids lacking methionine, 0.5 uL of 75 mM methionine, 0.5 uL of Methionine L-[35S], 1.0 uL of T7 enzyme mix, 2.5 uL of DNA template at 400 ng/uL (1 ug) and 4.25 uL of RNase free water were added to the membrane pellet and incubated at 37° C. for 30 minutes. 50 uL of feed buffer containing 25 uL of 2×IVPS feed buffer, 1.25 uL of 50 mM amino acids lacking methionine, 0.5 uL of 75 mM methionine, 0.5 uL of Methionine L-[35S] and 22.75 uL of RNase free water were then added to the mixture and incubated at 37° C. for an additional 90 minutes. Sample was then spun at 20,000 g for 10 minutes and the supernatant removed. 100 uL of Laemmli loading buffer (1×) containing 3×SDS was added to the supernatant. The sample was then subjected to SDS-PAGE electrophoresis on a 7.5% gel.

Protein Purification

The gel was dried at 50° C. for 3 hours onto paper (Whatman 3MM Chr) under a vacuum, and exposed to an X-ray film overnight (about 18 hours) Using the autoradiograph as a template, protein oligomer band was cut from the dried gel. After rehydration in 150 uL TE buffer, the paper was removed. The gel was then crushed using a disposable pestle, and the slurry was filtered through a Costar spin-X centrifuge tube filters (0.22 μm pore CA membrane, product number 8160) by centrifugation at 25,000 g for 10 min. The protein solution (filtrate) was then taken to use in planar lipid bilayer experiments.

Using an analogous procedure to that described above in Example 1, the following lysenin mutants were made and purified:—Lysenin-(E84Q/E85K/E92Q/E97S/D126G/E135S) (SEQ ID NO: 2 with mutations E84Q/E85K/E92Q/E97S/D126G/E135S), Lysenin-(E85K/E92Q/E94S/E97S/D126G) (SEQ ID NO: 2 with mutations E85K/E92Q/E94S/E97S/D126G), Lysenin-(E76S/E85K/E92Q/E97S/D126G) (SEQ ID NO: 2 with mutations E76S/E85K/E92Q/E97S/D126G), Lysenin-(E71S/E85K/E92Q/E97S/D126G) (SEQ ID NO: 2 with mutations E71S/E85K/E92Q/E97S/D126G), Lysenin-(D68S/E85K/E92Q/E97S/D126G) (SEQ ID NO: 2 with mutations D68S/E85K/E92Q/E97S/D126G), Lysenin-(E85K/E92Q/E97S/D126G) (SEQ ID NO: 2 with mutations E85K/E92Q/E97S/D126G), Lysenin-(E84Q/E85K/E92Q/E97S/H103S/D126G) (SEQ ID NO: 2 with mutations E84Q/E85K/E92Q/E97S/H103S/D126G), Lysenin-(E84Q/E85K/M90S/E92Q/E97S/D126G) (SEQ ID NO: 2 with mutations E84Q/E85K/M90S/E92Q/E97S/D126G), Lysenin-(E84Q/Q87S/E85K/E92Q/E97S/D126G) (SEQ ID NO: 2 with mutations E84Q/Q87S/E85K/E92Q/E97S/D126G), Lysenin-(E84Q/E85S/E92Q/E97S/D126G) (SEQ ID NO: 2 with mutations E84Q/E85S/E92Q/E97S/D126G), Lysenin-(E84S/E85K/E92Q/E97S/D126G) (SEQ ID NO: 2 with mutations E84S/E85K/B92Q/E97S/D126G), Lysenin-(H81S/E84Q/E85K/E92Q/E97S/D126G) (SEQ ID NO: 2 with mutations H81S/E84Q/E85K/E92Q/E97S/D126G), Lysenin(Y79S/E84Q/E85K/E92Q/E97S/D126G) (SEQ ID NO: 2 with mutations Y79S/E84Q/E85K/E92Q/E97S/D126G), Lysenin-(F70S/E84Q/E85K/E92Q/E97S/D126G) (SEQ ID NO: 2 with mutations F70S/E84Q/E85K/E92Q/E97S/D126G), Lysenin-(H58S/E84Q/E85K/E92Q/E97S/D126G) (SEQ ID NO: 2 with mutations H58S/E84Q/E85K/E92Q/E97S/D126G), Lysenin-(E92Q/E97S) (SEQ ID NO: 2 with mutations E92Q/E97S), Lysenin-(E84Q/E85K/E92Q/E97S) (SEQ ID NO: 2 with mutations E84Q/E85K/E92Q/E97S), Lysenin-(E84Q/E85K/D126G) (SEQ ID NO: 2 with mutations E84Q/E85K/D126G), Lysenin-(E84Q/E85K/D126G/E167A) (SEQ ID NO: 2 with mutations E84Q/E85K/D126G/E167A), Lysenin-(E92Q/E97S/D126G) (SEQ ID NO: 2 with mutations E92Q/E97S/D126G), Lysenin-(E84D/E85K/E92Q) (SEQ ID NO: 2 with mutations E84D/E85K/E92Q), Lysenin-(E84Q) (SEQ ID NO: 2 with the mutation E84Q), Lysenin-(D126N) (SEQ ID NO: 2 with the mutation D126N), Lysenin-(E92Q) (SEQ ID NO: 2 with the mutation E92Q).

EXAMPLE 2

This Example illustrates that it was possible to observe pore insertion of wild-type lysenin (SEQ ID NO: 2) nanopores into 1,2-diphytanoyl-glycero-3-phosphocholine lipid (DPhPC) bilayers It was not possible to observe DNA capture events or any helicase controlled DNA movement under the experimental conditions tested. The general method and substrate employed throughout this Example is shown in FIG. 1 and described in the figure caption.

Materials and Methods

Primers were designed to amplify a ~400 bp fragment of PhiX174. Each of the 5'-ends of these primers included a 50 nucleotide non-complementary region, either a homopolymeric stretch or repeating units of 10 nucleotide homopolymeric sections. In addition, the 5'-end of the forward primer was "capped" to include four 2'-O-Methyl-Uracil (mU) nucleotides and the 5'-end of the reverse primer was chemically phosphorylated. These primer modifications then allow for the controlled digestion of predominantly only the antisense strand, using lambda exonuclease. The mU capping protects the sense strand from nuclease digestion whilst the PO4 at the 5' of the antisense strand promotes it. Therefore after incubation with lambda exonuclease only the sense strand of the duplex remains intact, now as single stranded DNA (ssDNA). The generated ssDNA was then PAGE purified as previously described.

Figure 2:
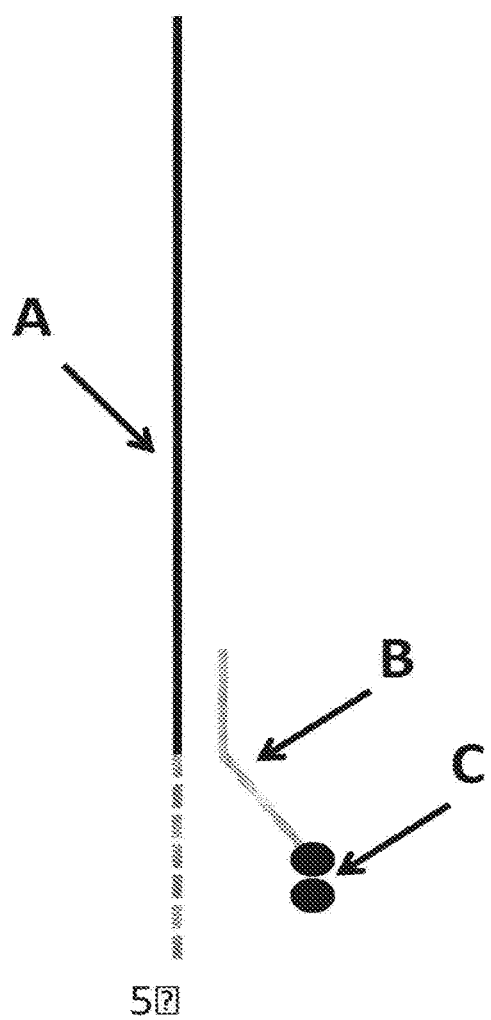
FIG. 2 shows the DNA substrate design used in Examples 1, 2, 3,4, 5 and 6. The DNA substrate consists of a 400 base section of ssDNA from PhiX (SEQ ID NO: 13, labelled A), with a 50T 5'-leader (indicated by the dashed region of strand A) Annealed to this strand just after the 50T leader is a primer (labelled B) containing a 3' cholesterol tag (labelled C) to enrich the DNA on the surface of the bilayer, and thus improve capture efficiency.

The DNA substrate design used in all the experiments described here is shown in FIG. 2. The DNA substrate consists of a 400 base section of ssDNA from PhiX, with a 50T 5'-leader. Annealed to this strand just after the 50T leader is a primer containing a 3' cholesterol tag to enrich the DNA on the surface of the bilayer, and thus improve capture efficiency.

Electrical measurements were acquired from single wild-type lysenin (SEQ ID NO: 2) nanopores inserted in 1,2-diphytanoyl-glycero-3-phosphocholine lipid (DPhPC, Avanti Polar Lipids) bilayers. Bilayers were formed across ~100 μm diameter apertures in 20 μm thick PTFE films (in custom Delrin chambers) via the Montal-Mueller technique, separating two 1 mL buffered solutions. All experiments were carried out in the stated buffered solution. Single-channel currents were measured on Axopatch 200B amplifiers (Molecular Devices) equipped with 1440A digitizers Platinum electrodes were connected to the buffered solutions so that the cis compartment (to which both nanopore and enzyme/DNA are added) is connected to the ground of the Axopatch headstage, and the trans compartment is connected to the active electrode of the headstage.

After achieving a single wild-type lysenin (SEQ ID NO: 2) pore in the bilayer in buffer (625 mM KCl, 100 mM Hepes pH 8.0, 75 mM Potassium Ferrocyanide (II), 25 mM Potassium Ferricyanide (III), 10 mM $MgCl_2$), a control was run at +120 mV for 5 mins. DNA polynucleotide (SEQ ID NO: 13 and 14) and Hel308 Mbu (SEQ ID NO: 15) were added to 50 uL of buffer (625 mM KCl, 100 mM Hepes pH 8.0, 75 mM Potassium Ferrocyanide (II), 25 mM Potassium Ferricyanide (III), 10 mM $MgCl_2$) and pre-incubated for 5 mins (DNA=6 nM, Enzyme (Hel308 Mbu)=2 μM). This pre-incubation mix was added to 950 AL of buffer (625 mM KCl, 100 mM Hepes pH 8.0, 75 mM Potassium Ferrocyanide (II), 25 mM Potassium Ferricyanide (III), 10 mM $MgCl_2$) in the cis compartment of the electrophysiology chamber to try to initiate capture of the helicase-DNA complexes in the lysenin nanopore (to give final concentrations of DNA=0.3 nM, Enzyme (Hel308 Mbu)=100 nM (SEQ ID NO: 15)). Another control was run at +120 mV for 5 mins. Helicase ATPase activity was initiated as required by the addition of NTP (1 mM ATP) to the cis compartment Experiments were carried out at a constant potential of +120 mV.

Results and Discussion

Figure 3:
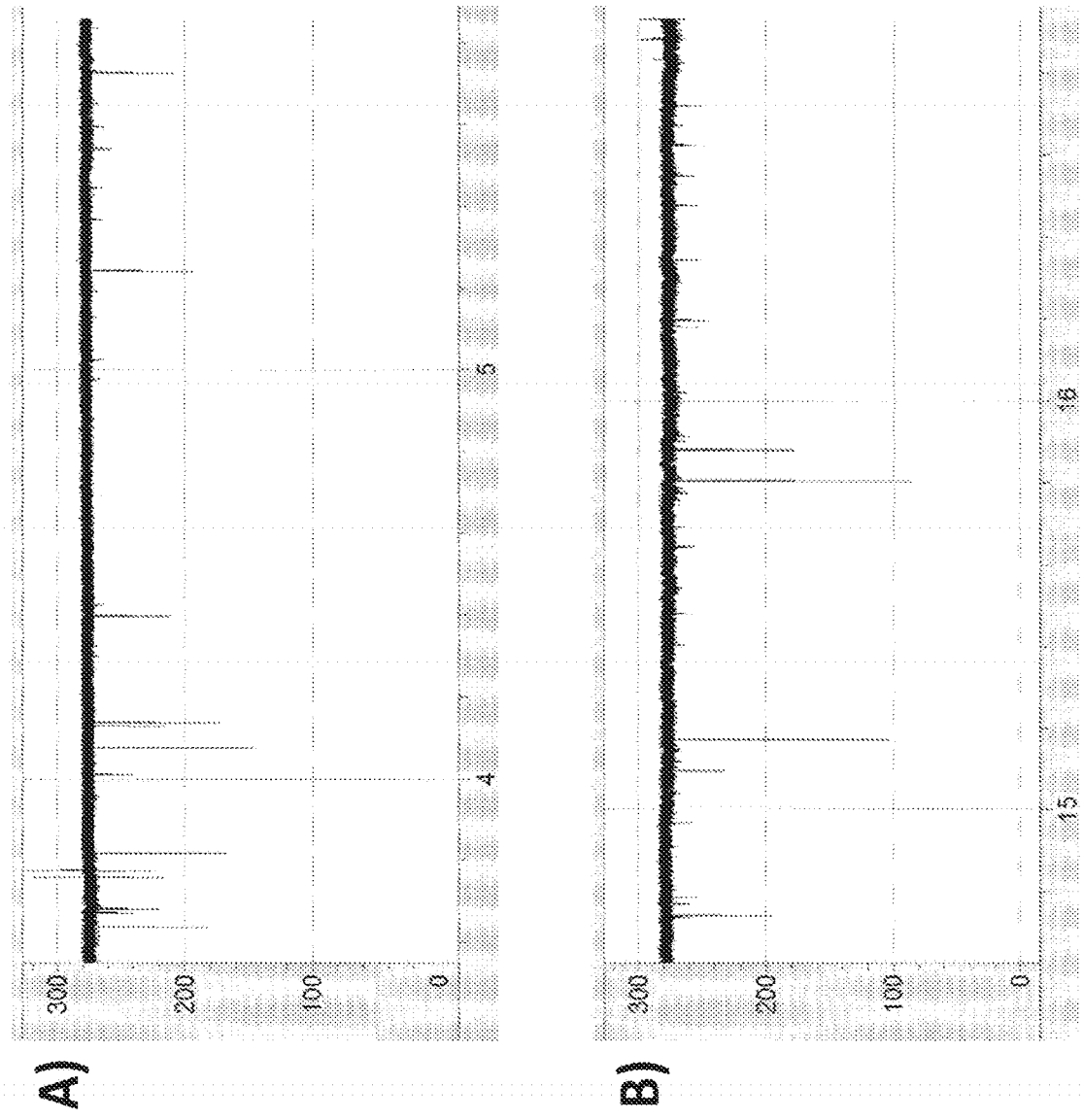
FIG. 3 shows a current trace (y-axis=current (pA), x-axis=time (min) for A and B) of a wild-type lysenin pore inserted into a DPhPC bilayer. A) shows a stable open pore current of approximately +280 pA was observed at +120 mV (625 mM KCl, 100 mM Hepes, pH 8.0, 75 mM Potassium Ferrocyanide (II), 25 mM Potassium Ferricyanide (III), 10 mM $MgCl_2$, wild-type lysenin (SEQ ID NO: 2)) in the absence of DNA and helicase. B) Shows that upon the addition of DNA, helicase and ATP (0.3 nM 400 mer DNA (SEQ ID NO: 13 and 14), Hel308 Mbu, (100 nM, SEQ ID NO: 15), 1 mM ATP) there is no clear DNA capture, and no helicase controlled DNA movement through the nanopore.

It was possible to observe insertion of the WT lysenin (SEQ ID NO: 2) nanopores into the DPhPC bilayer (FIG. 3). A stable open pore current of approximately 280 pA was observed. However, upon the addition of the helicase-DNA substrate mix to the cis compartment no DNA capture events or helicase controlled DNA movement was observed.

EXAMPLE 3

This Example illustrates the use of a Hel308 helicase (Hel308 MBu, SEQ ID NO: 15) to control the movement of intact DNA strands through a mutant lysenin nanopore (Lys-E84D/E85K, SEQ ID NO: 2 with the mutations E84D/E85K). The general method and substrate employed throughout this Example is shown in FIG. 1 and described in the figure caption.

Electrical measurements were acquired as described in Example 2. After achieving a single lysenin-E84D/E85K (SEQ ID NO: 2 with the mutations E84D/E85K) pore in the bilayer under buffered conditions (625 mM KCl, 100 mM Hepes pH 8.0, 75 mM potassium ferrocyanide(II), 25 mM potassium ferricyanide(III)), $MgCl_2$ (10 mM) was added to the cis compartment and a control was run at +120 mV for 5 mins. DNA polynucleotide (SEQ ID NO: 13 and 14) and Hel308 Mbu (SEQ ID NO: 15) were added to 50 μL of buffer (625 mM KCl, 100 mM Hepes pH 8.0, 75 mM potassium ferrocyanide(II), 25 mM potassium ferricyanide(III), 10 mM $MgCl_2$) and pre-incubated for 5 mins (DNA=6 nM, Enzyme=2 μM). This pre-incubation mix was added to 950 μL of buffer (625 mM KCl, 100 mM Hepes pH 8.0, 75 mM potassium ferrocyanide(II), 25 mM potassium ferricyanide (III), 10 mM $MgCl_2$) in the cis compartment of the electrophysiology chamber to initiate capture of the helicase-DNA complexes in the lysenin nanopore (to give final concentrations of DNA=0.3 nM, Enzyme=100 nM (SEQ ID NO: 15)). Another control was run at +120 mV for 10 mins. Helicase ATPase activity was initiated as required by the addition of NTP (1 mM ATP) to the cis compartment. Experiments were carried out at a constant potential of either +120 or +180 mV.

Results and Discussion

Figure 4:
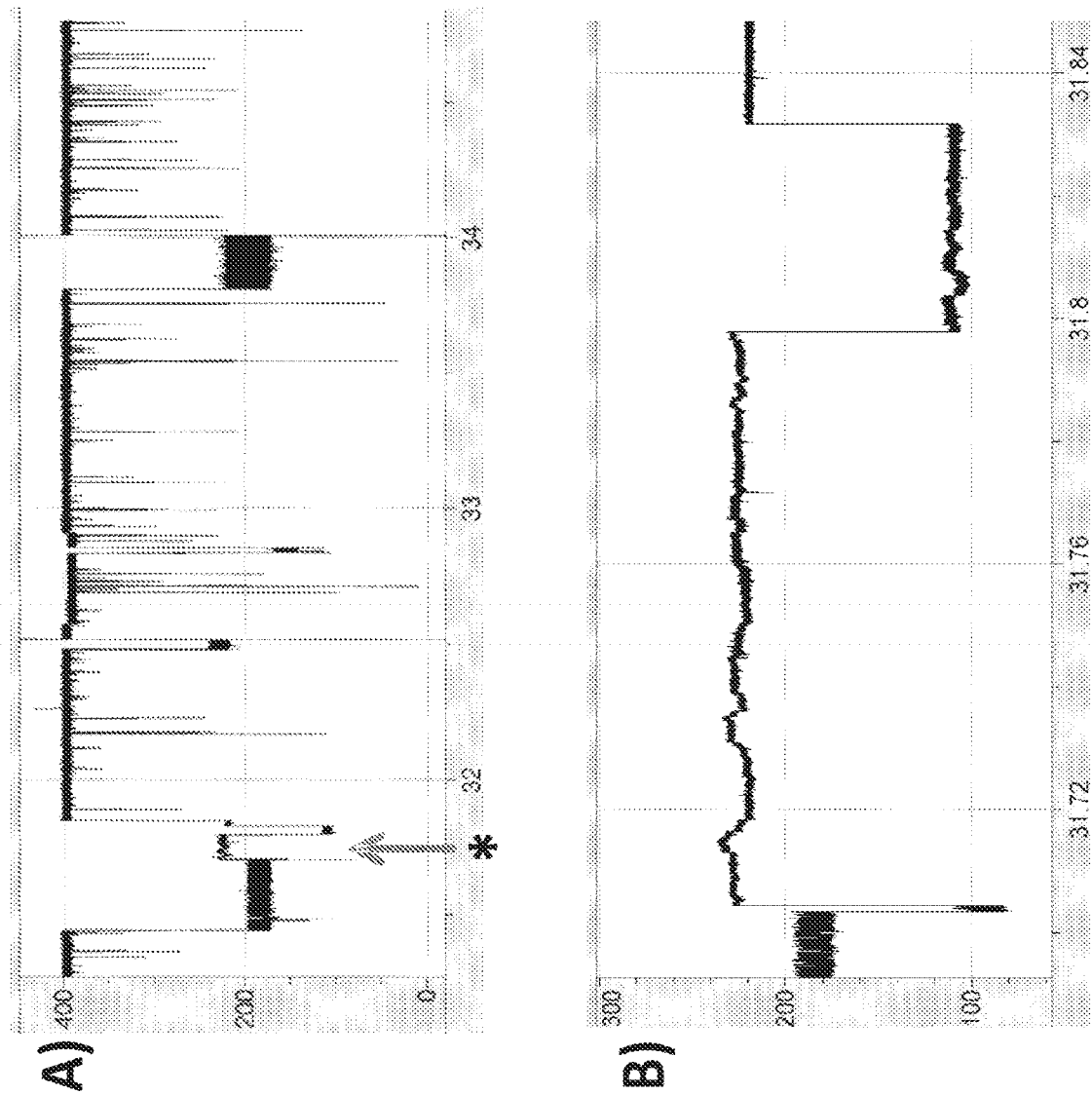
FIG. 4 shows that Hel308 Mbu (SEQ ID NO: 15) was able to move DNA through a lysenin nanopore (lysenin-E84D/E85K, SEQ ID NO: 2 with mutations E84D/E85K) in a controlled fashion, producing stepwise changes in current as the DNA moves through the nanopore. A) Shows an example current trace (y-axis=current (pA), x-axis=time (min)) of DNA capture and Hel308 Mbu controlled 400 mer DNA movement, observed as lower current blocks at ~200 pA from the open-pore level of ~400 pA (180 mV, 625 mM KCl, 100 mM Hepes pH 8.0, 75 mM potassium ferrocyanide (II), 25 mM potassium ferricyanide, 0.3 nM 400 mer DNA (SEQ ID NO: 13 and 14), 100 nM Hel308 Mbu (SEQ ID NO: 15), 1 mM ATP, 10 mM $MgCl_2$, Lysenin-E84D/E85K (SEQ ID NO: 2 with mutations E84D/E85K)). The star indicates helicase controlled DNA movement. Under an applied potential DNA with helicase bound is captured by the lysenin nanopore. This produces blocks in current from the open-pore level (~400 pA) to a DNA level (~220 pA). B) Shows an expanded view (y-axis=current (pA), x-axis=time (min)) of the helicase controlled DNA movement in the upper trace. The DNA level shows stepwise changes in current as the enzyme moves the DNA through the pore.

The addition of Helicase-DNA substrate to Lysenin-E84D/E85K (SEQ ID NO: 2 with the mutations E84D/E85K) as shown in FIG. 1 produces characteristic current blocks as shown in FIG. 4 (at an applied potential of +180 mV). DNA without helicase bound interacts transiently with the nanopore producing short-lived blocks in current (<<1 second). DNA with helicase bound and active (i.e. moving along the DNA strand under ATPase action) produces long characteristic blocks levels with stepwise changes in current as shown in FIG. 4. Different DNA motifs in the nanopore give rise to unique current block levels.

For a given substrate, we observe a characteristic pattern of current transitions that reflects the DNA sequence (examples in FIG. 4). The event range was observed to be approximately 25 pA (at an applied potential of +180 mV).

EXAMPLE 4

This Example illustrates the use of a Hel308 helicase (Hel308 MBu, SEQ ID NO: 15) to control the movement of intact DNA strands through a mutant lysenin nanopore (Lysenin-E92N/E94N/E97N/D121N/D126N, SEQ ID NO: 2 with the mutations E92N/E94N/E97N/D121N/D126N). The general method and substrate employed throughout this Example is shown in FIG. 1 and described in the figure caption.

Electrical measurements were acquired as described in Example 2. After achieving a single lysenin-E92N/E94N/E97N/D121N/D126N (SEQ ID NO: 2 with the mutations E92N/E94N/E97N/D121N/D126N) nanopore in the bilayer under buffered conditions (625 mM KCl, 100 mM Hepes pH 8.0, 75 mM potassium ferrocyanide(II), 25 mM potassium ferricyanide(III)), $MgCl_2$ (10 mM) was added to the cis compartment and a control was run at +120 mV for 5 mins. DNA polynucleotide (SEQ ID NO: 13 and 14) and Hel308 Mbu (SEQ ID NO: 15) were added to 50 μL of buffer (625 mM KCl, 100 mM Hepes pH 8.0, 75 mM potassium ferrocyanide(II), 25 mM potassium ferricyanide(III), 10 mM $MgCl_2$) and pre-incubated for 5 mins (DNA=6 nM, Enzyme=2 μM). This pre-incubation mix was added to 950 μL of buffer (625 mM KCl, 100 mM Hepes pH 8.0, 75 mM potassium ferrocyanide(II), 25 mM potassium ferricyanide (III), 10 mM $MgCl_2$) in the cis compartment of the electrophysiology chamber to initiate capture of the helicase-DNA complexes in the lysenin nanopore (to give final concentrations of DNA=0.3 nM, Enzyme=100 nM). Another control was run at +120 mV for 10 mins. Helicase ATPase activity was initiated as required by the addition of NTP (1 mM ATP) to the cis compartment. Experiments were carried out at a constant potential of +120 mV.

Results and Discussion

Figure 5:
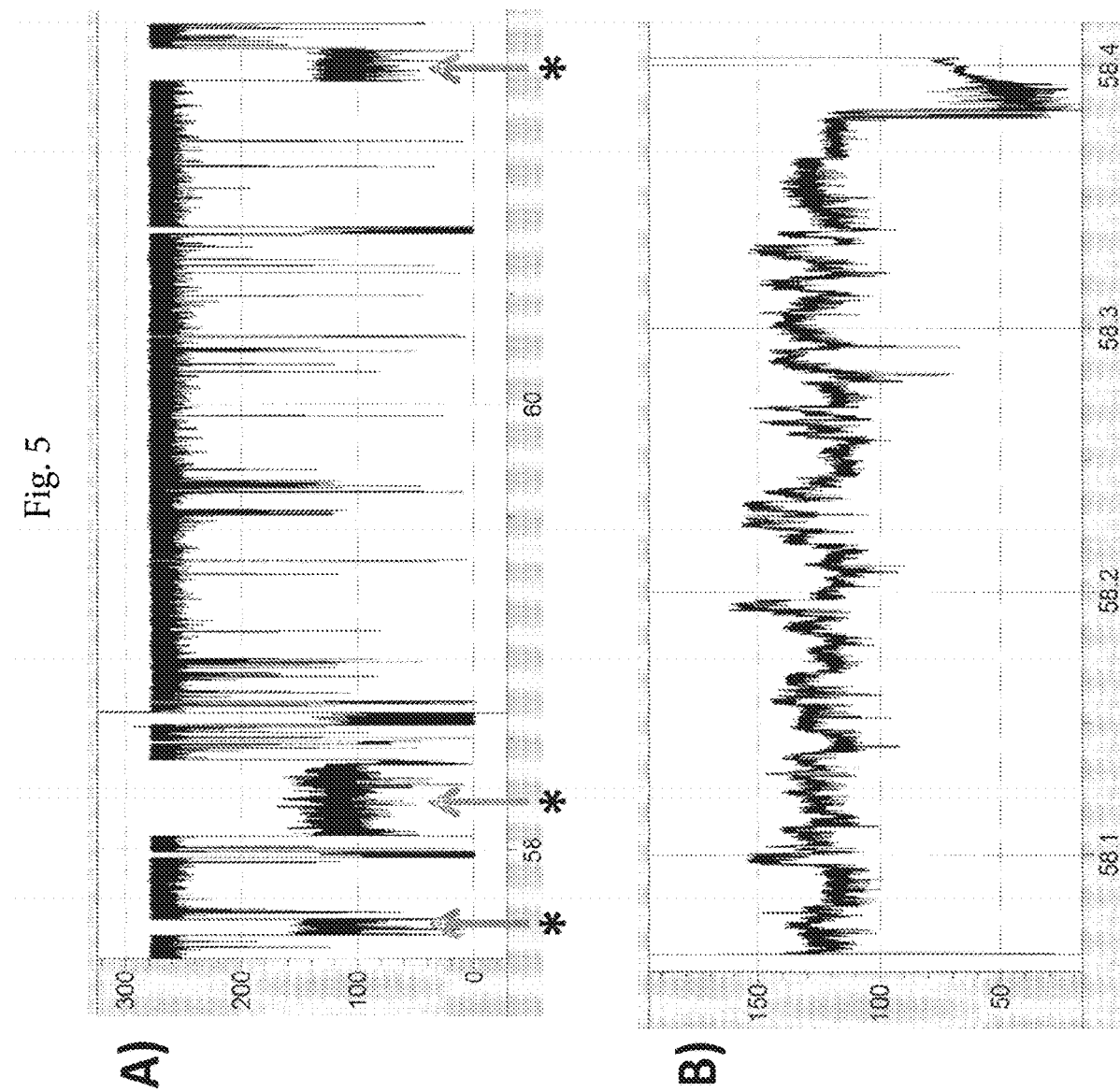
FIG. 5 shows that Hel308 Mbu (SEQ ID NO: 15) was able to move DNA through a lysenin nanopore (Lysenin-E92N/E94N/E97N/D121N/D126N, SEQ ID NO: 2 with mutations E92N/E94N/E97N/D121N/D126N) in a controlled fashion, producing stepwise changes in current as the DNA moves through the nanopore. A) Shows an example current trace (y-axis=current (pA), x-axis=time (min)) of typical Hel308 Mbu controlled 400 mer DNA movements (120 mV, 625 mM KCl, 100 mM Hepes pH 8.0, 75 mM potassium ferrocyanide(II), 25 mM potassium ferricyanide, 0.3 nM 400 mer DNA (SEQ ID NO: 13 and 14), 100 nM Hel308 Mbu (SEQ ID NO: 15), 1 mM ATP, 10 mM $MgCl_2$, Lysenin-E92N/E94N/E97N/D121N/D126N (SEQ ID NO: 2 with mutations E92N/E94N/E97N/D121N/D126N)). Under an applied potential DNA is captured by the lysenin nanopore. This lysenin mutant shows a high level of DNA capture vs. the WT lysenin. DNA captured in the pore produces blocks in current from the open-pore level (~280 pA) to a DNA level (~110 pA). DNA with helicase bound shows stepwise changes in current as the enzyme moves the DNA through the pore. Helicase controlled DNA movements are marked by a star. B) An expanded view of one of the typical helicase controlled DNA movements (y-axis=current (pA), x-axis=time (min) in the upper trace. The DNA level shows stepwise changes in current as the enzyme moves the DNA through the pore.

The addition of Helicase-DNA substrate to Lysenin-E92N/E94N/E97N/D121N/D126N (SEQ ID NO: 2 with the mutations E92N/E94N/E97N/D121N/D126N) as shown in FIG. 1 produces characteristic current blocks as shown in FIG. 5. DNA without helicase bound interacts transiently with the nanopore producing short-lived blocks in current (<<1 second). DNA with helicase bound and active (i.e. moving along the DNA strand under ATPase action) produces long characteristic blocks levels with stepwise changes in current as shown in FIG. 5. Different DNA motifs in the nanopore give rise to unique current block levels. For a given substrate, we observe a characteristic pattern of current transitions that reflects the DNA sequence (examples in FIG. 5). The event range was observed to be approximately 60 pA.

EXAMPLE 5

This Example illustrates the use of a Hel308 helicase (Hel308 MBu, SEQ ID NO: 15) to control the movement of intact DNA strands through a mutant lysenin nanopore (Lysenin-E84Q/E85K/E92Q/E97S/D126G/E167A, SEQ ID NO: 2 with mutations E84Q/E85K/E92Q/E97S/D126G/E167A). The general method and substrate employed throughout this Example is shown in FIG. 1 and described in the figure caption.

Electrical measurements were acquired as described in Example 2. After achieving a single lysenin-E84Q/E85K/E92Q/E97S/D126G/E167A (SEQ ID NO: 2 with mutations E84Q/E85K/E92Q/E97S/D126G/E167A) pore in the bilayer under buffered conditions (625 mM KCl, 100 mM Hepes pH 8.0, 75 mM potassium ferrocyanide(II), 25 mM potassium ferricyanide(III)), MgCl$_2$ (10 mM) was added to the cis compartment and a control was run at +120 mV for 5 mins. Of the 6 mutations, the first 5 (E84Q/E85K/E92Q/E97S/D126G) are made within the region of 44 to 126 in accordance with the invention. The last (E167A) is an additional mutation outside the region as discussed above. DNA polynucleotide (SEQ ID NO: 13 and 14) and Hel308 Mbu (SEQ ID NO: 15) were added to 50 µL of buffer (625 mM KCl, 100 mM Hepes pH 8.0, 75 mM potassium ferrocyanide(II), 25 mM potassium ferricyanide(III), 10 mM MgCl$_2$) and pre-incubated for 5 mins (DNA=12 nM, Enzyme=2 µM). This pre-incubation mix was added to 950 µL of buffer (625 mM KCl, 100 mM Hepes pH 8.0, 75 mM potassium ferrocyanide(II), 25 mM potassium ferricyanide (III), 10 mM MgCl$_2$) in the cis compartment of the electrophysiology chamber to initiate capture of the helicase-DNA complexes in the lysenin nanopore (to give final concentrations of DNA=0.6 nM, Enzyme=100 nM). Another control was run at +120 mV for 10 mins Helicase ATPase activity was initiated as required by the addition of NTP (1 mM ATP) to the cis compartment Experiments were carried out at a constant potential of either +120 or +180 mV.

Results and Discussion

Figure 6:
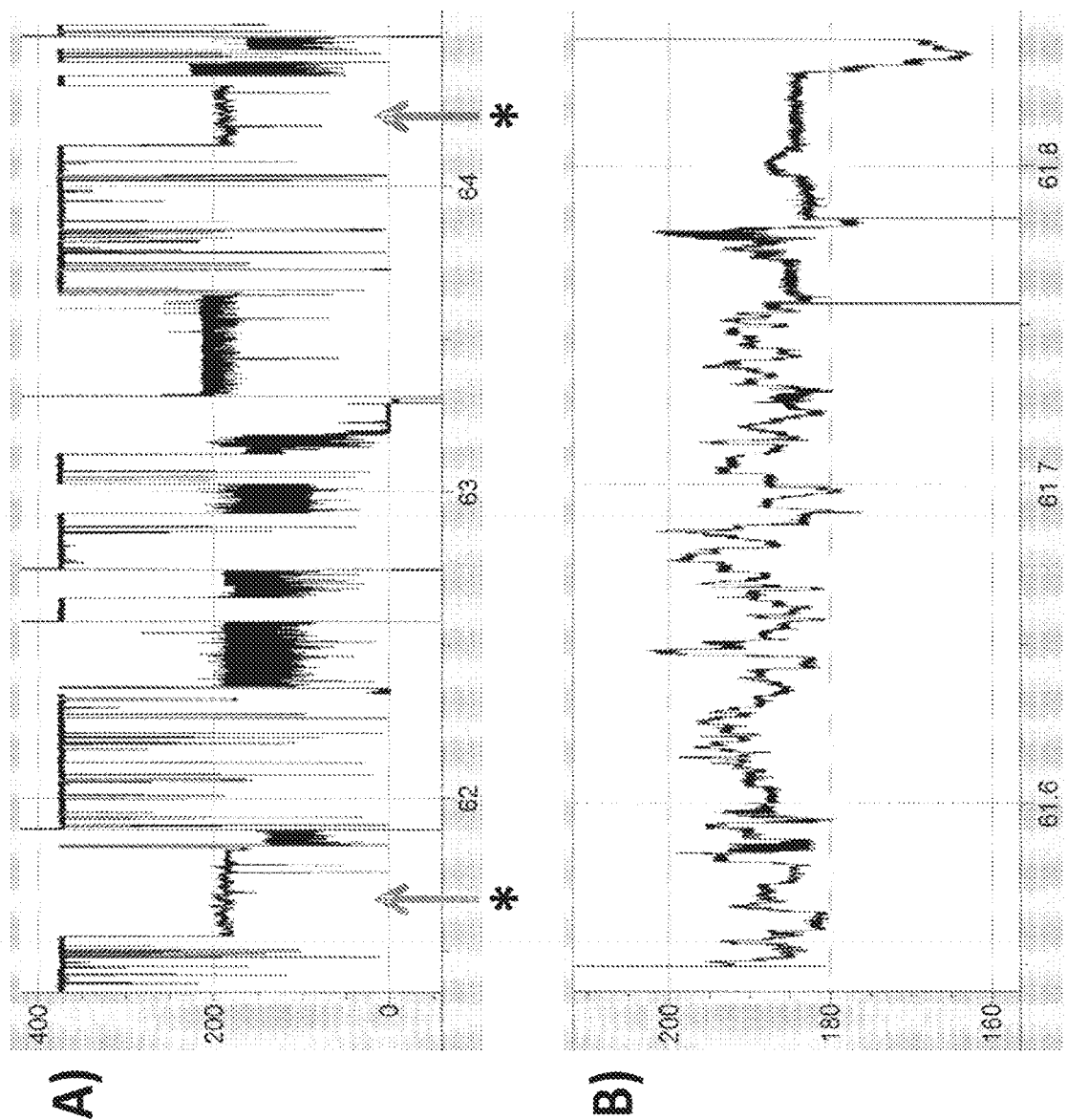
FIG. 6 shows that Hel308 Mbu (SEQ ID NO: 15) was able to move DNA through a lysenin nanopore (Lysenin-E84Q/E85K/E92Q/E97S/D126G/E167A, SEQ ID NO: 2 with mutations E84Q/E85K/E92Q/E97S/D126G/E167A) in a controlled fashion, producing stepwise changes in current as the DNA moves through the nanopore. A) Shows an example current trace (y-axis=current (pA), x-axis=time (min)) of typical Hel308 Mbu controlled DNA movements (180 mV, 625 mM KCl, 100 mM Hepes pH 8.0, 75 mM potassium ferrocyanide(II), 25 mM potassium ferricyanide, 0.6 nM 400 mer DNA (SEQ ID NO: 13 and 14), 100 nM Hel308 Mbu (SEQ ID NO: 15), 1 mM ATP, 10 mM MgCl$_2$, Lysenin-E84Q/E85K/E92Q/E97S/D126G/E167A (SEQ ID NO: 2 with mutations E84Q/E85K/E92Q/E97S/D126G/E167A)). Under an applied potential DNA is captured by the lysenin nanopore. This lysenin mutant shows a high level of DNA capturevs. the WT lysenin. The DNA captured in the pore produces blocks in current from the open-pore level (~390 pA) to a DNA level (~200 pA). DNA with helicase bound shows stepwise changes in current as the enzyme moves the DNA through the pore. Helicase controlled DNA movements are marked by a star. B) An expanded view of one of the typical helicase controlled DNA movements (y-axis=current (pA), x-axis=time (min)) in the upper trace. The DNA level shows stepwise changes in current as the enzyme moves the DNA through the pore.
Figure 7:
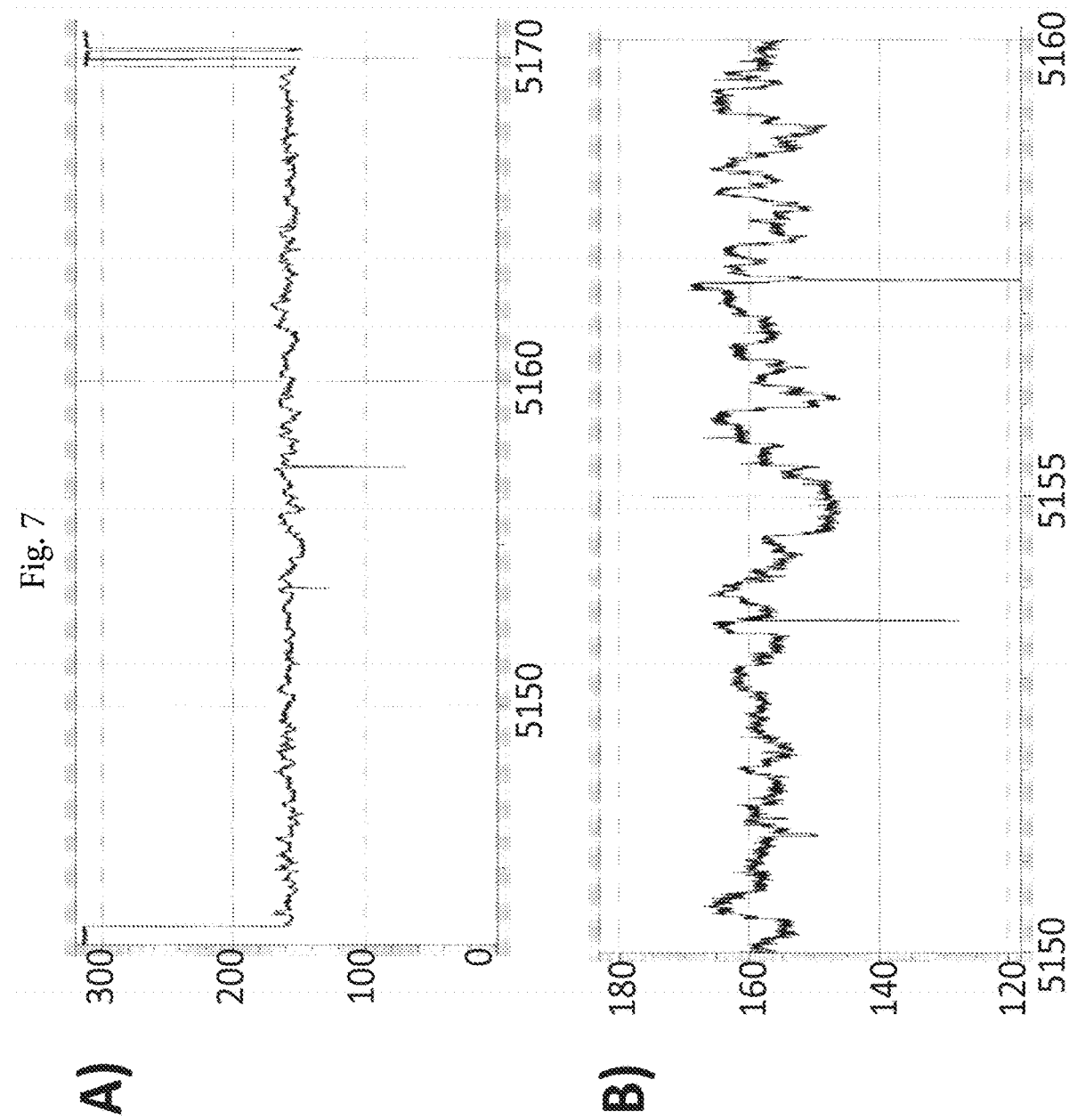
FIG. 7 shows that Hel308 Mbu (SEQ ID NO: 15) was able to move DNA through a lysenin nanopore (Lysenin-E76S/E84Q/E85K/E92Q/E97S/D126G/E167A, SEQ ID NO: 2 with mutations E76S/E84Q/E85K/E92Q/E97S/D126G/E167A) in a controlled fashion, producing stepwise changes in current as the DNA moves through the nanopore. A) Shows an example current trace (y-axis=current (pA), x-axis=time (s)) of a typical Hel308 Mbu controlled DNA movement (+180 mV, 625 mM KCl, 100 mM Hepes pH 8.0, 75 mM potassium ferrocyanide(II), 25 mM potassium ferricyanide(III), pH 8.0, 1 mM ATP, 10 mM MgCl$_2$, 0.6 nM DNA (SEQ ID NO: 13 and 14), 100 nM Hel308 Mbu (SEQ ID NO: 15), Lysenin-E76S/E84Q/E85K/E92Q/E97S/D126G/E167A, SEQ ID NO: 2 with mutations E76S/E84Q/E85K/E92Q/E97S/D126G/E167A)). B) Shows an expanded view of the helicase controlled DNA movement (y-axis=current (pA), x-axis=time (s)) in the upper trace. The DNA level shows stepwise changes in current as the enzyme moves the DNA through the pore.
Figure 8:
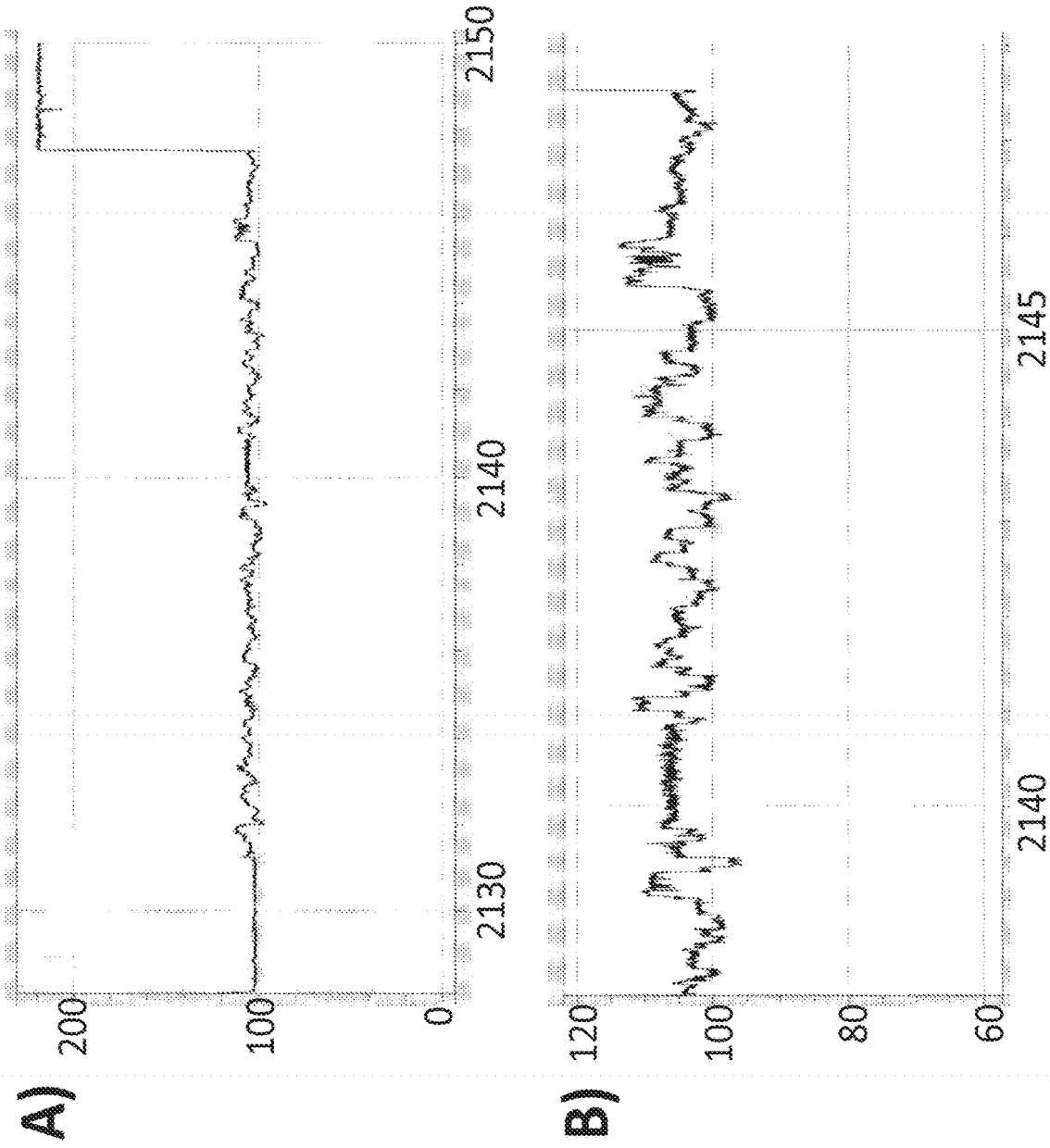
FIG. 8 shows that Hel308 Mbu (SEQ ID NO: 15) was able to move DNA through a lysenin nanopore (Lysenin-E84Q/E85K/E92Q/E97S/D126G/E167A/E50S, SEQ ID NO: 2 with mutations E84Q/E85K/E92Q/E97S/D126G/E167A/E50S) in a controlled fashion, producing stepwise changes in current as the DNA moves through the nanopore. A) Shows an example current trace (y-axis=current (pA), x-axis=time (s)) of a typical Hel308 Mbu controlled DNA movement (+120 mV, 625 mM KCl, 100 mM Hepes pH 8.0, 75 mM potassium ferrocyanide(II), 25 mM potassium ferricyanide(III), pH 8.0, 1 mM ATP, 10 mM MgCl$_2$, 0.3 nM DNA (SEQ ID NO: 13 and 14), 100 nM Hel308 Mbu (SEQ ID NO: 15), Lysenin-E84Q/E85K/E92Q/E97S/D126G/E167A/E50S, SEQ ID NO: 2 with mutations E84Q/E85K/E92Q/E97S/D126G/E167A/E50S)). B) Shows an expanded view of the helicase controlled DNA movement (y-axis=current (pA), x-axis=time (s)) in the upper trace. The DNA level shows stepwise changes in current as the enzyme moves the DNA through the pore.
Figure 9:
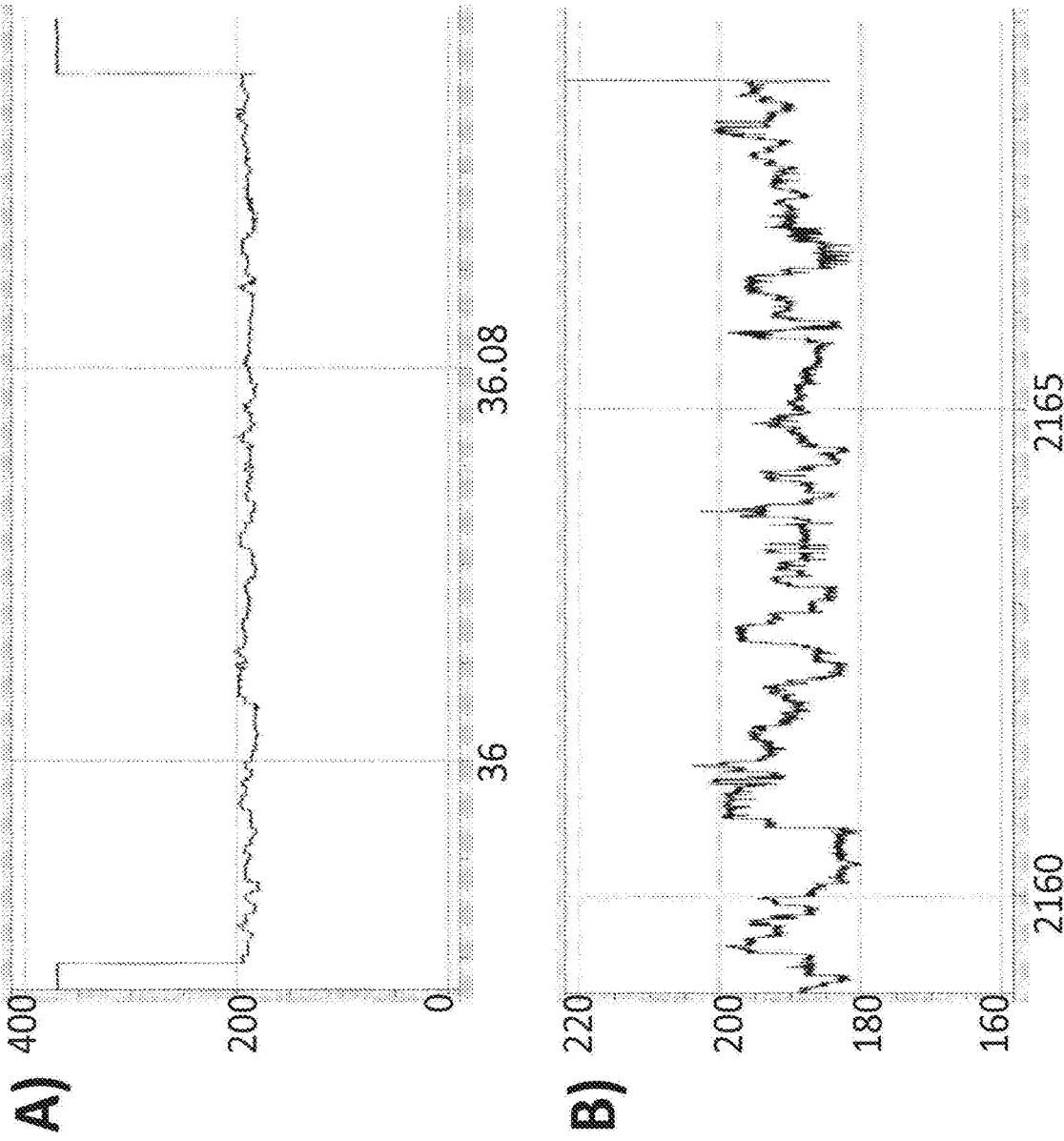
FIG. 9 shows that Hel308 Mbu (SEQ ID NO: 15) was able to move DNA through a lysenin nanopore (Lysenin-E84Q/E85K/E92Q/E97S/D126G/E167A/E71S, SEQ ID NO. 2 with mutations E84Q/E85K/E92Q/E97S/D126G/E167A/E71S) in a controlled fashion, producing stepwise changes in current as the DNA moves through the nanopore. A) Shows an example current trace (y-axis=current (pA), x-axis=time (min)) of a typical Hel308 Mbu controlled DNA movement (+180 mV, 625 mM KCl, 100 mM Hepes pH 8.0, 75 mM potassium ferrocyanide(II), 25 mM potassium ferricyanide(III), pH 8.0, 1 mM ATP, 10 mM MgCl$_2$, 0.3 nM DNA (SEQ ID NO: 13 and 14), 100 nM Hel308 Mbu (SEQ ID NO: 15), Lysenin-E84Q/E85K/E92Q/E97S/D126G/E167A/E71S, SEQ ID NO: 2 with mutations E84Q/E85K/E92Q/E97S/D126G/E167A/E71S). B) Shows an expanded view of the helicase controlled DNA movement (y-axis=current (pA), x-axis=time (s)) in the upper trace. The DNA level shows stepwise changes in current as the enzyme moves the DNA through the pore.
Figure 10:
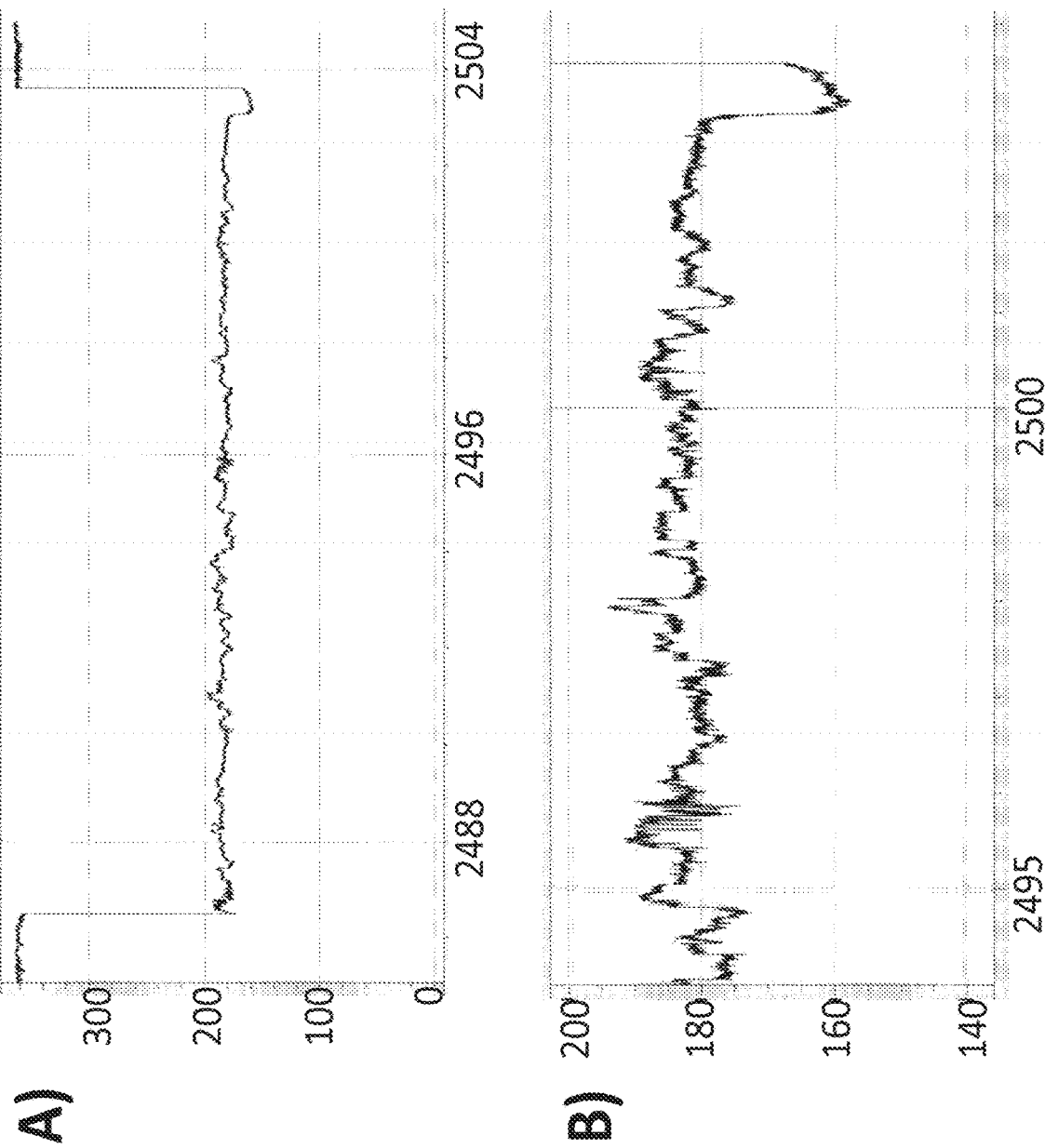
FIG. 10 shows that Hel308 Mbu (SEQ ID NO: 15) was able to move DNA through a lysenin nanopore (Lysenin-E84Q/E85K/E92Q/E97S/D126G/E167A/E128S, SEQ ID NO: 2 with mutations E84Q/E85K/E92Q/E97S/D126G/E167A/E128S) in a controlled fashion, producing stepwise changes in current as the DNA moves through the nanopore. A) Shows an example current trace (y-axis=current (pA), x-axis=time (s)) of a typical Hel308 Mbu controlled DNA movement (+180 mV. 625 mM KCl, 100 mM Hepes pH 8.0, 75 mM potassium ferrocyanide(II), 25 mM potassium ferricyanide(III), pH 8.0, 1 mM ATP, 10 mM MgCl$_2$, 0.6 nM DNA (SEQ ID NO: 13 and 14), 100 nM Hel308 Mbu (SEQ ID NO: 15), Lysenin-E84Q/E85K/E92Q/E97S/D126G/E167A/E128S, SEQ ID NO: 2 with mutations E84Q/E85K/E92Q/E97S/D126G/E167A/E128S). B) Shows an expanded view of the helicase controlled DNA movement (y-axis=current (pA), x-axis=time (s)) in the upper trace. The DNA level shows stepwise changes in current as the enzyme moves the DNA through the pore.
Figure 11:
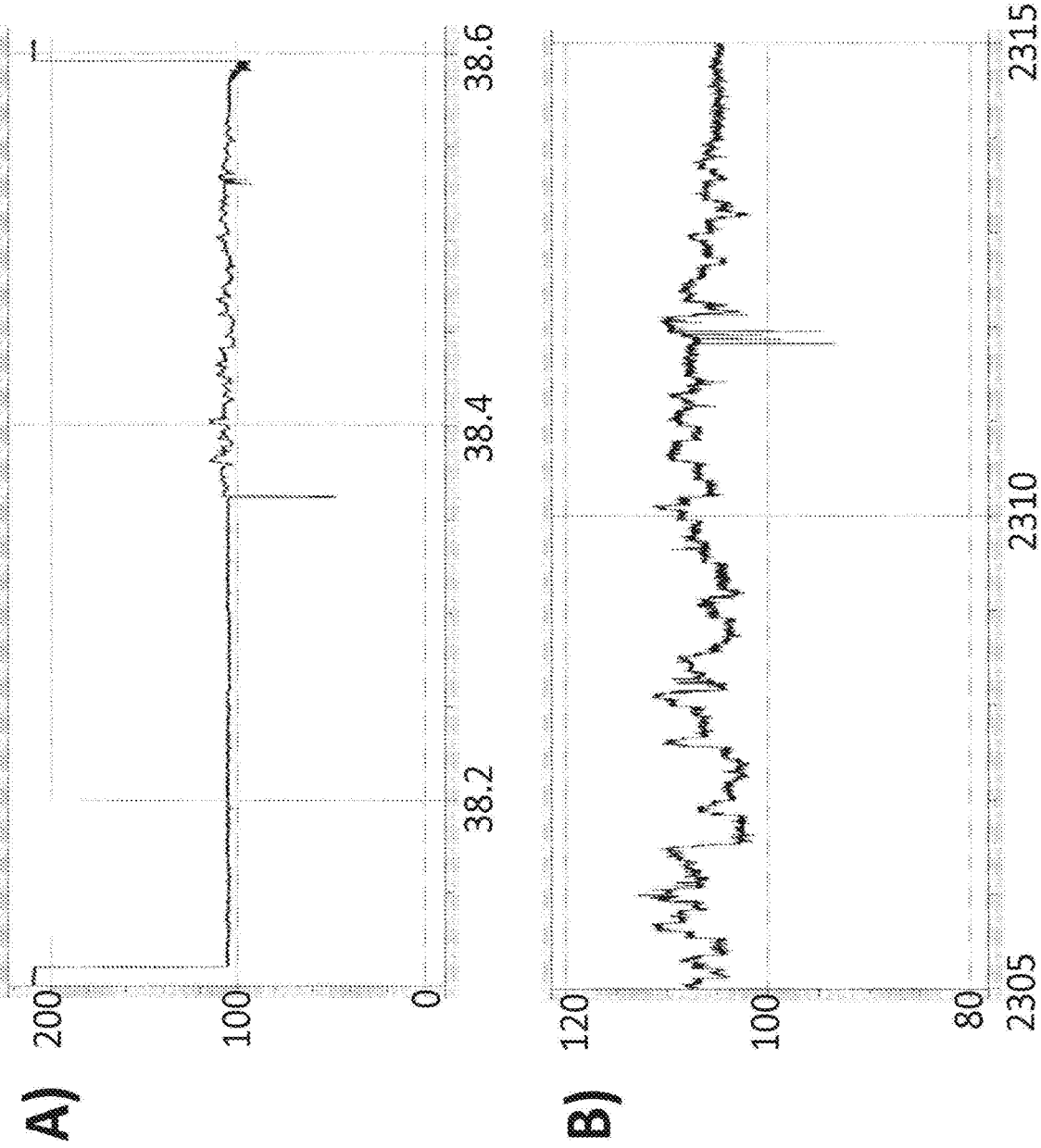
FIG. 11 shows that Hel308 Mbu (SEQ ID NO: 15) was able to move DNA through a lysenin nanopore (Lysenin-E84Q/E85K/E92Q/E97S/D126G/E167A/D68S, SEQ ID NO. 2 with mutations E84Q/E85K/E92Q/E97S/D126G/E167A/D68S) in a controlled fashion, producing stepwise changes in current as the DNA moves through the nanopore. A) Shows an example current trace (y-axis=current (pA), x-axis=time (min)) of a typical Hel308 Mbu controlled DNA movement (+120 mV, 625 mM KCl, 100 mM Hepes pH 8.0, 75 mM potassium ferrocyanide(II), 25 mM potassium ferricyanide(III), pH 8.0, 1 mM ATP, 10 mM MgCl$_2$, 0.3 nM DNA (SEQ ID NO: 13 and 14), 100 nM Hel308 Mbu (SEQ ID NO: 15), Lysenin-E84Q/E85K/E92Q/E97S/D126G/E167A/D68S, SEQ ID NO: 2 with mutations E84Q/E85K/E92Q/E97S/D126G/E167A/D68S). B) Shows an expanded view of the helicase controlled DNA movement (y-axis=current (pA), x-axis=time (s)) in the upper trace. The DNA level shows stepwise changes in current as the enzyme moves the DNA through the pore.
Figure 12:
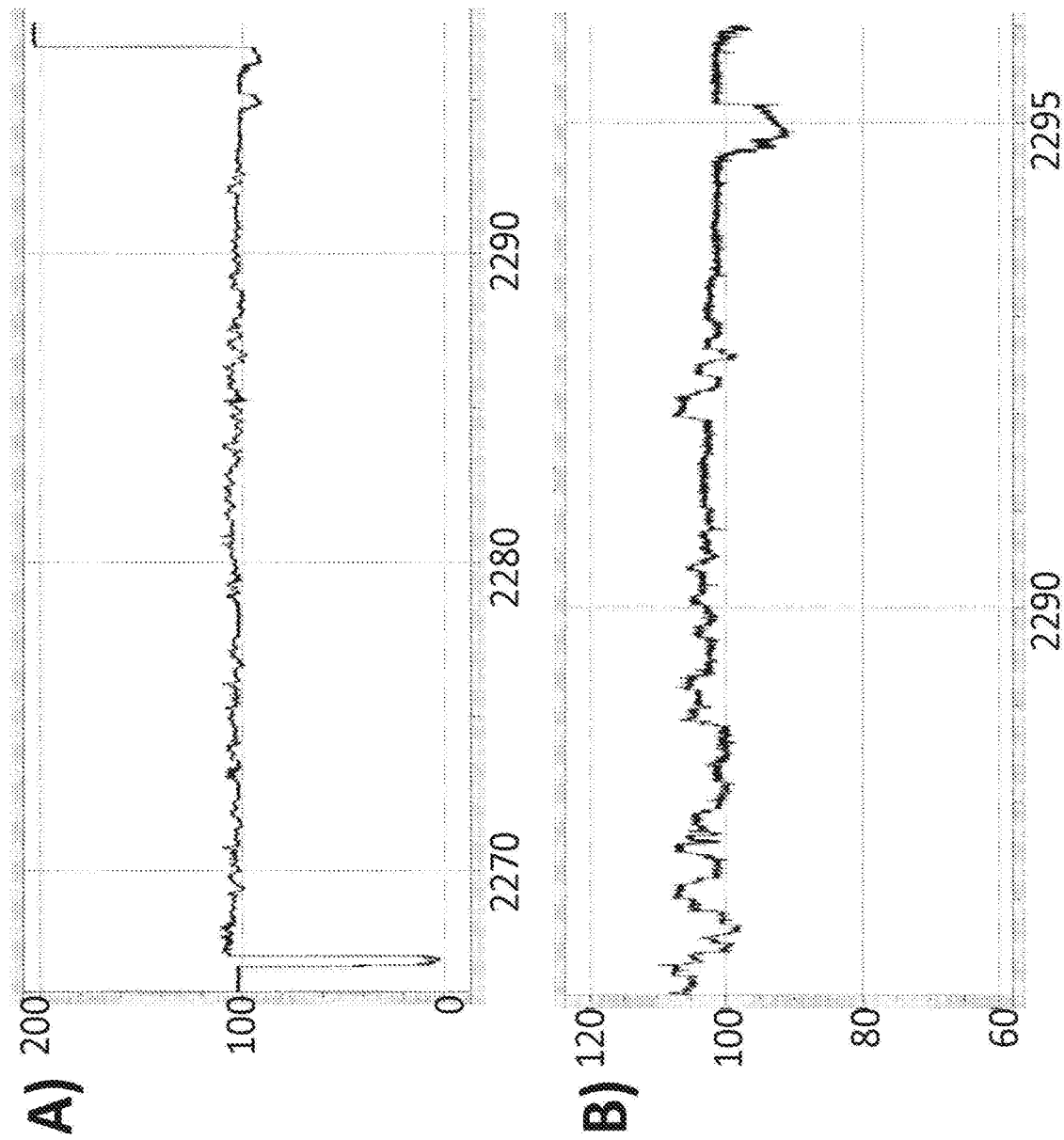
FIG. 12 shows that Hel308 Mbu (SEQ ID NO: 15) was able to move DNA through a lysenin nanopore (Lysenin-E84Q/E85K/E92Q/E97S/D126G/E167A/D121S, SEQ ID NO: 2 with mutations E84Q/E85K/E92Q/E97S/D126G/E167A/D121S) in a controlled fashion, producing stepwise changes in current as the DNA moves through the nanopore. A) Shows an example current trace (y-axis=current (pA), x-axis=time (s)) of a typical a Hel308 Mbu controlled DNA movement (+120 mV, 625 mM KCl, 100 mM Hepes pH 8.0, 75 mM potassium ferrocyanide(II), 25 mM potassium ferricyanide(III), pH 8.0, 1 mM ATP, 10 mM MgCl$_2$, 0.6 nM DNA (SEQ ID NO: 13 and 14), 100 nM Hel308 Mbu (SEQ ID NO: 15), Lysenin-E84Q/E85K/E92Q/E97S/D126G/E167A/D121S, SEQ ID NO: 2 with mutations E84Q/E85K/E92Q/E97S/D126G/E167A/D121S). B) Shows an expanded view of the helicase controlled DNA movement (y-axis=current (pA), x-axis=time (s) in the upper trace. The DNA level shows stepwise changes in current as the enzyme moves the DNA through the pore.

The addition of Helicase-DNA substrate to lysenin nanopore Lysenin-E84Q/E85K/E92Q/E97S/D126G/E167A (SEQ ID NO: 2 with mutations E84Q/E85K/E92Q/E97S/D126G/E167A) as shown in FIG. 1 produces characteristic current blocks as shown in FIG. 6 (at an applied potential of +180 mV). DNA without helicase bound interacts transiently with the nanopore producing short-lived blocks in current (<<1 second). DNA with helicase bound and active (i.e. moving along the DNA strand under ATPase action) produces long characteristic blocks levels with stepwise changes in current as shown in FIG. 6. Different DNA motifs in the nanopore give rise to unique current block levels. For a given substrate, we observe a characteristic pattern of current transitions that reflects the DNA sequence (examples in FIG. 6). The event range was observed to be approximately 30 pA (at an applied potential of +180 mV).

EXAMPLE 6

This Example illustrates the use of a Hel308 helicase (Hel308 MBu, SEQ ID NO: 15) to control the movement of intact DNA strands through a number of different mutant lysenin nanopores (see Table 4 for the list of mutant pores tested). The general method and substrate employed in this Example is shown in FIG. 1 and described in the figure caption.

Electrical measurements were acquired as described in Example 2. After achieving a single lysenin mutant pore in the bilayer (see list of nanopores tested below) under buffered conditions (625 mM KCl, 100 mM Hepes pH 8.0, 75 mM potassium ferrocyanide(II), 25 mM potassium ferricyanide(III)), MgCl$_2$ (10 mM) was added to the cis compartment and a control was run at +120 mV for 5 mins. DNA polynucleotide (SEQ ID NO: 13 and 14) and Hel308 Mbu (SEQ ID NO: 15) were added to 50 µL of buffer (625 mM KCl, 100 mM Hepes pH 8.0, 75 mM potassium ferrocyanide (II), 25 mM potassium ferricyanide(III), pH 8.0, 10 mM MgCl$_2$) and pre-incubated for 5 mins (DNA=12, 6 or 3 nM, Enzyme=2 µM). This pre-incubation mix was added to 950 µL of buffer (625 mM KCl, 100 mM Hepes pH 8.0, 75 mM potassium ferrocyanide(II), 25 mM potassium ferricyanide (III), pH 8.0, 10 mM MgCl$_2$) in the cis compartment of the electrophysiology chamber to initiate capture of the helicase-DNA complexes in the lysenin nanopore (to give final concentrations of DNA=0.6, 0.3 or 0.15 nM, Enzyme=100 nM). Another control was run at +120 mV for 10 mins. Helicase ATPase activity was initiated as required by the addition of NTP (1 mM ATP) to the cis compartment. Experiments were carried out at a constant potential of either +120 mV or +180 mV.

Results and Discussion

The addition of Helicase-DNA substrate (SEQ ID NO: 13 and 14) to single lysenin nanopores (see list of pores in Table 4 below) as shown in FIG. 1 produces characteristic current blocks as shown in FIGS. 7-12 (at an applied potential of +120 or +180 mV). DNA without helicase bound interacts transiently with the nanopore producing short-lived blocks in current (<<1 second). DNA with helicase bound and active (i.e. moving along the DNA strand under ATPase action) produces long characteristic blocks levels with stepwise changes in current as shown in FIG. 7-12 for the various lysenin mutants tested. Different DNA motifs in the nanopore give rise to unique current block levels.

TABLE 4

| Mutant (SEQ ID NO: 2 with the mutations listed in brackets) | Pore insertion | Open pore I (applied potential in brackets) (pA) | Helicase-controlled DNA movement | Applied Potential for Helicase experiments (mV) | DNA Conc. (nM) | Range (pA) |
|---|---|---|---|---|---|---|
| Lysenin-(E85K) | Yes | +277/−186 (+/−120 mV) | Not investigated | / | / | / |
| Lysenin-(E76S) | Yes | +283/−188 (+/−120 mV) | Not under conditions tested | +120 | 0.6 | / |
| Lysenin-(E167A) | Yes | +305/−198 (+/−120 mV) | Not under conditions tested | +120 | 0.6 | / |
| Lysenin-(D35Q) | Yes | +303/−157 (+/−120 mV) | Not under conditions tested | +120 | 0.6 | / |
| Lysenin-(D126Q) | Yes | +302/−196 (+/−120 mV) | Not under conditions tested | +120 | 0.3 | / |
| Lysenin-(E92N) | Yes | +260/−130 (+/−120 mV) | Yes | +120 | 0.3 | / |
| Lysenin-(D121N) | Yes | +299/−194 (+/−120 mV) | Not under conditions tested | +120 | 0.3 | / |
| Lysenin-(E97N) | Yes | +308/−199 (+/−120 mV) | Not under conditions tested | +120 | 0.3 | / |
| Lysenin-(E128N) | Yes | +295/−188 (+/−120 mV) | Not under conditions tested | +120 | 0.3 | / |
| Lysenin-(E94N) | Yes | +151/−275 (+/−120 mV) | Not investigated | / | / | / |
| Lysenin-(E92N/E94N/E97N/D121N/D126N/E128N) | Yes | +260/−135 (+/−120 mV) | Yes | +120 | 0.6 | ~30 |
| Lysenin-(E76S/E84Q/E85K/E92Q/E97S/D126G/E167A) | Yes | +200/−150 (+/−120 mV) | Yes (see FIG. 7) | +180 | 0.6 | ~20 |
| Lysenin-(E84Q/E85K/E92Q/E97S/D126G/E167A/E50S) | Yes | +217/−138 (+/−120 mV) | Yes (see FIG. 8) | +120 | 0.3 | ~20 |
| Lysenin-(E84Q/E85K/E92Q/E97S/D126G/E167A/E71S) | Yes | +223/−144 (+/−120 mV) | Yes (see FIG. 9) | +180 | 0.3 | ~25 |
| Lysenin-(E84Q/E85K/E92Q/E97S/D126G/E167A/E94S) | Yes | +220/140 (+/−120 mV) | Yes | +180 | 0.3 | / |
| Lysenin-(E84Q/E85K/E92Q/E97S/D126G/E167A/E102S) | Yes | +222/−135 (+/−120 mV) | Yes | +180 | 0.3 | / |
| Lysenin-(E84Q/E85K/E92Q/E97S/D126G/E167A/E128S) | Yes | +226/−139 (+/−120 mV) | Yes (see FIG. 10) | +180 | 0.6 | ~20 |
| Lysenin-(E84Q/E85K/E92Q/E97S/D126G/E167A/E135S) | Yes | +249/−153 (+/−120 mV) | Yes | +120 | 0.3 | ~40 |
| Lysenin-(E84Q/E85K/E92Q/E97S/D126G/E167A/D68S) | Yes | +207/−159 (+/−120 mV) | Yes (see FIG. 11) | +120 | 0.3 | ~10 |
| Lysenin-(E84Q/E85K/E92Q/E97S/D126G/E167A/D121S) | Yes | +200/−159 (+/−120 mV) | Yes (see FIG. 12) | +120 | 0.6 | ~15 |
| Lysenin-(E97S) | Yes | +493/−269 (+/−180 mV) | Not under conditions tested | +180 | 0.15 | / |
| Lysenin-(E84Q/E85K) | Yes | +407/−250 (+/−180 mV) | Not under conditions tested | +180 | 0.15 | / |
| Lysenin-(E84Q/E85K/E92Q/D126G/E167A) | Yes | +375/−184 (+/−180 mV) | Yes | +180 | 0.15 | / |
| Lysenin-(E84Q/E85K/E92Q/E97S/D126G) | Yes | +364 (+180 mV) | Yes | +180 | 0.15 | ~12 |
| Lysenin-(E84Q/E85K/E92Q/E97S/E167A) | Yes | +372 (+180 mV) | Yes | +180 | 0.15 | / |

TABLE 4-continued

| Mutant (SEQ ID NO: 2 with the mutations listed in brackets) | Pore insertion | Open pore I (applied potential in brackets) (pA) | Helicase-controlled DNA movement | Applied Potential for Helicase experiments (mV) | DNA Conc. (nM) | Range (pA) |
|---|---|---|---|---|---|---|
| Lysenin-(E84Q/E85K/E97S/D126G/E167A) | Yes | +405/−249 (+/−180 mV) | Yes | +180 | 0.15 | / |
| Lysenin-(E85K/E92Q/E97S/D126G/E167A) | Yes | +448/−190 (+/−180 mV) | Yes | +180 | 0.15 | ~15 |
| Lysenin-(E84Q/E92Q/E97S/D126G/E167A) | Yes | +380 (+180 mV) | Yes | +180 | 0.15 | ~10 |
| Lysenin-(R52S/E84Q/E85K/E92Q/E97S/D126G) | Yes | +222 (+120 mV) | Yes | +120 | 0.15 | ~8 |
| Lysenin-(N48S/E84Q/E85K/E92Q/E97S/D126G) | Yes | +382/−194 (+180 mV) | Yes | +180 | 0.15 | / |
| Lysenin-(N46S/E84Q/E85K/E92Q/E97S/D126G) | Yes | +366 (+180 mV) | Yes | +180 | 0.15 | ~16 |
| Lysenin-(M44S/E84Q/E85K/E92Q/E97S/D126G) | Yes | +369/−184 (+120 mV) | Not under conditions tested | +180 | 0.3 | / |

EXAMPLE 7

This example describes a method of synthesising mutant lysenin nanopores by utilizing *E. coli* expression.

Materials and Methods

*E. coli* Rosetta2(DE3)pLysS cells were transformed with a plasmid containing the construct Strep-TrxEco-TEV-Lysenin, expression was induced with the addition of 0.2 mM IPTG and left overnight at 18° C. The cells were pelleted at 400 rpm for 30 minutes. The cell pellet was resuspended in 1× Bugbuster in 50 mM Tris 300 mM NaCl 0.1 μl/ml benzonase 10 μl/ml Calbiochem set V protease inhibitors and left at 4° C. for 4 hours. The lysate was spun at 20000 rpm for 30 minutes and passed through 0.2 μm filter.

The filtered lysate was loaded onto a Strep Trap column and eluted in 100 mM Tris 300 mM NaCl 10 mM dethiobiotin pH 8.0. The Strep-TrxEco-TEV tag was removed by incubation with Strep tagged TEV protease (1:20 w/w) at 4° C. overnight. Any uncleaved protein, the cleaved tag and TEV protease were removed by incubation with strep beads. The beads were removed by centrifugation and Sphingomyelin (1 mg/ml) was added to the supernatant and left overnight at 37° C.

The invention claimed is:

1. A method of characterising a target analyte, comprising:
 (a) contacting the target analyte with a protein pore such that the target analyte moves through the protein pore, wherein the protein pore comprises at least one lysenin monomer that comprises a barrel-forming region comprising the amino acid sequence as set forth in positions 44 to 126 of SEQ ID NO: 2 with one or more amino acid substitutions, wherein at least one of the amino acid substitutions introduces a cysteine, lysine, or non-natural amino acid; and
 (b) taking one or more measurements as the target analyte moves through the protein pore, wherein the measurements are indicative of one or more characteristics of the target analyte, thereby characterising the target analyte.

2. The method according to claim 1, wherein the target analyte is a metal ion, an inorganic salt, a polymer, an amino acid, a peptide, a polypeptide, a protein, a nucleotide, an oligonucleotide, a polynucleotide, a dye, a bleach, a pharmaceutical, a diagnostic agent, a recreational drug, an explosive or an environmental pollutant.

3. The method according to claim 2, wherein the target analyte is a target polynucleotide.

4. The method according to claim 3, wherein step (a) comprises contacting the target polynucleotide with the protein pore and a polynucleotide binding protein, wherein the polynucleotide binding protein controls the movement of the target polynucleotide through the protein pore.

5. The method according to claim 3, wherein characterising the target polynucleotide comprises determining the sequence of the target polynucleotide.

6. The method according to claim 1, wherein a potential is applied across the protein pore in (b).

7. The method according to claim 6, wherein the potential is a voltage potential or a chemical potential.

8. The method according to claim 1, wherein the method further comprises characterising two or more target analytes, wherein (a) comprises contacting the two or more target analytes with the protein pore such that each of the two or more target analytes move through the protein pore and (b) comprises taking measurements as the two or more target analytes move through the protein pore, wherein the measurements are indicative of one or more characteristics of each of the two or more target analytes.

9. The method according to claim 8, wherein the two or more target analytes are 2, 3, 4, 5, 6, 7, 8, 9, 10, 15, 20, 30, 40, 50, or 100 analytes.

10. The method according to claim 1, wherein the one or more measurements are electrical measurements or optical measurements.

11. The method according to claim 3, wherein the one or more characteristics are selected from (i) the length of the target polynucleotide, (ii) the identity of the target polynucleotide, (iii) the sequence of the target polynucleotide, (iv) the secondary structure of the target polynucleotide and (v) whether or not the target polynucleotide is modified.

12. The method according to claim 1, wherein the cysteine, lysine, or non-natural amino acid is further attached to (i) a polyethylene glycol, a nucleic acid, a dye, a fluorophore, or a chromophore; (ii) a molecular adaptor; or (iii) a polynucleotide binding protein.

13. The method according to claim 12, wherein the cysteine, lysine, or non-natural amino acid is attached to (i), (ii), or (iii) via a linker.

14. The method according to claim 1, wherein the one or more amino acid substitutions (a) alter the steric effect of the monomer, (b) alter the net charge of the monomer, (c) alter the ability of the monomer to hydrogen bond with a polynucleotide, (d) introduce or remove chemical groups that interact through delocalized electron pi systems, (e) alter the structure of the monomer, and/or (f) increase or decrease net positive charge.

15. The method according to claim 1, wherein the one or more substitutions comprise substitution at one or more of the following positions of SEQ ID NO: 2: M44, N46, N48, E50, R52, H58, D68, F70, E71, S74, E76, S78, Y79, S80, H81, S82, E84, E85, S86, Q87, S89, M90, E92, E94, E97, E102, H103, T104, T106, R115, Q117, N119, D121 and D126.

16. The method according to claim 15, wherein the amino acid(s) substituted into the one or more positions are selected from asparagine (N), serine(S), glutamine (Q), arginine (R), glycine (G), tyrosine (Y), aspartic acid (D), leucine (L), lysine (K) or alanine (A).

17. The method according to claim 1, wherein the one or more substitutions comprise one or more of the following amino acid substitutions:
 (a) serine(S) at position 44;
 (b) serine(S) at position 46;
 (c) serine(S) at position 48;
 (d) serine(S) at position 52;
 (e) serine(S) at position 58;
 (f) serine(S) at position 68;
 (g) serine(S) at position 70;
 (h) serine(S) at position 71;
 (i) serine(S) at position 76;
 (j) serine(S) at position 79;
 (k) serine(S) at position 81;
 (l) serine(S), aspartic acid (D) or glutamine (Q) at position 84;
 (m) serine(S) or lysine (K) at position 85;
 (n) serine(S) at position 87;
 (o) serine(S) at position 90;
 (p) asparagine (N) or glutamine (Q) at position 92;
 (q) serine(S) or asparagine (N) at position 94;
 (r) serine(S) or asparagine (N) at position 97;
 (s) serine(S) at position 102;
 (t) serine(S) at position 103;
 (u) asparagine (N) or serine(S) at position 121;
 (v) serine(S) at position 50;
 (w) asparagine (N) or serine(S) at position 94;
 (x) asparagine (N) or serine(S) at position 97;
 (y) serine(S) or asparagine (N) at position 121;
 (z) asparagine (N) or glutamine (Q) or glycine (G) at position 126; and (aa) serine(S) or asparagine (N) at position 128.

18. The method according to claim 17, wherein the one or more substitutions comprises amino acid substitutions selected from the group consisting of:
   i. one or more of E84D and E85K;
   ii. one or more of E84Q, E85K, E92Q, E97S, D126G and E167A;
   iii. one or more of E92N, E94N, E97N, D121N and D126N;
   iv. one or more of E92N, E94N, E97N, D121N, D126N and E128N;
   v. one or more of E76S, E84Q, E85K, E92Q, E97S, D126G and E167A;
   vi. one or more of E84Q, E85K, E92Q, E97S, D126G, E167A and E50S;
   vii. one or more of E84Q, E85K, E92Q, E97S, D126G, E167A and E71S;
   viii. one or more of E84Q, E85K, E92Q, E97S, D126G, E167A and E94S;
   ix. one or more of E84Q, E85K, E92Q, E97S, D126G, E167A and E102S;
   x. one or more of E84Q, E85K, E92Q, E97S, D126G, E167A and E128S;
   xi. one or more of E84Q, E85K, E92Q, E97S, D126G, E167A and E135S;
   xii. one or more of E84Q, E85K, E92Q, E97S, D126G, E167A and D68S;
   xiii. one or more of E84Q, E85K, E92Q, E97S, D126G, E167A and D121S;
   xiv. one or more of E84Q, E85K, E92Q, E97S, D126G, E167 A and D134S; or
   xv. one or more of E84D, E85K and E92Q;
   xvi. one or more of E84Q, E85K, E92Q, E97S, D126G and E135S;
   xvii. one or more of E85K, E92Q, E94S, E97S and D126G;
   xviii. one or more of E76S, E85K, E92Q, E97S and D126G;
   xix. one or more of E71S, E85K, E92Q, E97S and D126G;
   xx. one or more of D68S, E85K, E92Q, E97S and D126G;
   xxi. one or more of E85K, E92Q, E97S and D126G;
   xxii. one or more of E84Q, E85K, E92Q, E97S, H103S and D126G;
   xxiii. one or more of E84Q, E85K, M90S, E92Q, E97S and D126G;
   xxiv. one or more of E84Q, Q87S, E85K, E92Q, E97S and D126G;
   xxv. one or more of E84Q, E85S, E92Q, E97S and D126G;
   xxvi. one or more of E84S, E85K, E92Q, E97S and D126G;
   xxvii. one or more of H81S, E84Q, E85K, E92Q, E97S and D126G;
   xxviii. one or more of Y79S, E84Q, E85K, E92Q, E97S and D126G;
   xxix. one or more of F70S, E84Q, E85K, E92Q, E97S and D126G;
   xxx. one or more of H58S, E84Q, E85K, E92Q, E97S and D126G;
   xxxi. one or more of R52S, E84Q, E85K, E92Q, E97S and D126G;
   xxxii. one or more of N48S, E84Q, E85K, E92Q, E97S and D126G;
   xxxiii. one or more of N46S, E84Q, E85K, E92Q, E97S and D126G;
   xxxiv. one or more of M44S, E84Q, E85K, E92Q, E97S and D126G;
   xxxv. one or more of E92Q and E97S;
   xxxvi. one or more of E84Q, E85K, E92Q and E97S;
   xxxvii. one or more of E84Q and E85K;
   xxxviii. one or more of E84Q, E85K and D126G;
   xxxix. one or more of E84Q, E85K, D126G and E167A;
   xl. one or more of E92Q, E97S and D126G;
   xli. one or more of E84Q, E85K, E92Q, E97S and D126G;
   xlii. one or more of E84Q, E85K, E92Q, E97S and E167A;
   xliii. one or more of E84Q, E85K, E92Q, D126G and E167A;
   xliv. one or more of E84Q, E85K, E97S, D126G and E167A;
   xlv. one or more of E84Q, E92Q, E97S, D126G and E167A;
   xlvi. one or more of E85K, E92Q, E97S, D126G and E167A;
   xlvii. one or more of E84D, E85K and E92Q;
   xlviii. one or more of E84Q, E85K, E92Q, E97S, D126G, E167A and D121S;
   xlix. one or more of E84Q, E85K, E92Q, E97S, D126G, E167A and D68S;
   l. one or more of E84Q, E85K, E92Q, E97S, D126G, E167A and E135S;
   li. one or more of E84Q, E85K, E92Q, E97S, D126G, E167A and E128S;
   lii. one or more of E84Q, E85K, E92Q, E97S, D126G, E167A and E102S;
   liii. one or more of E84Q, E85K, E92Q, E97S, D126G, E167A and E94S;
   liv. one or more of E84Q, E85K, E92Q, E97S, D126G, E167A and E71S;
   lv. one or more of E84Q, E85K, E92Q, E97S, D126G, E167A and E50S;
   lvi. one or more of E76S, E84Q, E85K, E92Q, E97S, D126G and E167 A;
   lvii. one or more of E92N, E94N, E97N, D121N, D126N and E128N;
   lviii. one or more of E92N, E94N, E97N, D121N and D126N; or
   lix. one or more of E84Q, E85K, E92Q, E97S, D126G and E167A.

19. The method according to claim 1, wherein the protein pore is a homo-oligomeric protein pore.

20. The method according to claim 1, wherein the protein pore is a hetero-oligomeric protein pore.

* * * * *

SEQUENCE LISTING

```
Sequence total quantity: 19
SEQ ID NO: 1            moltype = DNA  length = 897
FEATURE                 Location/Qualifiers
source                  1..897
                        mol_type = genomic DNA
                        organism = Eisenia fetida
SEQUENCE: 1
atgagtgcga aggctgctga aggttatgaa caaatcgaag ttgatgtggt tgctgtgtgg    60
aaggaaggtt atgtgtatga aaatcgtggt agtacctccg tggatcaaaa aattaccatc   120
acgaaaggca tgaagaacgt taatagcgaa acccgtacgg tcaccgcgac gcattctatt   180
ggcagtacca tctccacggg tgacgccttt gaaatcggct ccgtggaagt ttcatattcg   240
catagccacg aagaatcaca agtttcgatg accgaaacgg aagtctacga atcaaaagtg   300
attgaacaca ccattacgat cccgccgacc tcgaagttca cgcgctggca gctgaacgca   360
gatgtcggcg gtgctgacat tgaatatatg tacctgacgg atgaagttac cccgattggc   420
ggtacgcaga gtattccgca agtgatcacc tcccgtgcaa aaattatcgt tggtcgccag   480
attatcctgg gcaagaccga aattcgtatc aaacatgctg aacgcaagga atatatgacc   540
gtggttagcc gtaaatcttg gccggcggcc acgctgggtc acagtaaact gtttaagttc   600
gtgctgtacg aagattgggg cggttttcgc atcaaaaccc tgaatacgat gtattctggt   660
tatgaatacg cgtatagctc tgaccagggc ggtatctact tcgatcaagg caccgacaac   720
ccgaaacagc gttgggccat taataagagc ctgccgctgc gccatggtga tgtcgtgacc   780
tttatgaaca aatacttcac gcgttctggt ctgtgctatg atgacggccc ggcgaccaat   840
gtgtattgtc tggataaacg cgaagacaag tggattctgg aagttgtcgg ctaatga     897

SEQ ID NO: 2            moltype = AA   length = 297
FEATURE                 Location/Qualifiers
source                  1..297
                        mol_type = protein
                        organism = Eisenia fetida
```

```
SEQUENCE: 2
MSAKAAEGYE QIEVDVVAVW KEGYVYENRG STSVDQKITI TKGMKNVNSE TRTVTATHSI    60
GSTISTGDAF EIGSVEVSYS HSHEESQVSM TETEVYESKV IEHTITIPPT SKFTRWQLNA   120
DVGGADIEYM YLIDEVTPIG GTQSIPQVIT SRAKIIVGRQ IILGKTEIRI KHAERKEYMT   180
VVSRKSWPAA TLGHSKLFKF VLYEDWGGFR IKTLNTMYSG YEYAYSSDQG GIYFDQGTDN   240
PKQRWAINKS LPLRHGDVVT FMNKYFTRSG LCYDDGPATN VYCLDKREDK WILEVVG     297

SEQ ID NO: 3            moltype = DNA  length = 1830
FEATURE                 Location/Qualifiers
source                  1..1830
                        mol_type = genomic DNA
                        note = bacteriophage phi AR29
                        organism = unidentified
SEQUENCE: 3
atgaaacaca tgccgcgtaa aatgtatagc tgcgcgtttg aaaccacgac caaagtggaa    60
gattgtcgcg tttgggccta tggctacatg aacatcgaag atcattctga atacaaaatc   120
ggtaacagtc tggatgaatt tatggcatgg gtgctgaaag ttcaggcgga tctgtacttc   180
cacaacctga aatttgatgg cgcattcatt atcaactggc tggaacgtaa tggctttaaa   240
tggagcgcgg atggtctgcc gaacacgtat aataccatta tctctcgtat gggccagtgg   300
tatatgattg atatctgcct gggctacaaa ggtaaacgca aaattcatac cgtgatctat   360
gatagcctga aaaactgcc gtttccggtg aagaaaattg cgaaagattt caaactgacg   420
gttctgaaag gcgatattga ttatcacaaa gaacgtccgg ttggttacaa atacccccg   480
gaagaatacg catacatcaa aaacgatatc cagatcatcg cagaagcgct gctgattcag   540
tttaaacagg gcctggatcg catgaccgcg ggcagtgata gcctgaaagg tttcaaagat   600
atcatcacga ccaaaaaatt caaaaagtg ttcccgacgc tgagcctggg tctggataaa   660
gaagttcgtt atgcctaccg cggcggtttt acctggctga cctgcgtgtttt caaagaaaaa   720
gaaattggcg agggtatggt gtttgatgtt aatagtctgt atccggcaca gatgtacagc   780
cgcctgctgc cgtatggcga accgatcgtt ttcgagggta aatatgtttg ggatgaagat   840
tacccgctgc atattcagca catccgttgt gaatttgaac tgaaagaagg ctatattccg   900
accattcaga tcaaacgtag tcgcttctat aagggtaacg aataccttaa aagctctgga   960
ggtgaaatcg cggatctgtg gctgagtaac gtggatctgg aactgatgaa agaacactac  1020
gatctgtaca acgttaata tcagcggc ctgaaattta aagccacgac cggtctgttc   1080
aaagatttca tcgataaatg gacctacatc aaaacgacct ctgaaggcgc gattaaacag  1140
ctggccaaac tgatgctgaa cagcctgtat ggcaaattcg cctctaatcc ggatgtgacc  1200
ggtaaagttc cgtacctgaa agaaaatggc gcactgggtt ttcgcctggg cgaagaagaa  1260
acgaaagatc cggtgtatac cccgatgggg gttttcatta cggcctggcg acgttacacg  1320
accatcaccg cggcccaggc atgctatgat cgcattatct actgtgatac cgattctatt  1380
catctgacgg gcaccgaaat cccggatgtg attaaagata tcgttgatcc gaaaaaactg  1440
ggttattggg cccacgaaag tacgtttaaa cgtgcaaaat acctgcgcca gaaacctac  1500
atccaggata tctacatgaa agaagtggat ggcaaactgg ttgaaggttc tccggatgat  1560
tacaccgata tcaaattcag tgtgaaatgc gccggcatga cggataaaat caaaaaagaa  1620
gtgaccttcg aaaaacttcaa agttggtttc agccgcaaaa tgaaaccgaa accggtgcag  1680
gttccgggcg gtgtggttct ggtggatgat acgtttacca ttaaatctgg cggtagtgcg  1740
tggagccatc cgcagttcga aaaaggcggt ggctctggtg gcggttctgg cggtagtgcc  1800
tggagccacc cgcagtttga aaataataa                                    1830

SEQ ID NO: 4            moltype = AA  length = 608
FEATURE                 Location/Qualifiers
source                  1..608
                        mol_type = protein
                        note = bacteriophage phi AR29
                        organism = unidentified
SEQUENCE: 4
MKHMPRKMYS CAFETTTKVE DCRVWAYGYM NIEDHSEYKI GNSLDEFMAW VLKVQADLYF    60
HNLKFDGAFI INWLERNGFK WSADGLPNTY NTIISRMGQW YMIDICLGYK GKRKIHTVIY   120
DSLKKLPFPV KKIAKDFKLT VLKGDIDYHK ERPVGYKITP EEYAYIKNDI QIIAEALLIQ   180
FKQGLDRMTA GSDSLKGFKD IITTKKFKKV FPTLSLGLDK EVRYAYRGGF TWLNDRFKEK   240
EIGEGMVFDV NSLYPAQMYS RLLPYGEPIV FEGKYVWDED YPLHIQHIRC EFELKEGYIP   300
TIQIKRSRFY KGNEYLKSSG GEIADLWLSN VDLELMKEHY DLYNVEYISG LKFKATTGLF   360
KDFIDKWTYI KTTSEGAIKQ LAKLMLNSLY GKFASNPDVT GKVPYLKENG ALGFRLGEEE   420
TKDPVYTPMG VFITAWARYT TITAAQACYD RIIYCDTDSI HLTGTEIPDV IKDIVDPKKL   480
GYWAHESTFK RAKYLRQKTY IQDIYMKEVD GKLVEGSPDD YTDIKFSVKC AGMTDKIKKE   540
VTFENFKVGF SRKMKPKPVQ VPGGVVLVDD TFTIKSGGSA WSHPQFEKGG GSGGGSGGSA   600
WSHPQFEK                                                           608

SEQ ID NO: 5            moltype = DNA  length = 1390
FEATURE                 Location/Qualifiers
source                  1..1390
                        mol_type = genomic DNA
                        organism = Escherichia coli
SEQUENCE: 5
atgatgaacg atggcaaaca gcagagcacc ttcctgtttc atgattatga aaccttcggt    60
acccatccgg ccctggatcg tccggcgcag tttgcggcca ttcgcaccga tagcgaattc   120
aatgtgattg gcgaaccgga agtgtttat tgcaaacgtc cgatgatta tctgccgcag   180
ccgggtgcgg tgctgattac cggtattacc ccgcaggaag cgcgcgcgaa aggtgaaaac   240
gaagcggcgt tgccgcgcgc cattcatagc ctgtttaccg tgccgaaaac ctgcattctg   300
ggctataaca atgtgcgctt cgatgatgaa gttacccgta atatctttta tcgtaacttt   360
tatgatccgt atgcgtggag ctggcagcat gataacagcc gttgggatct gctggatgtg   420
atgcgcgcgt gctatgcgct gcgcccggaa ggcattaatt ggccggaaaa cgatgatggc   480
```

```
ctgccgagct ttcgtctgga acatctgacc aaagccaacg gcattgaaca tagcaatgcc    540
catgatgcga tggccgatgt ttatgcgacc attgcgatgg cgaaactggt taaaacccgt    600
cagccgcgcc tgtttgatta tctgtttacc caccgtaaca aacacaaact gatggcgctg    660
attgatgttc cgcagatgaa accgctggtg catgtgagcg gcatgtttgg cgcctggcgc    720
ggcaaaccca gctgggtggc cccgctggcc tggcacccgg aaaatcgtaa cgccgtgatt    780
atggttgatc tggccggtga tattagcccg ctgctggaac tggatagcga taccctgcgt    840
gaacgcctgt ataccgccaa aaccgatctg ggcgataatg ccgccgtgcc ggtgaaactg    900
gttcacatta caaatgccc ggtgctggcc caggcgaaca ccctgcgccc ggaagatgcg    960
gatcgtctgg gtattaatcg ccagcattgt ctggataatc tgaaaatcct gcgtgaaaac   1020
ccgcaggtgc gtgaaaaagt ggtggcgatc ttccgcgaag cggaaccgtt caccccgagc   1080
gataacgtgg atgcgcagct gtataacggc ttctttagcg atgccgatcg cgcggcgatg   1140
aaaatcgttc tggaaaccga accgcgcaat ctgccggcgc tggatattac ctttgttgat   1200
aaacgtattg aaaaactgct gtttaattat cgtgcgcgca attttccggg taccctggat   1260
tatgccgaac agcagcgttg gctggaacat cgtcgtcagg ttttcacccc ggaatttctg   1320
cagggttatg cggatgaact gcagatgctg gttcagcagt atgccgatga aaagaaaaaa   1380
gtggcgctgc                                                          1390

SEQ ID NO: 6          moltype = AA   length = 485
FEATURE               Location/Qualifiers
source                1..485
                      mol_type = protein
                      organism = Escherichia coli
SEQUENCE: 6
MMNDGKQQST FLFHDYETFG THPALDRPAQ FAAIRTDSEF NVIGEPEVFY CKPADDYLPQ    60
PGAVLITGIT PQEARAKGEN EAAFAARIHS LFTVPKTCIL GYNNVRFDDE VTRNIFYRNF   120
YDPYAWSWQH DNSRWDLLDV MRACYALRPE GINWPENDDG LPSFRLEHLT KANGIEHSNA   180
HDAMADVYAT IAMAKLVKTR QPRLFDYLFT HRNKHKLMAL IDVPQMKPLV HVSGMFGAWR   240
GNTSWVAPLA WHPENRNAVI MVDLAGDISP LLELDSDTLR ERLYTAKTDL GDNAAVPVKL   300
VHINKCPVLA QANTLRPEDA DRLGINRQHC LDNLKILREN PQVREKVVAI FAEAEPFTPS   360
DNVDAQLYNG FFSDADRAAM KIVLETEPRN LPALDITFVD KRIEKLLFNY RARNFPGTLD   420
YAEQQRWLEH RRQVFTPEFL QGYADELQML VQQYADDKEK VALLKALWQY AEEIVSGSGH   480
HHHHH                                                               485

SEQ ID NO: 7          moltype = DNA   length = 804
FEATURE               Location/Qualifiers
source                1..804
                      mol_type = genomic DNA
                      organism = Escherichia coli
SEQUENCE: 7
atgaaatttg tctcttttaa tatcaacggc ctgcgcgcca gacctcacca gcttgaagcc    60
atcgtcgaaa agcaccaacc ggatgtgatt ggcctgcagg agacaaaagt tcatgacgat   120
atgtttccgc tcgaagaggt ggcgaagctc ggctacaacg tgttttatca cgggcagaaa   180
ggccattatg gcgtggcgct gctgaccaaa gagacgccga ttgccgtacg tcgcggcttt   240
cccggtgacg acgaagaggc gcagcggcgg attattatgg cggaaatccc ctcactgctg   300
ggtaatgtca ccgtgatcaa cggttacttc ccgcagggtg aaagccgcga ccatccgata   360
aaattcccg caaaagcgca gttttatcag aatctgcaaa actacctgga aaccgaactc   420
aaacgtgata tccggtact gattatgggc gatatgaata tcagccctac agatctggat   480
atcggcattg gcaagaaaa ccgtaagcgc tggctgcgta ccggtaaatg ctcttttcctg   540
ccggaagagc gcgaatggat ggacaggctg atgagctggg ggttggtcga taccttccgc   600
catgcgaatc cgcaaacagc agatcgtttc tcatggtttg attaccgctc aaaaggtttt   660
gacgataacc gtggtctgcg catcgacctg ctgctcgcca gccaaccgct ggcagaatgt   720
tgcgtagaaa ccggcatcga ctatgaaatc cgcagcatgg aaaaaccgtc cgatcacgcc   780
cccgtctggg cgaccttccg ccgc                                          804

SEQ ID NO: 8          moltype = AA   length = 268
FEATURE               Location/Qualifiers
source                1..268
                      mol_type = protein
                      organism = Escherichia coli
SEQUENCE: 8
MKFVSFNING LRARPHQLEA IVEKHQPDVI GLQETKVHDD MFPLEEVAKL GYNVFYHGQK    60
GHYGVALLTK ETPIAVRRGF PGDDEEAQRR IIMAEIPSLL GNVTVINGYF PQGESRDHPI   120
KFPAKAQFYQ NLQNYLETEL KRDNPVLIMG DMNISPTDLD IGIGEENRKR WLRTGKCSFL   180
PEEREWMDRL MSWGLVDTFR HANPQTADRF SWFDYRSKGF DDNRGLRIDL LLASQPLAEC   240
CVETGIDYEI RSMEKPSDHA PVWATFRR                                      268

SEQ ID NO: 9          moltype = DNA   length = 1275
FEATURE               Location/Qualifiers
source                1..1275
                      mol_type = genomic DNA
                      organism = Thermus thermophilus
SEQUENCE: 9
atgtttcgtc gtaaagaaga tctggatccg ccgctggcac tgctgccgct gaaaggcctg    60
cgcgaagccg ccgcactgct ggaagaagcg ctgcgtcaag ctaaacgcat tcgtgttcac   120
ggcgactatg atgcggatgg cctgaccggc accgcgatcc tggttcgtgg ctggccgcc   180
ctgggtgcgg atgttcatcc gtttatcccg caccgcctgg aagaaggcta tggtgtcctg   240
atgaacgcgt cccgaaaca tctggaagcc tcggacctgt ttctgaccgt tgactgcggc   300
attaccaacc atgcggaact gcgcgaactg ctggaaatg cgtgtgaagt cattgttacc   360
gatcatcata cgccgggcaa aacgccgccg ccgggtctgg tcgtgcatcc ggcgctgacg   420
```

```
ccggatctga aagaaaaacc gaccggcgca ggcgtggcgt ttctgctgct gtgggcactg   480
catgaacgcc tgggcctgcc gccgccgctg aatacgcggg acctggcagc cgttggcacc   540
attgccgacg ttgccccgct gtggggttgg aatcgtgcac tggtgaaaga aggtctggca   600
cgcatcccgg cttcatcttg ggtgggcctg cgtctgctgg ctgaagccgt gggctatacc   660
ggcaaagcgg tcgaagtcgc tttccgcatc gcgccgcgca tcaatgcggc ttcccgcctg   720
ggcgaagcgg aaaaagccct gcgcctgctg ctgacggatg atgcggcaga agctcaggcg   780
ctggtcggcg aactgcaccg tctgaacgcc cgtcgtcaga ccctggaaga agcgatgctg   840
cgcaaactgc tgccgcaggc cgaccccgaa gcgaaagcca tcgttctgct ggaccccggaa  900
ggccatccgg gtgttatggg tattgtggcc tctcgcatcc tggaagcgac cctgcgcccg   960
gtcttcctgg tggcccaggg caaaggcacc gtgcgttcgc tggctccgat ttccgccgtc  1020
gaagcactgc gcagcgcgga agatctgctg ctgcgttatg gtggtcataa agaagcggcc  1080
ggtttcgcaa tggatgaagc gctgtttccg gcgttcaaag cacgcgttga agcgtatgcc  1140
gcacgtttcc cggatccggt tcgtgaagtg gcactgctgg atctgctgcc ggaaccgggc  1200
ctgctgccgc aggtgttccg tgaactggca ctgctggaac cgtatggtga aggtaacccg  1260
gaaccgctgt tcctg                                                   1275

SEQ ID NO: 10          moltype = AA    length = 425
FEATURE                Location/Qualifiers
source                 1..425
                       mol_type = protein
                       organism = Thermus thermophilus
SEQUENCE: 10
MFRRKEDLDP PLALLPLKGL REAAALLEEA LRQGKRIRVH GDYDADGLTG TAILVRGLAA    60
LGADVHPFIP HRLEEGYGVL MERVPEHLEA SDLFLTVDCG ITNHAELREL LENGVEVIVT   120
DHHTPGKTPP PGLVVHPALT PDLKEKPTGA GVAFLLLWAL HERLGLPPPL EYADLAAVGT   180
IADVAPLWGW NRALVKEGLA RIPASSWVGL RLLAEAVGYT GKAVEVAFRI APRINAASRL   240
GEAEKALRLL LTDDAAEAQA LVGELHRLNA RRQTLEEAML RKLLPQADPE AKAIVLLDPE   300
GHPGVMGIVA SRILEATLRP VFLVAQGKGT VRSLAPISAV EALRSAEDLL LRYGGHKEAA   360
GFAMDEALFP AFKARVEAYA ARFPDPVREV ALLDLLPEPG LLPQVFRELA LLEPYGEGNP   420
EPLFL                                                              425

SEQ ID NO: 11          moltype = DNA    length = 738
FEATURE                Location/Qualifiers
source                 1..738
                       mol_type = genomic DNA
                       note = Bacteriophage lambda
                       organism = unidentified
SEQUENCE: 11
tccggaagcg gctctggtag tggttctggc atgacaccgg acattatcct gcagcgtacc    60
gggatcgatg tgagagctgt cgaacagggg gatgatgcgt ggcacaaatt acggctcggc   120
gtcatcaccg cttcagaagt tcacaacgtg atagcaaaac cccgctccgg aaagaagtgg   180
cctgacatga aaatgtccta cttccacacc ctgcttgctg aggtttgcac cggtgtggct   240
ccggaagtta acgctaaagc actggcctgg ggaaaacagt acgagaacga gccagaaacc   300
ctgtttgaat tcacttccgg cgtgaatgtt actgaatccc cgatcatcta cgcgacgaa    360
agtatgcgta ccgcctgctc tcccgatggt ttatgcagtg acggcaacgg ccttgaactg   420
aaaatgccgt ttacctcccg ggatttcatg aagttccggc tcggtggttt cgaggccata   480
aagtcagctt acatgccca ggtgcagtac agcatgtggg tacgcgaaa aaatgcctgc     540
tactttgcca actatgaccc gcgtatgaag cgtgaaggcc tgcattatgt cgtgattgag   600
cgggatgaaa agtacatggc gagttttgac gagatcgtgc cggagttcat cgaaaaaatg   660
gacgaggcac tggctgaaat tggttttgta tttggggagc aatggcgatc tggctctggt   720
tccggcagcg gttccgga                                                738

SEQ ID NO: 12          moltype = AA    length = 226
FEATURE                Location/Qualifiers
source                 1..226
                       mol_type = protein
                       note = Bacteriophage lambda
                       organism = unidentified
SEQUENCE: 12
MTPDIILQRT GIDVRAVEQG DDAWHKLRLG VITASEVHNV IAKPRSGKKW PDMKMSYFHT    60
LLAEVCTGVA PEVNAKALAW GKQYENDART LFEFTSGVNV TESPIIYRDE SMRTACSPDG   120
LCSDGNGLEL KCPFTSRDFM KFRLGGFEAI KSAYMAQVQY SMWVTRKNAW YFANYDPRMK   180
REGLHYVVIE RDEKYMASFD EIVPEFIEKM DEALAEIGFV FGEQWR                  226

SEQ ID NO: 13          moltype = DNA    length = 526
FEATURE                Location/Qualifiers
misc_feature           1..526
                       note = Synthetic polynucleotide
modified_base          1..4
                       mod_base = OTHER
                       note = n = 2'-O-methyl uracil
source                 1..526
                       mol_type = other DNA
                       organism = synthetic construct
SEQUENCE: 13
nnnnttttttt tttttttttt tttttttttt tttttttttg ccatcagatt                60
gtgtttgtta gtcgctggtt gtttctgttg gtgctgatat tgcttttgat gccgacccta   120
aatttttttgc ctgtttggtt cgctttgagt cttcttcggt tccgactacc ctcccgactg   180
cctatgatgt ttatcctttg aatggtcgcc atgatggtgg ttattatacc gtcaaggact   240
```

```
gtgtgactat tgacgtcctt ccccgtacgc cgggcaataa cgtttatgtt ggtttcatgg    300
tttggtctaa ctttaccgct actaaatgcc gcggattggt ttcgctgaat caggttatta    360
aagagattat ttgtctccag ccacttaagt gaggtgattt atgtttggtg ctattgctgg    420
cggtattgct ctgctcttg ctggtggcgc catgtctaaa ttgtttggag gcggtctttt     480
tcccctttt tcccctttt tcccctttt tcccctttt tccccc                       526

SEQ ID NO: 14              moltype = DNA  length = 57
FEATURE                    Location/Qualifiers
misc_feature               1..57
                           note = Synthetic polynucleotide
source                     1..57
                           mol_type = other DNA
                           organism = synthetic construct
SEQUENCE: 14
agcgactaac aaacacaatc tgatggcttt ttttttttt ttttttttt ttttttt          57

SEQ ID NO: 15              moltype = AA  length = 760
FEATURE                    Location/Qualifiers
source                     1..760
                           mol_type = protein
                           organism = Methanococcoides burtonii
SEQUENCE: 15
MMIRELDIPR DIIGFYEDSG IKELYPPQAE AIEMGLLEKK NLLAAIPTAS GKTLLAELAM    60
IKAIREGGKA LYIVPLRALA SEKFERFKEL APFGIKVGIS TGDLDSRADW LGVNDIIVAT    120
SEKTDSLLRN GTSWMDEITT VVVDEIHLLD SKNRGPTLEV TITKLMRLNP DVQVVALSAT    180
VGNAREMADW LGAALVLSEW RPTDLHEGVL FGDAINFPGS QKKIDRLEKD DAVNLVLDTI    240
KAEGQCLVFE SSRRNCAGFA KTASSKVAKI LDNDIMIKLA GIAEEVESTG ETDTAIVLAN    300
CIRKGVAFHH AGLNSNHRKL VENGFRQNLI KVISSTPTLA AGLNLPARRV IIRSYRRFDS    360
NFGMQPIPVL EYKQMAGRAG RPHLDPYGES VLLAKTYDEF AQLMENYVEA DAEDIWSKLG    420
TENALRTHVL STIVNGFAST RQELFDFFGA TFFAYQQDKW MLEEVINDCL EFLIDKAMVS    480
ETEDIEDASK LFLRGTRLGS LVSMLYIDPL SGSKIVDGFK DIGKSTGGNM GSLEDDKGDD    540
ITVTDMTLLH LVCSTPDMRQ LYLRNTDYTI VNEYIVAHSD EPHEIPDKLK ETDYEWPMGE    600
VKTAMLLEEW VTEVSAEDIT RHFNVGEGDI HALADTSEWL MHAAAKLAEL LGVEYSSHAY    660
SLEKRIRYGS GLDLMELVGI RGVGRVRARK LYNAGFVSVA KLKGADISVL SKLVGPKVAY    720
NILSGIGVRV NDKHFNSAPI SSNTLDTLLD KNQKTFNDFQ                          760

SEQ ID NO: 16              moltype = AA  length = 300
FEATURE                    Location/Qualifiers
source                     1..300
                           mol_type = protein
                           organism = Eisenia fetida
SEQUENCE: 16
MSSSTVMADG FEEIEVDVVS VWKEGYAYEN RGNSSVQQKI TMTKGMKNLN SETKTLTATH    60
TLGRTLKVGD PFEIASVEVS YTFSHQKSQV SMTQTEVYSS QVIEHTVTIP PNKKFTRWKL    120
NADVGGTGIE YMYLIDEVTA IGADLTIPEV NKSRAKILVG RQIHLGETEI RIKHAERKEY    180
MTVISRKSWP AATLGNSNLF KFVLFEDSSG IRIKTLNTMY PGYEWAYSSD QGGIYFDESS    240
DNPKQRWALS KAMPLRHGDV VTFRNNFFTN SGMCYDDGPA TNVYCLEKRE DKWILEVVNT    300

SEQ ID NO: 17              moltype = AA  length = 300
FEATURE                    Location/Qualifiers
source                     1..300
                           mol_type = protein
                           organism = Eisenia fetida
SEQUENCE: 17
MSSRAGIAEG YEQIEVDVVA VWKEGYVYEN RGSTSVEQKI KITKGMRNLN SETKTLTASH    60
SIGSTISTGD LFEIATVDVS YSYSHEESQV SMTETEVYES KEIEHTITIP PTSKFTRWQL    120
NADVGGADIE YMYLIDEVTP IGGTLSIPQV IKSRAKILVG REIYLGETEI RIKHADRKEY    180
MTVVSRKSWP AATLGHSKLY KFVLYEDMYG FRIKTLNTMY SGYEYAYSSD QGGIYFDQGS    240
DNPKQRWAIN KSLPLRHGDV VTFMNKYFTR SGLCYYDGPA TDVYCLDKRE DKWILEVVKP    300

SEQ ID NO: 18              moltype = AA  length = 300
FEATURE                    Location/Qualifiers
source                     1..300
                           mol_type = protein
                           organism = Eisenia fetida
SEQUENCE: 18
MSATAVTADG LEEIEVDVVA VWKEGYVYEN RGDTSVEQKI TMTKGMKNLN SETKTLTATH    60
TVGRTLKVGD PFEIGSVEVS YSFSHQESQV SMTQTEVYSS QVIEHTVTIP PTSKFTRWKL    120
NADVGGTDIE YMYLIDEVTP ISVTQTIPQV IRSRAKILVG RQIHLGTTAV RIKHAERQEY    180
MTVIERKKWP AATLGKSNLF KFVLFEDSSG TRIKTLNTMY PGYEWAYSSD QGGVYFDESS    240
DNPKQRWALS KALPLRHGDV VTFMNKYFTN SGLCYDDGPA TNVYCLDKRE DKWILEVVNP    300

SEQ ID NO: 19              moltype = AA  length = 252
FEATURE                    Location/Qualifiers
source                     1..252
                           mol_type = protein
                           organism = Bacillus thuringiensis
SEQUENCE: 19
MDVIREYLMF NELSALSSSP ESVRSRFS -continued

```
CYKNVGTVQY VNRPTDINPN VILAQDTLTN NTNEPFTTTI TITGSFTNTS TVTSSTTTGF  120
KFTSKLSIKK VFEIGGEVSF STTIGTSETT TETITVSKSV TVTVPAQSRR TIQLTAKIAK  180
ESADFSAPIT VDGYFGANFP KRVGPGGHYF WFNPARDVLN TTSGTLRGTV TNVSSFDFQT  240
IVQPARSLLD EQ                                                     252
```